(12) United States Patent
Burkett

(10) Patent No.: US 11,779,369 B2
(45) Date of Patent: Oct. 10, 2023

(54) VACUUM-ASSISTED INSERTION DEVICE

(71) Applicant: Joseph Choate Burkett, Addison, TX (US)

(72) Inventor: Joseph Choate Burkett, Addison, TX (US)

(73) Assignee: Joseph Choate Burkett, Addison, TX (US)

( * ) Notice: Subject to any disclaimer, the term of this patent is extended or adjusted under 35 U.S.C. 154(b) by 0 days.

(21) Appl. No.: 17/831,004

(22) Filed: Jun. 2, 2022

(65) Prior Publication Data

US 2023/0091106 A1 Mar. 23, 2023

Related U.S. Application Data

(63) Continuation of application No. 17/287,968, filed as application No. PCT/US2019/057287 on Oct. 21, 2019, now Pat. No. 11,395,676.

(60) Provisional application No. 62/749,014, filed on Oct. 22, 2018.

(51) Int. Cl.
*A61B 17/34* (2006.01)
*A61B 90/30* (2016.01)
*A61B 90/00* (2016.01)
*A61B 17/00* (2006.01)

(52) U.S. Cl.
CPC ...... *A61B 17/3403* (2013.01); *A61B 17/3415* (2013.01); *A61B 90/30* (2016.02); *A61B 90/36* (2016.02); *A61B 2017/00221* (2013.01); *A61B 2017/00398* (2013.01); *A61B 2017/3409* (2013.01); *A61B 2017/3413* (2013.01); *A61B 2217/005* (2013.01); *A61B 2562/0271* (2013.01)

(58) Field of Classification Search
CPC ...... A61B 17/3403; A61B 2017/00221; A61B 2017/3409; A61B 2017/3413; A61B 2090/364; A61B 2090/3979; A61B 8/085; A61B 90/30; A61B 90/36; A61M 5/427
See application file for complete search history.

(56) References Cited

U.S. PATENT DOCUMENTS

| 10,178,984 B2 | 1/2019 | Hagy et al. |
| 11,395,676 B2 | 7/2022 | Burkett |
| 2006/0015066 A1 | 1/2006 | Turieo et al. |
| 2010/0010505 A1 | 1/2010 | Herlihy et al. |
| 2011/0166451 A1 | 7/2011 | Blaivas et al. |
| 2012/0259219 A1 | 10/2012 | Sheldon et al. |

(Continued)

FOREIGN PATENT DOCUMENTS

| JP | H04150846 A | 5/1992 |
| JP | 2004267534 A | 9/2004 |

(Continued)

OTHER PUBLICATIONS

PCT/US2019/057287 International Invitation to Pay Additional Fees dated Nov. 27, 2019.

(Continued)

*Primary Examiner* — Deanna K Hall
(74) *Attorney, Agent, or Firm* — Wilson Sonsini Goodrich & Rosati

(57) ABSTRACT

Insertion devices, systems, and methods for inserting a needle into a target tissue in an individual in need thereof are disclosed herein. Also disclosed herein are needle cartridges comprising a needle, a plate, and a needle holder. Also disclosed herein are methods of introducing a catheter into a target tissue in an individual in need thereof.

37 Claims, 24 Drawing Sheets

(56) References Cited

U.S. PATENT DOCUMENTS

| | | |
|---|---|---|
| 2012/0259221 A1 | 10/2012 | Sheldon et al. |
| 2013/0131597 A1 | 5/2013 | Blaivas et al. |
| 2013/0144165 A1 | 6/2013 | Ebbini et al. |
| 2015/0320439 A1 | 11/2015 | Andrews et al. |
| 2017/0196590 A1 | 7/2017 | Sperry et al. |
| 2017/0203053 A1 | 7/2017 | Burkett |
| 2018/0161502 A1 | 6/2018 | Nanan et al. |
| 2018/0280053 A1 | 10/2018 | Coker et al. |

FOREIGN PATENT DOCUMENTS

| | | |
|---|---|---|
| JP | 2008093146 A | 4/2008 |
| JP | 2008539932 A | 11/2008 |
| JP | 2011015960 A | 1/2011 |
| JP | 2013507175 A | 3/2013 |
| JP | 2013544574 A | 12/2013 |
| JP | 2014516652 A | 7/2014 |
| WO | WO-2015031481 A1 | 3/2015 |
| WO | WO-2015121171 A1 | 8/2015 |
| WO | WO-2020086491 A1 | 4/2020 |

OTHER PUBLICATIONS

PCT/US2019/057287 International Search Report and Written Opinion dated Feb. 6, 2020.
Japanese Application No. 2021-529263, Office Action dated Jul. 26, 2023.

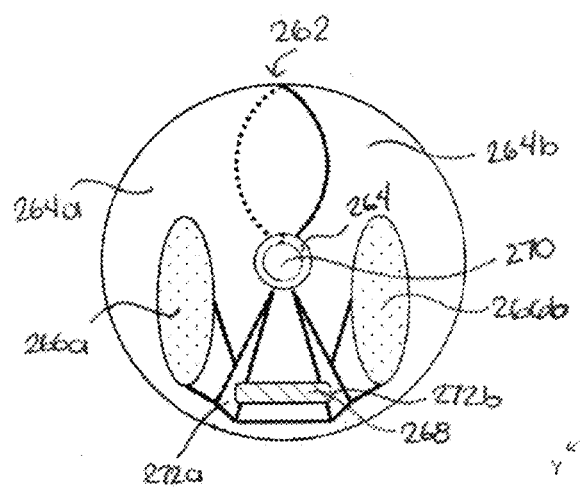
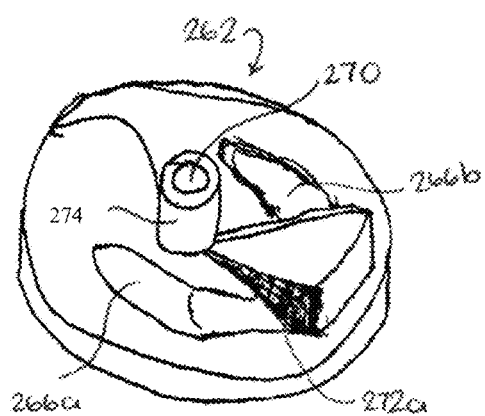
FIG. 11A
FIG. 11B
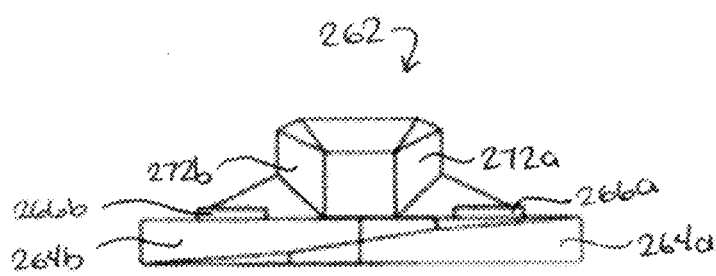
FIG. 11C

VACUUM-ASSISTED INSERTION DEVICE

CROSS-REFERENCE

This application is continuation of U.S. application Ser. No. 17/287,968, filed Apr. 22, 2021, which is a 371 of International Application No. PCT/US2019/057287, filed Oct. 21, 2019, which claims the benefit of U.S. Provisional Application No. 62/749,014, filed Oct. 22, 2018, which are incorporated herein by reference.

SUMMARY

Disclosed herein, in certain embodiments, are insertion devices for inserting a needle into a target tissue in an individual in need thereof, comprising: a housing comprising: an ultrasound transducer configured to emit and receive an ultrasound wave, and a cartridge receiver comprising a plurality of first connectors; a cartridge having a top surface, a bottom surface, a proximal end, and a distal end, the cartridge configured to be coupled to the cartridge receiver, comprising: a plurality of second connectors located on the top surface of the cartridge, configured to form an electrical connection with the plurality of first connectors of the cartridge receiver, a plate having a planar surface and a thickness configured to allow the ultrasound wave to pass therethrough, and a needle holder, comprising an interior having a proximal end and distal end a track therebetween, the track having track walls configured to guide the needle, a needle connector configured to couple the needle to a plurality of actuators, a needle holder opening located at the distal end of the needle holder, and a port located at the proximal end of the needle holder; wherein the needle exits through the needle holder opening; and an infrared sensor configured to emit and receive an infrared radiation.

In some embodiments, the target tissue is a blood vessel. In some embodiments, the target tissue is a joint or a soft tissue. In some embodiments, the soft tissue comprises a tendon, a ligament, fascia, a fibrous tissue, an adipose tissue, a nerve, a muscle, skin, or a synovial membrane. In some embodiments, the target tissue is a calcified tissue. In some embodiments, the calcified tissue is a bone. In some embodiments, the housing comprises at least one handle. In some embodiments, the cartridge is reversibly coupled to the cartridge receiver. In some embodiments, the plate is fixed relative to the cartridge receiver. In some embodiments, the needle holder is movable angular-wise and moves within the housing. In some embodiments, the needle holder is angled at a needle holder angle ranging between about 0° to about 80°. In some embodiments, the needle is an introducer needle, a biopsy needle, or a needle trocar. In some embodiments, the needle comprises a catheter and/or a guidewire. In some embodiments, the catheter is a peripherally inserted central catheter, a central venous catheter, a urinary catheter, an arterial catheter, a venous catheter, a tunneled catheter, a port catheter, or a non-tunneled central catheter. In some embodiments, the needle is in flow communication with a fluid injection line. In some embodiments, the cartridge receiver comprises a frame having a rail on either of its sides, the rail configured to secure the needle holder. In some embodiments, the plurality of actuators comprises a spring actuator and an angle actuator. In some embodiments, the spring actuator controls the longitudinal movement of the needle. In some embodiments, the angle actuator controls the needle holder angle. In some embodiments, the insertion device comprises a vacuum connection located within the housing, the vacuum connection comprising a vacuum connector operatively connected to the cartridge. In some embodiments, the vacuum connector is in vacuum communication with a vacuum source. In some embodiments, the vacuum source is configured to draw air through the needle holder opening. In some embodiments, the vacuum source is configured to draw air through the bottom surface of the cartridge. In some embodiments, the needle holder comprises a port lever or a collection tube configured to be received by the port. In some embodiments, the port lever moves within a cartridge arc path as the needle holder is moved from one selected position to another. In some embodiments, the insertion device comprises a power source. In some embodiments, the insertion device comprises a disposable sleeve configured for receiving the cartridge. In some embodiments, the infrared sensor comprises an infrared radiation source. In some embodiments, the infrared radiation source is a light emitting diode (LED) or an organic light emitting diode (OLED). In some embodiments, the infrared sensor comprises an infrared radiation detector. In some embodiments, the infrared radiation detector is an infrared photodetector or a temperature detector. In some embodiments, the cartridge serves as a barrier between the cartridge and the insertion device or between the insertion device and an individual. The cartridge can be preloaded with a therapeutic agent, wherein the therapeutic agent is delivered to the individual through the needle. The cartridge can further comprise an injection device. An anesthetizing agent can be delivered to the individual through the injection device. The injection device can be an additional needle.

Disclosed herein, in certain embodiments, are insertion systems for inserting a needle into a target tissue in an individual in need thereof, comprising: a housing comprising: an ultrasound transducer configured to emit and receive an ultrasound wave, and a cartridge receiver comprising a plurality of first connectors; a cartridge having a top surface, a bottom surface, a proximal end, and a distal end, configured to be coupled to the cartridge receiver, comprising: a plurality of second connectors located on the top surface of the cartridge, configured to form an electrical connection with the plurality of first connectors of the cartridge receiver, a plate having a planar surface and a thickness configured to allow the ultrasound wave to pass therethrough, and a needle holder, comprising an interior having a proximal end and a distal end, and a track therebetween, the track having track walls configured to guide the needle, a needle connector configured to couple the needle to a plurality of actuators, a needle holder opening located at the distal end of the needle holder, and a port located at the proximal end of the needle holder; wherein the needle exits through the needle holder opening; an infrared sensor configured to emit and receive an infrared radiation; a display screen operatively coupled to the ultrasound transducer and the infrared sensor, the display screen configured to display an ultrasound image and an infrared image of the target tissue location, the needle, and a needle insertion point; and a computing device comprising a processor operatively coupled to the ultrasound transducer, the infrared sensor, the display screen, and the plurality of actuators and a non-transitory computer readable storage medium with a computer program including instructions executable by the processor causing the processor to: a) convert the ultrasound wave emitted from the ultrasound transducer into the ultrasound image and display the ultrasound image on the display screen, b) convert the infrared radiation emitted from the infrared sensor into the infrared image and display the infrared image on the display screen, c) localize the target tissue, d) calculate the needle insertion point into the target tissue, and e) track the position of the tip of the needle once the needle is inserted into the target tissue. The cartridge can be pre-loaded with a therapeutic agent, wherein the therapeutic agent is delivered to the individual through the needle. The cartridge can further comprise an injection device. An anesthetizing agent can be delivered to the individual through the injection device. The injection device can be an additional needle.

In some embodiments, the target tissue is a blood vessel. In some embodiments, the target tissue is a joint or a soft tissue. In some embodiments, the soft tissue comprises a tendon, a ligament, fascia, a fibrous tissue, an adipose tissue, a nerve, a muscle, skin, or a synovial membrane. In some embodiments, the target tissue is a calcified tissue. In some embodiments, the calcified tissue is a bone. In some embodiments, the housing comprises at least one handle. In some embodiments, the cartridge is reversibly coupled to the cartridge receiver. In some embodiments, the plate is fixed relative to the cartridge receiver. In some embodiments, the needle holder is movable angular-wise and moves within the housing. In some embodiments, the needle holder is angled at a needle holder angle ranging between about 0° to about 80°. In some embodiments, the needle is an introducer needle, a biopsy needle, or a needle trocar. In some embodiments, the needle comprises a catheter and/or a guidewire. In some embodiments, the catheter is a peripherally inserted central catheter, a central venous catheter, a urinary catheter, an arterial catheter, a venous catheter, a tunneled catheter, a port catheter, or a non-tunneled central catheter. In some embodiments, the needle is in flow communication with a fluid injection line. In some embodiments, the cartridge receiver comprises a frame having a rail on either of its sides, the rail configured to secure the needle holder. In some embodiments, the plurality of actuators comprises a spring actuator and an angle actuator. In some embodiments, the spring actuator controls the longitudinal movement of the needle. In some embodiments, the angle actuator controls the needle holder angle. In some embodiments, the insertion systems comprise a vacuum connection located within the housing, the vacuum connection comprising a vacuum connector operatively connected to the cartridge. In some embodiments, the vacuum connector is in vacuum communication with a vacuum source. In some embodiments, the vacuum source is configured to draw air through the needle holder opening. In some embodiments, the vacuum source is configured to draw air through the bottom surface of the cartridge. In some embodiments, the needle holder comprises a port lever or a collection tube configured to be received by the port. In some embodiments, the port lever moves within a cartridge arc path as the needle holder is moved from one selected position to another. In some embodiments, the insertion system comprises a power source. In some embodiments, the insertion system comprises a disposable sleeve configured for receiving the cartridge. In some embodiments, the insertion system comprises a power source. In some embodiments, the insertion system comprises a disposable sleeve configured for receiving the cartridge. In some embodiments, the display screen displays an ultrasound image of the target tissue location in the individual in need thereof, the needle, and a needle insertion point in real time. In some embodiments, the system comprises a user interface operatively coupled to the computing device. In some embodiments, the user interface comprises a touch screen and/or a plurality of buttons to control various functions of the insertion system. In some embodiments, the various functions of the insertion system comprise: controlling the longitudinal movement of the needle, controlling the needle holder angle, controlling the longitudinal movement of a catheter, enhancing the focus of the ultrasound image, centering the ultrasound image, activating the vacuum motor, or any combination thereof. In some embodiments, the infrared sensor comprises an infrared radiation source. In some embodiments, the infrared radiation source is a light emitting diode (LED) or an organic light emitting diode (OLED). In some embodiments, the infrared sensor comprises an infrared radiation detector. In some embodiments, the infrared radiation detector is an infrared photodetector or a temperature detector. In some embodiments, the instructions executable by the processor cause the processor to automatically adjust the position of the needle such that the needle is centered within the target tissue. In some embodiments, the cartridge serves as a barrier between the cartridge and the insertion device or between the insertion device and an individual. The cartridge can be pre-loaded with a therapeutic agent, wherein the therapeutic agent is delivered to the individual through the needle. The cartridge can further comprise an injection device. An anesthetizing agent can be delivered to the individual through the injection device. The injection device can be an additional needle.

Disclosed herein, in certain embodiments, are needle cartridges, comprising: a needle; a plate having a planar surface and a thickness configured to allow an ultrasound wave to pass therethrough; a needle holder, comprising an interior having a proximal end and a distal end and a track therebetween, the track having track walls configured to guide the needle, a needle connector configured to couple the needle to a plurality of actuators, a needle holder opening located at the distal end of the needle holder, and a port located at the proximal end of the needle holder; wherein the needle exits through the needle holder opening. In some embodiments, the cartridge is configured to couple to an insertion device. In some embodiments, the cartridge serves as a barrier between the cartridge and the insertion device or between the insertion device and an individual.

In some embodiments, the needle holder is movable angular-wise and moves within the housing. In some embodiments, the needle holder is angled at a needle holder angle ranging between about 0° to about 80°. In some embodiments, the needle is an introducer needle, a biopsy needle, or a needle trocar. In some embodiments, the needle comprises a catheter and/or a guidewire. In some embodiments, the catheter is a peripherally inserted central catheter, a central venous catheter, a urinary catheter, an arterial catheter, a venous catheter, a tunneled catheter, a port catheter, or a non-tunneled central catheter.

Disclosed herein, in certain embodiments, are imaging devices for locating a target tissue in an individual in need thereof, comprising: an ultrasound transducer configured to emit and receive an ultrasound wave; an infrared sensor configured to emit and receive an infrared radiation; and a display screen operatively coupled to the ultrasound transducer and the infrared sensor, the display screen configured to display an ultrasound image and an infrared image of the target tissue.

In some embodiments, the target tissue is a blood vessel. In some embodiments, the target tissue is a joint or a soft tissue. In some embodiments, the soft tissue comprises a tendon, a ligament, fascia, a fibrous tissue, an adipose tissue, a nerve, a muscle, skin, or a synovial membrane. In some embodiments, the target tissue is a calcified tissue. In some embodiments, the calcified tissue is a bone. In some embodiments, the imaging device comprises a vacuum connection located within the housing, the vacuum connection comprising a vacuum connector operatively connected to the cartridge. In some embodiments, the vacuum connector is in vacuum communication with a vacuum source. In some embodiments, the imaging device comprises a power source. In some embodiments, the infrared sensor comprises an infrared radiation source. In some embodiments, the infrared radiation source is a light emitting diode (LED) or an organic light emitting diode (OLED). In some embodiments, the infrared sensor comprises an infrared radiation detector. In some embodiments, the infrared radiation detector is an infrared photodetector or a temperature detector.

Disclosed herein, in certain embodiments, are methods of introducing a needle into a target tissue in an individual in need thereof, using the insertion device disclosed herein, comprising: securing the cartridge to the cartridge receiver; imaging the target tissue using the ultrasound probe and the infrared sensor by contacting the surface of the skin of the individual with the bottom surface of the cartridge; identifying the needle insertion point on the display screen; and adjusting the needle holder angle and moving the needle longitudinally, through the cartridge inlet, thereby introducing the needle at the needle insertion point and into the target tissue. The cartridge can be pre-loaded with a therapeutic agent, wherein the therapeutic agent is delivered to the individual through the needle. The cartridge can further comprise an injection device. An anesthetizing agent can be delivered to the individual through the injection device. The injection device can be an additional needle.

In some embodiments, adjusting the needle holder angle and moving the needle longitudinally are manually actuated. In some embodiments, adjusting the needle holder angle and moving the needle longitudinally are automatically actuated by the computing device. In some embodiments, the method comprises administering a therapeutic agent using the needle. In some embodiments, the method comprises collecting a biopsy sample using the needle.

Disclosed herein, in certain embodiments, are methods of sampling venous blood in an individual in need thereof, using the insertion device disclosed herein, comprising: securing the cartridge to the cartridge receiver; securing an evacuated collection tube to the port; imaging a blood vessel using the ultrasound probe and the infrared sensor by contacting the surface of the skin of the individual with the bottom surface of the cartridge; identifying the needle insertion point on the display screen; adjusting the needle holder angle and moving the needle longitudinally, through the cartridge inlet, thereby introducing the needle at the needle insertion point and into the blood vessel; and collecting venous blood from the individual into the evacuated, blood collection tube. The cartridge can be pre-loaded with a therapeutic agent, wherein the therapeutic agent is delivered to the individual through the needle. The cartridge can further comprise an injection device. An anesthetizing agent can be delivered to the individual through the injection device. The injection device can be an additional needle.

Disclosed herein, in certain embodiments, are methods of introducing a catheter into a target tissue in an individual in need thereof, using the insertion device disclosed herein, comprising: securing the cartridge to the cartridge receiver; imaging the target tissue using the ultrasound probe and the infrared sensor by contacting the surface of the skin of the individual with the bottom surface of the cartridge; identifying the catheter insertion point on the display screen; and adjusting the needle holder angle and moving the catheter longitudinally, through the cartridge inlet, thereby introducing the catheter at the catheter insertion point and into the target tissue.

Disclosed herein, in certain embodiments, are insertion devices for inserting a needle into a target tissue in an individual in need thereof, comprising: a housing comprising: a cartridge receiver comprising a plurality of first connectors; a cartridge having a top surface, a bottom surface, a proximal end, and a distal end, the cartridge configured to be coupled to the cartridge receiver, comprising: a plurality of second connectors located on the top surface of the cartridge, configured to form an electrical connection with the plurality of first connectors of the cartridge receiver, and a needle holder, comprising an interior having a proximal end and distal end a track therebetween, the track having track walls configured to guide the needle, a needle connector configured to couple the needle to a plurality of actuators, a needle holder opening located at the distal end of the needle holder, and a port located at the proximal end of the needle holder; wherein the needle exits through the needle holder opening; and an imaging apparatus configured to image the target tissue.

In some embodiments, the target tissue is a blood vessel. In some embodiments, the target tissue is a joint or a soft tissue. In some embodiments, the soft tissue comprises a tendon, a ligament, fascia, a fibrous tissue, an adipose tissue, a nerve, a muscle, skin, or a synovial membrane. In some embodiments, the target tissue is a calcified tissue. In some embodiments, the calcified tissue is a bone. In some embodiments, the housing comprises at least one handle. In some embodiments, the cartridge is reversibly coupled to the cartridge receiver. In some embodiments, the plate is fixed relative to the cartridge receiver. In some embodiments, the needle holder is movable angular-wise and moves within the housing. In some embodiments, the needle holder is angled at a needle holder angle ranging between about 0° to about 80°. In some embodiments, the needle is an introducer needle, a biopsy needle, or a needle trocar. In some embodiments, the needle comprises a catheter and/or a guidewire. In some embodiments, the catheter is a peripherally inserted central catheter, a central venous catheter, a urinary catheter, an arterial catheter, a venous catheter, a tunneled catheter, a port catheter, or a non-tunneled central catheter. In some embodiments, the needle is in flow communication with a fluid injection line. In some embodiments, the cartridge receiver comprises a frame having a rail on either of its sides, the rail configured to secure the needle holder. In some embodiments, the plurality of actuators comprises a spring actuator and an angle actuator. In some embodiments, the spring actuator controls the longitudinal movement of the needle. In some embodiments, the angle actuator controls the needle holder angle. In some embodiments, the insertion device comprises a vacuum connection located within the housing, the vacuum connection comprising a vacuum connector operatively connected to the cartridge. In some embodiments, the vacuum connector is in vacuum communication with a vacuum source. In some embodiments, the vacuum source is configured to draw air through the needle holder opening. In some embodiments, the vacuum source is configured to draw air through the bottom surface of the cartridge. In some embodiments, the needle holder comprises a port lever or a collection tube configured to be received by the port. In some embodiments, the port lever moves within a cartridge arc path as the needle holder is moved from one selected position to another. In some embodiments, the insertion device comprises a power source. In some embodiments, the insertion device comprises a disposable sleeve configured for receiving the cartridge. In some embodiments, the imaging apparatus is an ultrasound transducer, an infrared sensor, or a combination thereof. In some embodiments, the infrared sensor comprises an infrared radiation source. In some embodiments, the infrared radiation source is a light emitting diode (LED) or an organic light emitting diode (OLED). In some embodiments, the infrared sensor comprises an infrared radiation detector. In some embodiments, the infrared radiation detector is an infrared photodetector or a temperature detector. In some embodiments, the insertion device comprises an ultrasound transducer configured to emit and receive an ultrasound wave. In some embodiments, the cartridge comprises a plate having a planar surface and a thickness configured to allow the ultrasound wave to pass therethrough. In some embodiments, the cartridge serves as a barrier between the cartridge and the insertion device or between the insertion device and the individual. The cartridge can be pre-loaded with a therapeutic agent, wherein the therapeutic agent is delivered to the individual through the needle. The cartridge can further comprise an injection device. An anesthetizing agent can be delivered to the individual through the injection device. The injection device can be an additional needle.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 1A shows a front view of the insertion device. FIG. 1B illustrates the insertion device with an exemplary output image displayed on its display screen.

FIG. 2A shows an isometric view of the bottom or distal side of the insertion device. FIG. 2B shows anisometric view of the bottom or distal side of the insertion device when coupled with the cartridge.

FIG. 3A shows a side view of the insertion device and a port. FIG. 3B shows a side view of the insertion device at a different angle than what is shown in FIG. 3A.

FIG. 4A illustrates an isometric side view of an isolated needle holder showing a syringe and a catheter. FIG. 4B illustrates a side view of the needle holder as a needle and catheter enter a human blood vessel. FIG. 4C illustrates the insertion of a catheter using the insertion device. FIG. 4D illustrates an exemplary output image of a blood vessel lumen displayed on the display screen of the insertion device, while inserting a catheter into the blood vessel.

FIGS. 11A-C illustrate views of an embodiment of a skin attachment cup. FIG. 11A shows a top view of the skin attachment cup. FIG. 11B shows an isometric view of the skin attachment cup. FIG. 11C shows a front view of the skin attachment cup.

FIG. 17A illustrates three DOF mechanism wherein the first joint is rotary, the second joint is prismatic, and the third joint is rotary. FIG. 17B shows a DOF mechanism, wherein the first joint is prismatic, the second joint is rotary, and the third joint is prismatic. FIG. 17C shows a DOF mechanism, wherein all three joints are rotary. FIG. 17D shows a DOF mechanism with, wherein as the first joint is prismatic, the second joint is prismatic, and the third joint is rotary.

FIG. 17E shows a DOF mechanism, wherein as the first joint is rotary, the second joint is rotary, and the third joint is prismatic.

FIG. 19A shows the needle adjusted along X-axis and lined up with the target vessel prior to the needle insertion. FIG. 19B shows a necessary insertion angle of the needle to reach the vessel. FIG. 19C shows the needle rotated to the insertion angle. FIG. 19D shows the needle advanced along the insertion angle to penetrate the target vessel. FIG. 19E shows the needle advanced within the vessel along the length of the vessel.

DETAILED DESCRIPTION

Figure 1A:
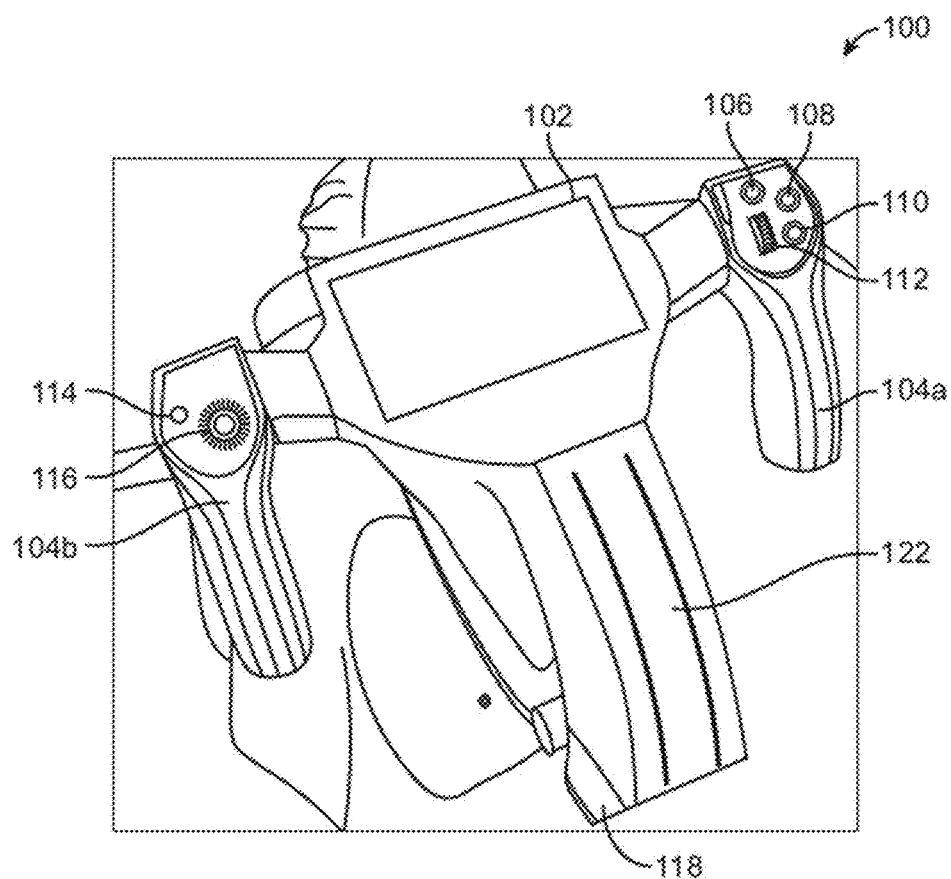
FIGS. 1A-B illustrate an embodiment of an insertion device being used on a patient.

While preferred embodiments of the subject matter disclosed herein have been shown and described herein, it will be obvious to those skilled in the art that such embodiments are provided by way of example only. Numerous variations, changes, and substitutions will now occur to those skilled in the art without departing from the subject matter disclosed herein. It should be understood that various alternatives to the embodiments of the subject matter disclosed herein may be employed in practicing the subject matter disclosed herein. It is intended that the following claims define the scope of the subject matter disclosed herein and that methods and structures within the scope of these claims and their equivalents be covered thereby.

Needle Insertion Techniques

In the medical field, the need often arises to inject or extract fluids from the body of a patient. Various medical procedures, including, but not limited to, phlebotomies, intravenous therapies, needle biopsies, epidurals, blood transfusions, and depot injections, all require the use of a hypodermic needle to gain access to interior organs. As such, the hypodermic needle is one of the most commonly-used tools in the practice of medicine.

Although so many common medical procedures require the use of a hypodermic needle, the effectiveness of such procedures is primarily reliant upon the proper insertion of the needle. Identifying structural locations under the surface of the skin is often difficult; and, at times, impossible. Variations in the thickness of skin, subcutaneous fat, and numerous other physical variations make it difficult, sometimes dangerous, and occasionally impossible to insert needles in specific locations. Due to such variations, inter-organ access is not impervious to failure, even when conducted by master nurses, skilled phlebotomists, or other doctors who commonly insert hypodermic needles.

Accurate access to interior organs, especially smaller, peripheral veins, is critical to the health and wellbeing of patients. However, smaller, peripheral veins and organs are typically the most difficult to access, especially for patients in the greatest need of intravenous access. For example, renal patients, trauma patients, critically-ill patients, and dehydrated patients require intravenous access; however, due to their health complications, the peripheral veins may be constricted, scarred, or otherwise damaged, thereby preventing access to the lumen of veins, arteries, and/or organs. Moreover, in emergency situations in which intravenous access is prevented, central or intraosseous line infusions, which have a higher frequency of life-threatening complications, must be performed.

Currently, procedures requiring needle insertion are typically performed manually by a physician or nurse. However, the variations in skill and knowledge between and among physicians and nurses, coupled with the inability to view underneath the skin, create a high frequency of error in needle placement.

Various imaging technologies, such as magnetic resonance imaging (MRI) and computer-aided tomography (CT), have been used in guided needle insertion methods. While imaging technology-guided needle placement has increased the likelihood of successful needle placement, it is replete with its own limitations. For example, very few physicians and nurses are taught or independently learn how to insert a needle using the guidance of medical imaging techniques, as only a handful of physician residency specialties, such as surgeons, anesthesiologists, and emergency physicians, encourage the training of imaging technology-guided needle placement. Even with such encouragement, due to the limited focus of such specialties, training of imaging technology-guided needle placement within such specialties is typically limited to central venous access (i.e., large vessels in the neck, chest, and thighs). Since these procedures involve large vessels and large needles, very few, if any, of these specialized physicians are trained to use the same technique to access smaller, peripheral vessels and organs.

Even with proper training, inter-organ access using imaging technology-guided needle placement is difficult in practice. In some cases, current imaging technology-guided needle placement requires the practitioner to use the non-dominant hand for the imaging probe and the dominant hand for the needle, all while looking at an image on a screen set off away from the patient. The multiple, independent variables increase the likelihood of error, even for the most skilled and dexterous practitioner. Accordingly, there exists a need for a medical apparatus for accurate needle insertion, which simplifies the guided, needle-insertion process and requires minimal training and skill.

Disclosed herein are devices, systems, and methods for guided-needle insertion and/or placement. The devices and systems described herein guide a user to insert and/or place a needle at a desired location with the assistance of ultrasound imaging, an infrared sensor, and/or a vacuum source.

Also, disclosed herein, in certain embodiments, are insertion devices for inserting a needle into a target tissue in an individual in need thereof, comprising: a housing comprising: an ultrasound transducer configured to emit and receive an ultrasound wave, and a cartridge receiver comprising a plurality of first connectors; a cartridge having a top surface, a bottom surface, a proximal end, and a distal end, coupled to the cartridge receiver, comprising: a plurality of second connectors located on the top surface of the cartridge, configured to form an electrical connection with the plurality of first connectors of the cartridge receiver, a plate having a planar surface and a thickness configured to allow the ultrasound wave to pass therethrough, and a needle holder, comprising an interior having a proximal end and distal end a track therebetween, the track having track walls configured to guide the needle, a syringe connector configured to couple the syringe to a plurality of actuators, a needle holder opening located at the distal end of the needle holder, and a port located at the proximal end of the needle holder; wherein the needle exits through the needle holder opening; and a an infrared sensor configured to emit and receive an infrared radiation.

Further disclosed herein, in certain embodiments, are vacuum-assisted insertion systems for inserting a needle into a target tissue in an individual in need thereof, comprising: a housing comprising: an ultrasound transducer configured to emit and receive an ultrasound wave, and a cartridge receiver comprising a plurality of first connectors; a cartridge having a top surface, a bottom surface, a proximal end, and a distal end, coupled to the cartridge receiver, comprising: a plurality of second connectors located on the top surface of the cartridge, configured to form an electrical connection with the plurality of first connectors of the cartridge receiver, a plate having a planar surface and a thickness configured to allow the ultrasound wave to pass therethrough, and a needle holder, comprising an interior having a proximal end and distal end, and a track therebetween, the track having track walls configured to guide the needle, a syringe connector configured to couple the syringe to a plurality of actuators, a needle holder opening located at the distal end of the needle holder, and a port located at the proximal end of the needle holder; wherein the needle exits through the needle holder opening; an infrared sensor configured to emit and receive an infrared radiation; a display screen operatively coupled to the ultrasound transducer and the infrared sensor, the display screen configured to display an ultrasound image and an infrared image of the target tissue location, the needle, and a needle insertion point; and a computing device comprising a processor operatively coupled to the ultrasound transducer, the infrared sensor, the display screen, and the plurality of actuators and a non-transitory computer readable storage medium with a computer program including instructions executable by the processor causing the processor to: a) convert the ultrasound wave emitted from the ultrasound transducer into the ultrasound image and display the ultrasound image on the display screen, b) convert the infrared radiation emitted from the infrared sensor into the infrared image and display the infrared image on the display screen; c) localize the target tissue, d) calculate the needle insertion point into the target tissue, and e) track the position of the tip of the needle once the needle is inserted into the target tissue.

Disclosed herein, in certain embodiments, are syringe cartridges comprising a syringe and a needle; a plate having a planar surface and a thickness configured to allow an ultrasound wave to pass therethrough; a needle holder, comprising an interior having a proximal end and a distal end and a track therebetween, the track having track walls configured to guide the needle, a syringe connector configured to couple the syringe to a plurality of actuators, a needle holder opening located at the distal end of the needle holder, and a port located at the proximal end of the needle holder; wherein the needle exits through the needle holder opening.

Disclosed herein, in certain embodiments, are imaging devices for locating a target tissue in an individual in need thereof, comprising an ultrasound transducer configured to emit and receive an ultrasound wave; an infrared sensor configured to emit and receive an infrared radiation; and a display screen operatively coupled to the ultrasound transducer and the infrared sensor, the display screen configured to display an ultrasound image and an infrared image of the target tissue.

Disclosed herein, in certain embodiments, are methods of introducing a needle into a target tissue of an individual using the insertion device, comprising: a) securing the cartridge to the cartridge receiver, b) imaging the target tissue using the ultrasound probe and the infrared sensor by contacting the surface of the skin of the individual with the bottom surface of the cartridge, c) identifying the needle insertion point on the display screen, and d) adjusting the needle holder angle and moving the needle longitudinally, through the cartridge inlet, thereby introducing the needle at the needle insertion point and into the target tissue.

Further described herein, in certain embodiments, are methods of sampling venous blood in an individual in need thereof, using the insertion device, comprising: a) securing the cartridge to the cartridge receiver, b) securing an evacuated collection tube to the port, c) imaging a blood vessel using the ultrasound probe and the infrared sensor by contacting the surface of the skin of the individual with the bottom surface of the cartridge, d) identifying the needle insertion point on the display screen, e) adjusting the needle holder angle and moving the needle longitudinally, through the cartridge inlet, thereby introducing the needle at the needle insertion point and into the blood vessel, and f) collecting venous blood from the individual into the evacuated, blood collection tube.

Also described herein, in certain embodiments, are methods of introducing a catheter into target tissue in an individual in need thereof, using the insertion device, comprising: a) securing the cartridge to the cartridge receiver, b) imaging the target tissue using the ultrasound probe and the infrared sensor by contacting the surface of the skin of the individual with the bottom surface of the cartridge, c) identifying the needle insertion point on the display screen, and d) adjusting the needle holder angle and moving the catheter longitudinally, through the cartridge inlet, thereby introducing the catheter at the catheter insertion point and into the target tissue.

Certain Definitions

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

Throughout this application, various embodiments of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "about" or "approximately" refers to an amount that is near the stated amount by about 10%, 5%, or 1%, including increments therein. For example, "about" or "approximately" means a range including the particular value and ranging from 10% below that particular value and spanning to 10% above that particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker). The terms "individual," "patient," or "subject" encompass mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiments, the mammal is a human.

The terms "user," "health care worker," "doctor," and "physician" are used interchangeably. These terms refer to any person that operates the devices described herein. Additional non-limiting examples of a user include "registered nurse," "nurse practitioner," and "physician's assistant."

The term "proximal," as used herein, is defined as situated closest or nearer to the user holding and/or operating the insertion device, unless otherwise indicated.

The term "distal," as used herein, is defined as situated farthest to the user holding and/or operating the insertion device, unless otherwise indicated.

The term "lateral," as used herein, is defined as situated and/or moving towards, closer, or nearer to the sides (e.g., right or left) of the insertion device, unless otherwise indicated.

The term "medial," as used herein, is defined as situated closer or nearer to the midline of the device, unless otherwise indicated.

The term "ultrasound transducer" and "ultrasound probe," as used herein, are used interchangeably.

Needle Insertion Devices

Disclosed herein, in certain embodiments, are insertion devices for inserting a needle into a target tissue in an individual in need thereof. Also disclosed herein, are imaging devices for locating a target tissue in an individual in need thereof. In some embodiments, the imaging devices comprise an ultrasound transducer configured to emit and receive an ultrasound wave. In some embodiments, the imaging devices comprise an infrared sensor configured to emit and receive an infrared radiation.

In some embodiments, the target tissue is a blood vessel. In some embodiments, the target tissue is the lumen of a blood vessel. In some embodiments, the blood vessel is a vein, a venule, an artery, or a capillary.

In some embodiments, the target tissue is a vein. In some embodiments, the vein is a cephalic vein. In some embodiments, the vein is a basilic vein. In some embodiments, the vein is a median cephalic vein. In some embodiments, the vein is a median cubital vein. In some embodiments, the vein is a vein in the antecubital fossa. In some embodiments, the vein is an internal jugular vein. In some embodiments, the vein is a subclavian vein. In some embodiments, the vein is a peripheral vein. In some embodiments, the peripheral vein is a peripheral vein in an arm. In some embodiments, the peripheral vein is a peripheral vein in a hand. In some embodiments, the peripheral vein is a peripheral vein in a leg. In some embodiments, the peripheral vein is a peripheral vein in a foot. In some embodiments, the vein is a jugular vein, a hepatic vein, a basilic vein, a saphenous vein, a cephalic vein, a superior vena cava, an inferior vena cava, a pulmonary vein, a subclavian vein, a common iliac vein, an axillary vein, a portal vein, a renal vein, a popliteal vein, a brachiocephalic vein, a posterior tibial vein, a vertebral vein, a median cubital vein, an anterior tibial vein, a retromandibular vein, a femoral vein, a vein from a pterygoid plexus, an azygos vein, a superior mesenteric vein, a posterior auricular vein, a superior sagittal sinus vein, a superior ophthalmic vein, an internal iliac vein, a superficial temporal vein, a coronary sinus, a diploic vein, an anterior jugular vein, a common facial vein, a nasofrontal vein, an occipital vein, an external iliac vein, a deep vein of the thigh, an inferior ophthalmic vein, a vein connecting to an inferior petrosal sinus, an inferior thyroid vein, a splenic vein, a median antebrachial vein, a vein connecting to a superior petrosal sinus, a middle thyroid vein, a deep facial vein, a vein connecting to an inferior sagittal sinus, or a frontal vein. In some embodiments, the jugular vein is an internal jugular vein or an exterior jugular vein.

In some embodiments, the artery is an elastic artery or a distributing artery. In some embodiments, the artery is an aorta, an internal carotid artery, an external iliac artery, an internal iliac artery, a common carotid artery, a common iliac artery, a brachiocephalic artery, a radial artery, a subclavian artery, a femoral artery, a brachial artery, a popliteal artery, a pulmonary artery, a vertebral artery, an aortic arch, a left coronary artery, an external carotid artery, an abdominal aorta, an ulnar artery, a celiac artery, a right coronary artery, an axillary artery, a common hepatic artery, a splenic artery, an anterior tibial artery, a superior mesenteric artery, an internal thoracic artery, a descending thoracic aorta, an anterior interventricular branch of a left coronary artery, a posterior tibial artery, an ascending aorta, a maxillary artery, a descending aorta, a left gastric artery, a dorsalis pedis artery, an ophthalmic artery, a thyrocervical trunk, an inferior mesenteric artery, a costocervical trunk, a deep artery of a thigh, an occipital artery, a supraorbital artery, an angular artery, a median sacral artery, an anterior ethmoidal artery, a posterior ethmoidal artery, a basilar artery, a superficial temporal artery, a renal artery, a circle of Willis, or a middle cerebral artery.

In some embodiments, the target tissue is a joint. In some embodiments, the joint is a synovial joint, a cartilaginous joint, a facet joint, or a synovial joint. In some embodiments, the target tissue is a knee. In some embodiments, the target tissue is a meniscus, an anterior cruciate ligament, a posterior cruciate ligament, a lateral collateral ligament, or a medial collateral ligament. In some embodiments, the target tissue is a soft tissue. In some embodiments, the soft tissue comprises a tendon, a ligament, fascia, a fibrous tissue, an adipose tissue, a nerve, a muscle, skin, or a synovial membrane. In some embodiments, the target tissue is a calcified tissue. In some embodiments, the calcified tissue is a bone. In some embodiments, the soft tissue is a neoplasm. In some embodiments, the neoplasm is benign. In some embodiments, the neoplasm is malignant.

In some embodiments, the target tissue is an organ. In some embodiments, the organ is a liver, a pancreas, a stomach, a large intestine, a small intestine, a lung, a heart, skin, an esophagus, a duodenum, a jejunum, an ileum, a gallbladder, a mesentery, an appendix, a diaphragm, an ovary, a fallopian tube, a uterus, a vagina, a placenta, a prostate, a testis, a thyroid gland, a parathyroid gland, an adrenal gland, a spleen, a tonsil, a spinal cord, a bone marrow, In some embodiments, the target tissue is a lymphatic vessel or a lymph node. In some embodiments, the target tissue is a nerve. In some embodiments, the target tissue is a ligament, a muscle, or a tendon. In some embodiments, the target tissue is a breast or a mammary tissue. In some embodiments, the target tissue is a membrane of the human body. In some embodiments, the membrane is a mucous membrane, a serous membrane, a cutaneous membrane, or a synovial membrane. In some embodiments, the insertion devices described herein aid in the insertion of a medical device (e.g., a needle) into a target tissue location and penetrate through skin and/or other organs, or through one or more membranes of the body.

FIG. 1A shows a front view of the insertion device 100. In some embodiments, the present description provides an insertion device 100 with a user interface that allows for insertion of a needle and/or catheter into an individual. In some embodiments, the insertion device 100 comprises a housing 122. In some embodiments, the housing 122 protects internal elements of the insertion device 100 such as, but not limited to, electric circuitry, a power source, an ultrasound transducer, and/or an infrared sensor. In some embodiments, the housing comprises an ultrasound transducer (not shown in FIG. 1A).

In some embodiments, the housing comprises at least one handle. In some embodiments, the housing comprises at least two handles. In some embodiments, the housing 122 comprises a right handle 104a and a left handle 104b, as shown in FIG. 1A. In some embodiments, the right handle 104a and the left handle 104b are ergonomically shaped. In some embodiments, the right handle 104a and the left handle 104b help the user to control the position of the insertion device 100. In some embodiments, the right handle 104a protrudes from a right side of the insertion device 100 and the left handle 104b protrudes from a left side of the insertion device 100. In some embodiments, the right handle 104a and the left handle 104b comprise a user hardware interface.

Figure 1B:
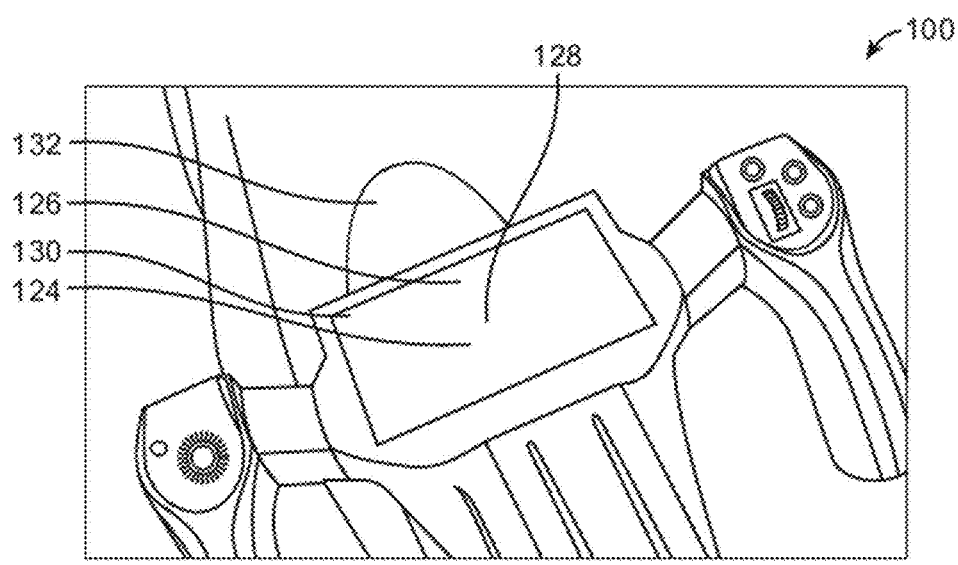

In some embodiments, the user hardware interface comprises a plurality of knobs, buttons, sliders, switches, and/or touchscreens, as shown in FIGS. 1A and 1B. In some embodiments, the user hardware interface is located on any suitable part of the insertion device 100. For example, in some embodiments, the user hardware interface is located on a proximal side of the housing 122. In some embodiments, the user hardware interface is located on a distal side of the housing 122. In some embodiments, the user hardware comprises a positioning dial 116, a gear wheel 112, a needle withdrawal button 106, a catheter insertion button 108, an infrared sensor button 114, and a needle insertion button 110. In some embodiments, the positioning dial 116 adjusts the longitudinal location of the needle holder (not shown in FIG. 1A). In some embodiments, the gear wheel 112 adjusts the angle of the needle (not shown in FIG. 1A). In some embodiments, the needle is alternatively adjusted manually; for example, by moving the needle holder and/or syringe using a knob and/or gears.

In some embodiments, the location of the positioning dial 116 is on a distal end of the left handle 104b, as shown in FIG. 1A. In some embodiments, the location of the gear wheel 112 is on a distal end of the right handle 104b, as shown in FIG. 1A. In some embodiments, the needle withdraw button 106, the catheter insertion button 108, the needle insertion button 110, and the infrared sensor button 114 comprise a virtual switch, a physical switch, or any combination thereof. In some embodiments, the needle withdraw button 106 allows the user to extract the needle from the patient following an injection. In some embodiments, the needle insertion button 110 controls the backward movement of the needle. In some embodiments, the needle insertion button 110 controls the retraction of the needle. In some embodiments, the needle withdraw button 106 is located on the distal end of the right handle 104a positioned distal to the gear wheel 112. In some embodiments, the catheter insertion button 108 allows the user to insert a catheter into the patient after adjusting the location of the needle. In some embodiments, the catheter insertion button 108 controls the forward movement of the catheter. In some embodiments, the catheter insertion button 108 controls the deployment of the catheter into the target tissue of the individual. In some embodiments, the catheter insertion button 108 is located on the right handle 104a laterally to the gear wheel 112.

In some embodiments, the needle insertion button 110 allows the user to insert the needle into the individual for injection after adjusting the location of the needle. In some embodiments, the needle insertion button 110 controls the forward movement of the needle. In some embodiments, the needle insertion button 110 controls the deployment of the needle into a target tissue of the individual. The needle insertion button 110 is located on the right handle 104a laterally to the gear wheel 112 and distally to the needle insertion button 110. In some embodiments, the infrared sensor button 114 allows the user to activate the infrared sensor prior to injection. In some embodiments, the infrared sensor button 114 is located on the left handle 104b distally to the gear wheel 112. In some embodiments, the user hardware interface elements (e.g., buttons, knobs, sliders, switches, and/or touchscreens) of the insertion device 100 are placed in any suitable configuration.

In some embodiments, the insertion device 100 comprises a display screen 102 for viewing an image of a target tissue. In some embodiments, the image is an ultrasound image. In some embodiments, the image is an infrared image. In some embodiments, the image is a combination of an ultrasound image and an infrared image. In some embodiments, the size of the display screen 102 and the resolution of the display screen 102 varies in combination. In some embodiments, the display screen 102 is located on the distal end of the device, farthest to the user, when the device is placed on the surface of the skin of the patient, as seen in FIG. 1A, for example.

FIG. 1B shows the insertion device 100 displaying an exemplary image 124 of a target tissue when the insertion device 100 is being pressed against the skin of the individual 132. In some embodiments, the visual information provided to the user via a display screen is an image 124. In some embodiments, the image 124 is an ultrasound image. In some embodiments, the image 124 is an infrared image. In some embodiments, the image 124 is a combination of an ultrasound image and an infrared image. In some embodiments, the image 124 is an ultrasound image representing a target tissue (e.g., a blood vessel). In some embodiments, the image 124 is an infrared image representing a target tissue (e.g., a blood vessel). In some embodiments, the image 124 is a combination of an ultrasound image and an infrared image representing a target tissue (e.g., a blood vessel). In some embodiments, the combination of the ultrasound image and the infrared image is a superimposed image. In some embodiments, the combination of the ultrasound image and the infrared image are displayed side by side on the display screen. In some embodiments, the user selects which type of image (e.g., ultrasound or infrared) she or he desires to view individually or in combination.

In some embodiments, the image 124 comprises a needle entry location with respect to the target tissue of the patient. In some embodiments, the image 124 comprises an indicator that guides the user to insert the needle into the target tissue location. In some embodiments, the image 124 comprises an indicator that indicates the location of the target tissue. In some embodiments, the indicator is an indicator line 126, as shown in FIG. 1B. In some embodiments, the indicator line 126 is aligned with the midline of a blood vessel lumen. In some embodiments, the indicator line 126 is aligned with the midline of a target tissue. In some embodiments, the indicator is an indicator marking 128, as shown in FIG. 1B. In some embodiments, the indicator marking 128 is aligned with the midline of a blood vessel lumen. In some embodiments, the indicator marking 128 is aligned with the midline of a target tissue. In some embodiments, a dotted line is displayed on the display screen 102 to represent the indicator marking 128. In some embodiments, the indicator line 126 displays the midline of the applicable tissue. In some embodiments, the indicator line 126 is automatically adjusted in real time by the insertion device 100. In some embodiments, the indicator line 126 adjusts in real time based on the inputs of the positioning dial 116. In some embodiments, the dotted indicator line 126 reflects the movement of the needle laterally. In some embodiments, a solid "x" marking is displayed on the display screen 102 to represent the insertion indicator marking 128. In some embodiments, the insertion indicator marking 128 displays the point of insertion within the tissue. In some embodiments, the insertion indicator marking 128 adjusts in real time based on the inputs of the gear wheel. In some embodiments, the marking 128 reflects the movement of the needle proximally.

In some embodiments, the image 124 comprises a position or a location of the needle during insertion (i.e., the needle position and/or the needle location is displayed in real time on the display screen). In some embodiments, the image 124 comprises a projected track of the needle. In some embodiments, the projected track of the needle guides the user to insert the needle at a target tissue location. In some embodiments, the projected track of the needle displays an entry point location at the skin level of the patient. In some embodiments, the entry point location at the skin level of the patient is represented by the indicator marking 128. In some embodiments, the projected track of the needle comprises a line, one or more dashes, one or more letters, a geometric figure, or any other type of marker or visual cue that is displayed on the display screen. In some embodiments, the projected track of the needle is a projected needle position (i.e., an estimated location of the needle) at the skin level (i.e., a skin level insertion point) and/or subcutaneously (i.e., estimated location of the needle once the needle has been inserted into the tissue of the patient). In some embodiments, the image 124 comprises a label 130, as shown in FIG. 1B. In some embodiments, the label 130 displays the name of the image file, the name of the patient, the target tissue type, the procedure being performed, or any combination thereof.

In some embodiments, the user interface of the insertion device 100, allows for a real-time display of the target tissue and adjustment of needle positioning. In some embodiments, the display screen comprises an adjustable indicator line 126 based on the settings input by the user. In some embodiments, as the user adjusts the settings using the plurality of switches and gears, the indicator line 126 on the display screen 102 automatically adjusts to display the adjusted indicator line 126 prior to inserting a needle into the arm of the patient 132. In some embodiments, the settings input by the user modify the insertion indicator marking 128. In some embodiments, the visual display of the insertion indicator marking 128 allows the user to identify the target tissue. In some embodiments, the label 130 provides the user with relevant information, such as, but not limited to personal user information, the type of cartridge attached to the insertion device 100, the type of device to be inserted (e.g., the type of needle or cartridge), the substance to be administered (e.g., a drug), and/or any relevant dosage information. In some embodiments, the label 130 is located on the distal, left edge of the image 124, as shown in FIG. 1B. In some embodiments, the label 130 is located on any suitable part of the image 124.

Figure 2A:
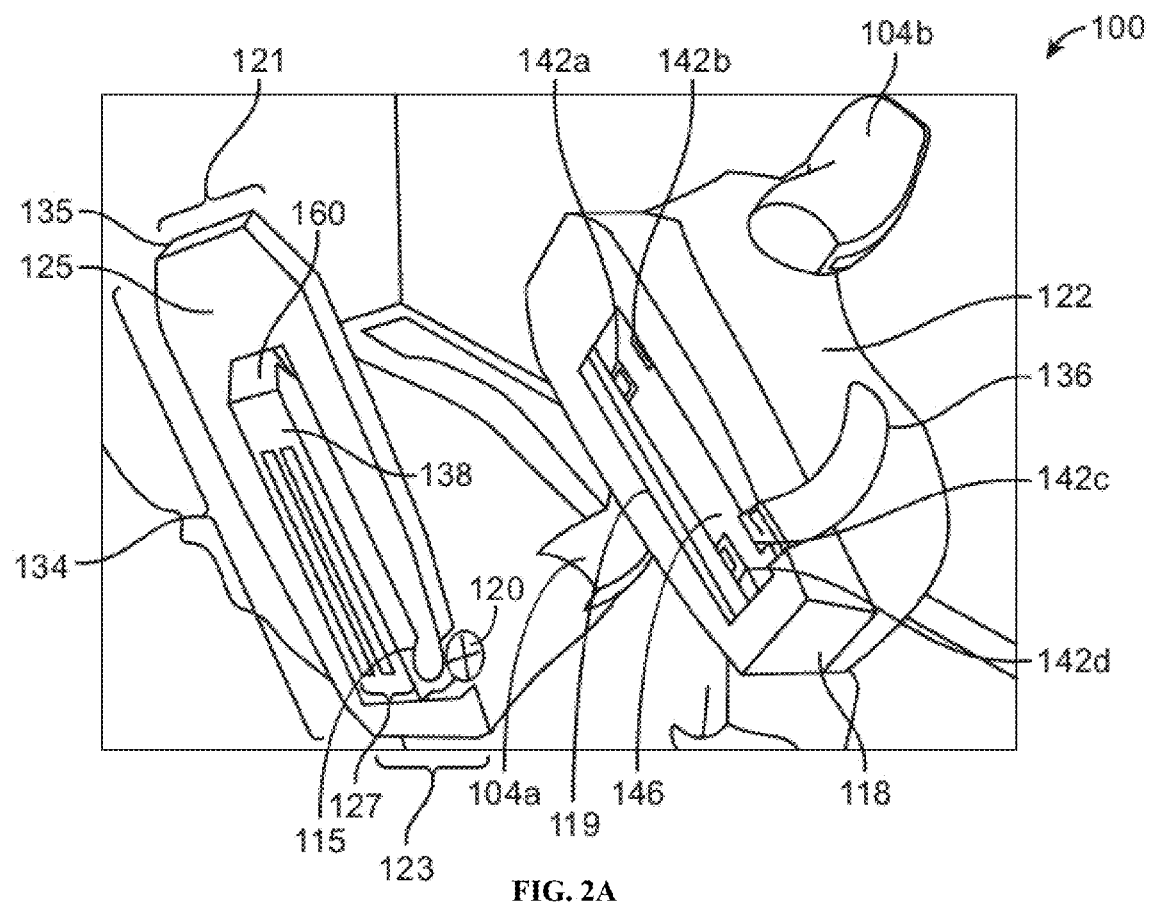
FIGS. 2A-B illustrate an embodiment of the insertion device comprising a cartridge.
Figure 2B:
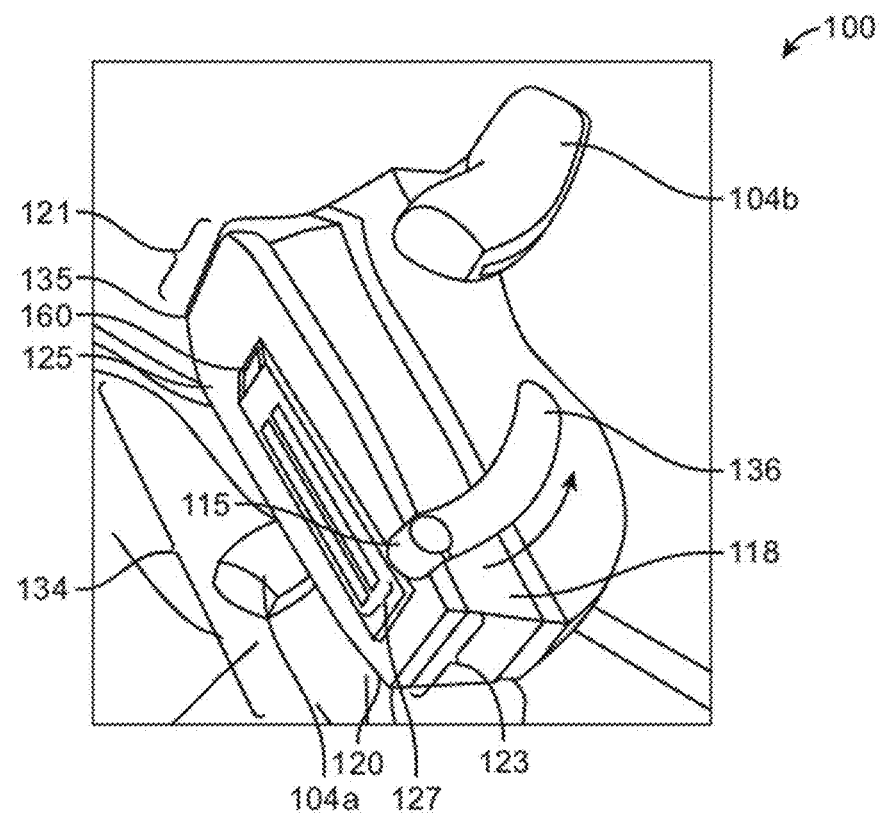

FIG. 2A shows an isometric view of the bottom or distal side of the insertion device 100. FIG. 2A also shows the cartridge 134 prior to being attached to the cartridge receiver 118. FIG. 2B shows the insertion device after the cartridge 134 is attached to the cartridge receiver 118. In some embodiments, the present description provides a device for implementing an ultrasound, an infrared sensor, and/or a vacuum suction technology for aid in needle and/or catheter insertion. In some embodiments, the housing 122 comprises a cartridge receiver 118. In some embodiments, the cartridge receiver 118 comprises a plurality of first connectors. As shown in FIG. 2A, in some embodiments, the plurality of first connectors comprises an upper left connector 142a, an upper right connector 142b, a lower right connector 142c, and a lower right connector 142d. In some embodiments, the plurality of first connectors is a plurality of tabs, snap fit connectors, male connectors, and/or female connectors.

In some embodiments, the insertion device 100 comprises a cartridge 134. In some embodiments, the cartridge 134 has a top surface (not shown in FIG. 2A), a bottom surface (the side shown in FIG. 2A), a proximal end 123, and a distal end 121. In some embodiments, the cartridge 134 is configured to be coupled to the cartridge receiver 118. In some embodiments, the cartridge 134 comprises a plurality of second connectors (not shown in FIGS. 2A and 2B). In some embodiments, the plurality of second connectors is located on the top surface of the cartridge 134. In some embodiments, the plurality of second connectors is configured to form an electrical connection with the plurality of first connectors of the cartridge receiver 118.

FIG. 2B shows the cartridge 134 prior to being attached to the insertion device 100. In some embodiments, the cartridge 134 fits into the cartridge receiver 118 on the insertion device 100. In some embodiments, the cartridge is located medially between the right handle 104a and the left handle 104b. In some embodiments, the port 120 serves an opening to allow for the insertion of tubing into the device. In some embodiments, the port 120 comprises means for manually adjusting the angle of the needle prior to needle insertion. In some embodiments, the port 120 is located on the distal end of the insertion device 100 and on the dorsal side of the device.

In some embodiments, the needle holder 138 contains the needle and syringe (not shown in FIGS. 2A and 2B). In some embodiments, the needle extends from the proximal end of the needle holder 127 to the distal end of the needle holder 125 when placed within the track. In some embodiments, the needle holder 138 comprises a needle holder opening 160. In some embodiments, the needle exits through the needle holder opening 160. In some embodiments, the needle holder opening 160 faces the distal end of the cartridge 121. In some embodiments, the needle holder opening 160 is aligned with the center of the plate 135.

In some embodiments, the needle holder 138 comprises a port 115. In some embodiments, the port 115 is located at the proximal end 127 of the needle holder. In some embodiments, the port 115 comprises a tubular body defining a cavity therein. In some embodiments, the tubular body connects to the interior of the needle holder 138. In some embodiments, the port 115 is intended to be accessed with tubing. In some embodiments, the tubing is in fluid communication with the syringe and needle. In some embodiments, the port 115 is intended to be accessed with a tube 120. In some embodiments, the needle holder 138 comprises a collection tube configured to be received by the port 115. In some embodiments, the needle holder 138 comprises a port lever configured to be received by the port 115. In some embodiments, the port lever is a projecting arm or handle. In some embodiments, the user manually controls and/or adjusts the angle of the needle holder by moving the port lever. In some embodiments, the user manually controls and/or adjusts the angle of the needle holder by manually moving the port lever within a needle holder track 136, as shown by the arrow in FIG. 2B. In some embodiments, the tube 120 is in fluid communication with the syringe and needle. In some embodiments, the tube 120 is a blood collection tube. In some embodiments, the fluid flows in either direction (i.e., from the tube 120 to the syringe or vice versa). In some embodiments, the fluid is under negative or positive pressure. In some embodiments, the needle holder 138 comprises a port lever or a collection tube configured to be received by the port 115. In some embodiments, the port 115 serves an opening to allow for the insertion of tubing into the device.

In some embodiments, the cartridge receiver 118 comprises a frame 146 having a rail on either of its sides. In some embodiments, the rail is configured to secure the needle holder 138. In some embodiments, the rail is configured to secure the cartridge 134. In some embodiments, the cartridge receiver 118 comprises a receiver opening 119. In some embodiments, the receiver opening 119 is configured to receive the cartridge 134 and the needle holder 138. In some embodiments, the receiver opening 119 has a rectangular shape, as shown in FIG. 2A. In some embodiments, the needle holder 138 fits within the receiver opening 119 once attached to the cartridge receiver 118.

Figure 3A:
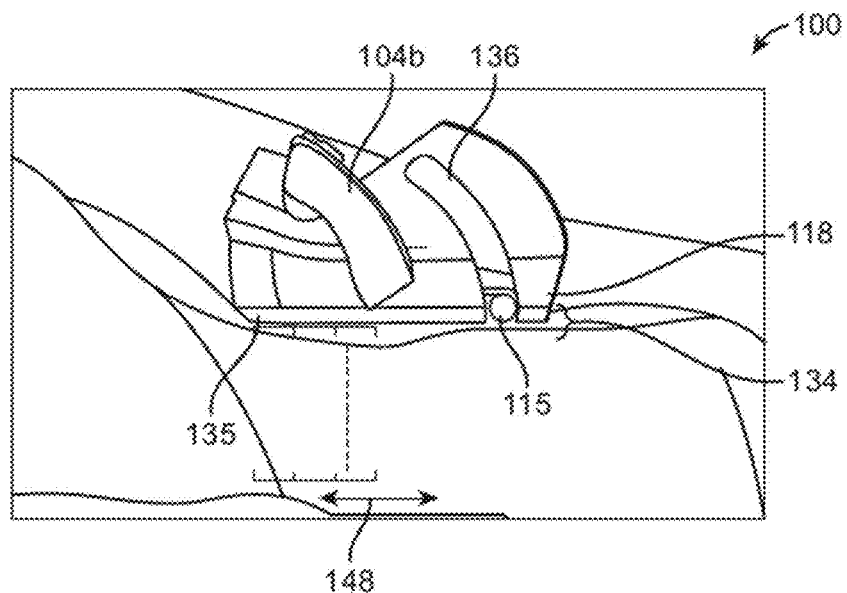
FIGS. 3A-B illustrate side views of an embodiment of the insertion device.

FIG. 3A shows the insertion device 100 positioned on the surface of the skin of a patient. In some embodiments, the needle holder angle 139, shown in FIG. 3B, s adjusted prior to injection. FIG. 3A shows a needle holder angle of about 0 degrees. In some embodiments, the position of the needle holder opening 160, as shown in FIG. 2A, is adjusted by the insertion device 100. FIG. 3A shows the direction of movement 148 of the needle holder 138 in this example. In some embodiments, the direction of movement 148 occurs from a proximal to a distal position, with respect to the patient and as depicted in FIG. 3A. In some embodiments, the direction of movement 148 occurs from a right lateral to a left lateral position, with respect to the patient. In some embodiments, the position of the needle, located within the cartridge 134, is adjusted and/or moved longitudinally by the insertion device 100. In some embodiments, the direction of movement 148 is the depth of the needle (i.e., in the z-plane). In some embodiments, the user is able to adjust the direction of movement 148 by using the interface of the insertion device 100.

Figure 3B:
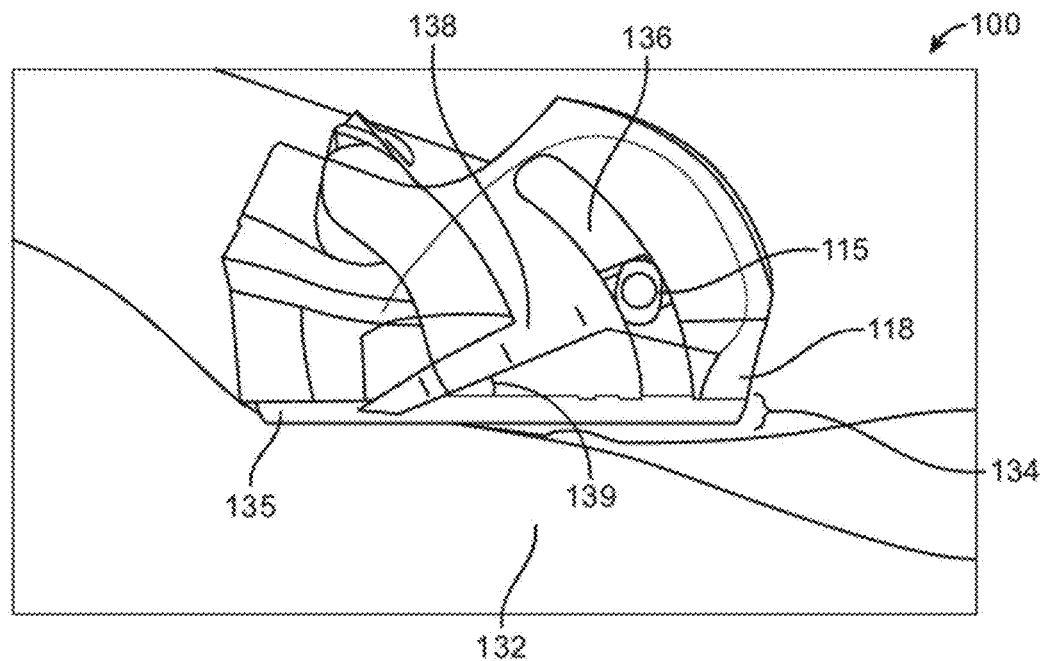

FIG. 3B shows the needle holder 138 at a needle holder angle 139 greater than about 0 degrees. In some embodiments, the needle holder angle 139 is adjusted based on the settings input by the user. In some embodiments, the needle holder angle 139 is the angle between the plate 135 and the bottom surface of the needle holder 138. In some embodiments, the plate 135 is placed directly above the surface of the skin of the patient 132 prior to insertion of the needle, as shown in FIG. 3B.

Figure 4A:
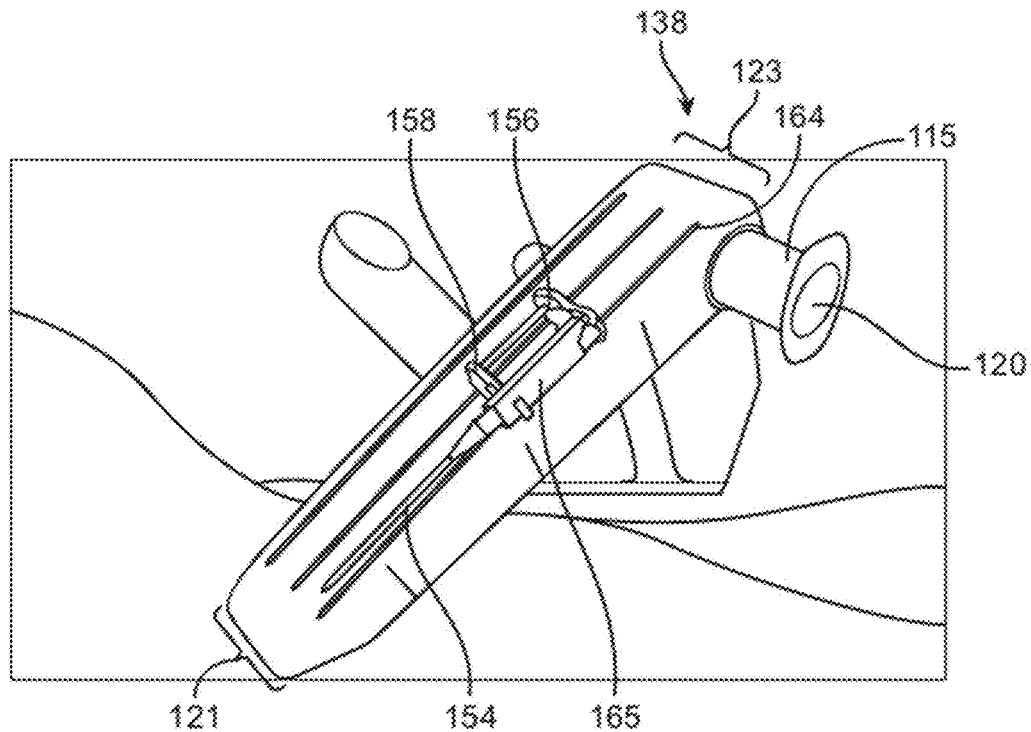
FIGS. 4A-D illustrate side views of an embodiment of a needle holder and the insertion of a catheter.

FIG. 4A shows an isometric view of the needle holder 138. In some embodiments, the needle holder 138 is composed of a metal and/or polymer material. In some embodiments, the needle holder 138 comprise a track 164, as shown in FIG. 4A. In some embodiments, the needle holder comprises one or more tracks. In some embodiments, the track 134 is configured to receive a needle. In some embodiments, the track 134 extends from the proximal end of the cartridge 123 to the distal end of the cartridge 121. In some embodiments, the track 134 is configured to receive a catheter. In some embodiments, the track 134 is configured to receive a syringe 165. In some embodiments, the track 134 is configured to receive tubing. In some embodiments, the needle holder 138 comprises prongs, magnets, clips, tabs, or any other suitable means for physically engaging the syringe and/or catheter. In some embodiments, the track 164 aligns a needle. In some embodiments, the syringe 165 sits on the track 134. In some embodiments, the syringe 165 is aligned with the track 134.

In some embodiments, the needle holder 138 comprises a catheter advancer 156. In some embodiments, the needle holder 138 comprises a needle advancer 158. In some embodiments, the catheter advancer 156 is operatively connected to one or more actuators of the insertion device 100. In some embodiments, the catheter advancer 156 is configured to move the position of the catheter (e.g., advance and/or retract the catheter along the track 134 and/or into the patient). In some embodiments, the needle advancer 158 is operatively connected to one or more actuators of the insertion device 100. In some embodiments, the needle advancer 158 is configured to move the position of the needle (e.g., advance and/or retract the needle and/or syringe along the track 134 and/or into the patient). In some embodiments, the user enacts the proper advancer using the user interface. In some embodiments, this enactment results in the insertion of the needle or catheter into the patient.

Figure 4B:
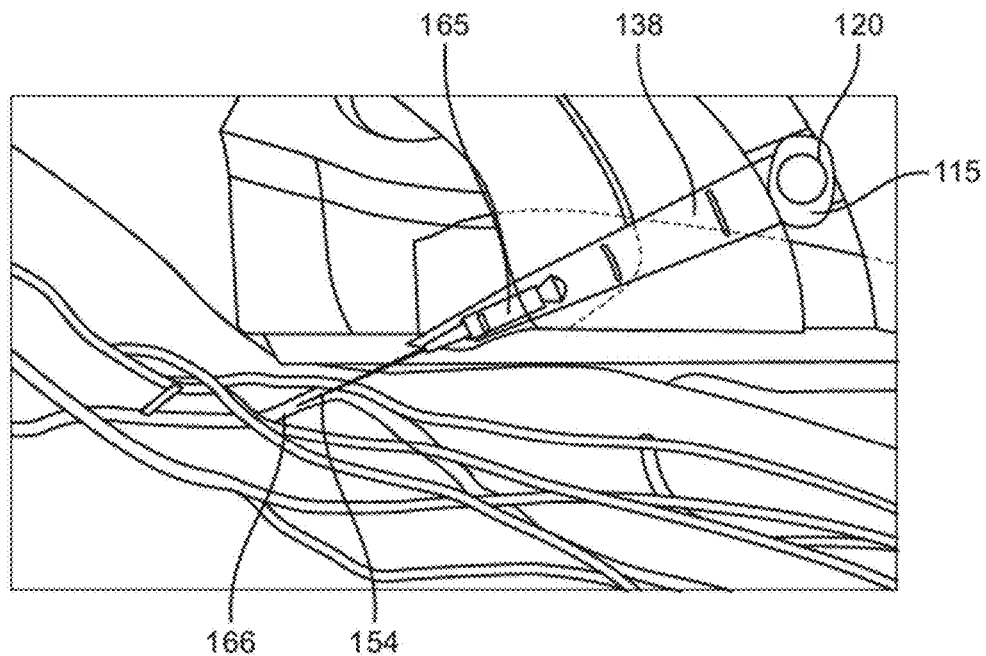
Figure 4C:
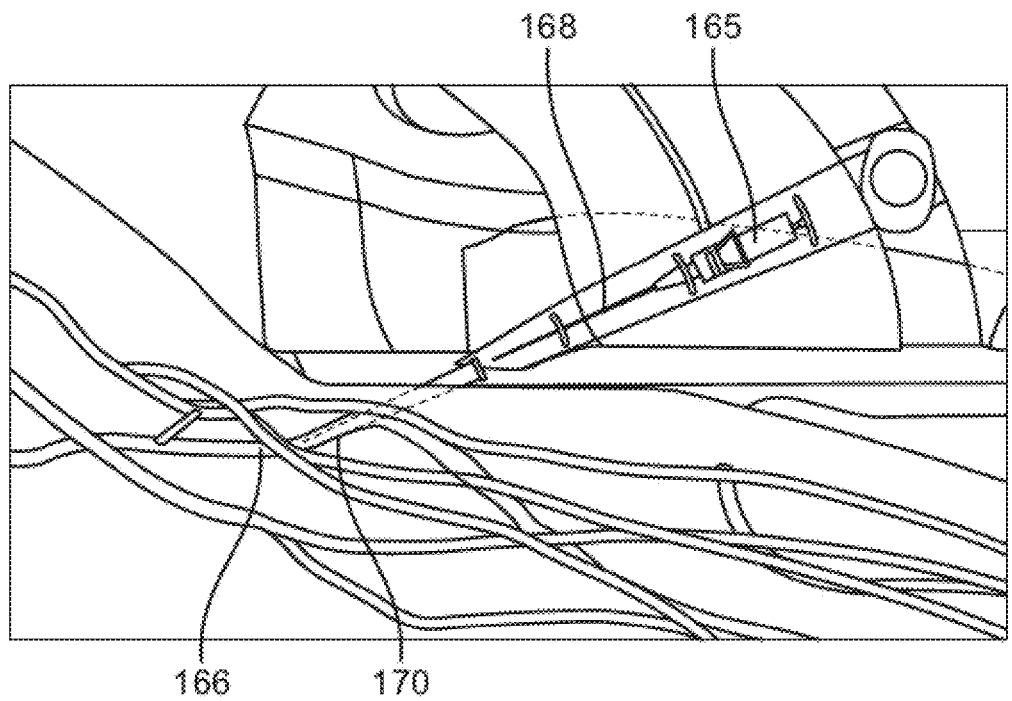
Figure 4D:
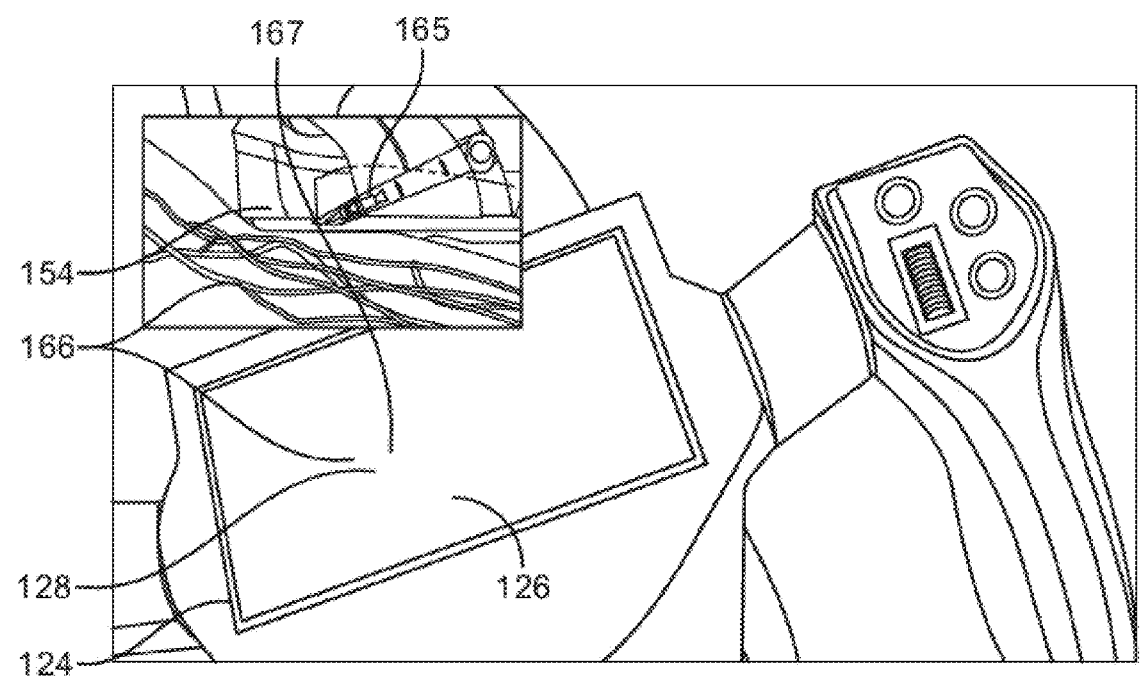

FIG. 4B shows the insertion device 100 deploying the syringe 165 and inserting the needle with a catheter 154 into a blood vessel 166 of the patient. FIG. 4C shows the catheter 170 deployed within the blood vessel 166 of the patient, and the needle 168 as it is retracted away from the catheter 170 and back into the needle holder 138. FIG. 4D shows the image 125 of the blood vessel 166 displayed on the display screen of the insertion device 100 as a catheter is being inserted into the blood vessel of the patient. In some embodiments, the image 125 comprises an indicator marking 128 and an indicator line 126, as shown in FIG. 4D. In some embodiments, the indicator marking 128 labels a needle insertion location prior to the needle being inserted. In some embodiments, the indicator marking 128 labels the needle location after the needle is inserted. In some embodiments, the indicator line 126 aligns with the indicator marking 128.

Figure 5:
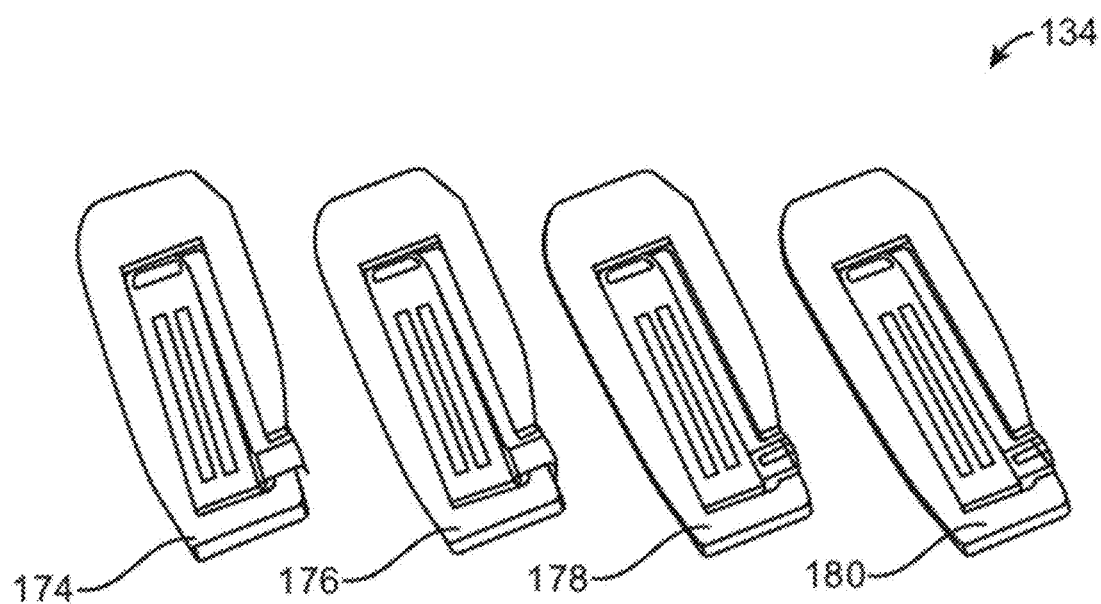
FIG. 5 illustrates various embodiments of cartridges that are used with an insertion device.

FIG. 5 shows various types of cartridges. In some embodiments, the cartridge 134 is loaded with a needle, catheter, and/or tubing necessary for a specific application (e.g., peripheral intravenous line or catheter placement) prior to being used and/or received by the user. In some embodiments, the cartridge is a peripheral intravenous site and phlebotomy cartridge 174. In some embodiments, the cartridge is a guidewire introducer cartridge 176 for peripherally inserted central catheter (PICC) lines and for central lines. In some embodiments, the cartridge is a targeted never and joint injection cartridge 178. In some embodiments, the cartridge is a tissue biopsy cartridge 180. In some embodiments, the different types of cartridges are easily differentiated from one another by the user. For example, in some embodiments, the different types of cartridges are labeled with different colors (i.e., the plates vary in color). In other embodiments, the different types of cartridges are clearly labeled with text indicating the type of cartridge and recommended use.

Figure 6:
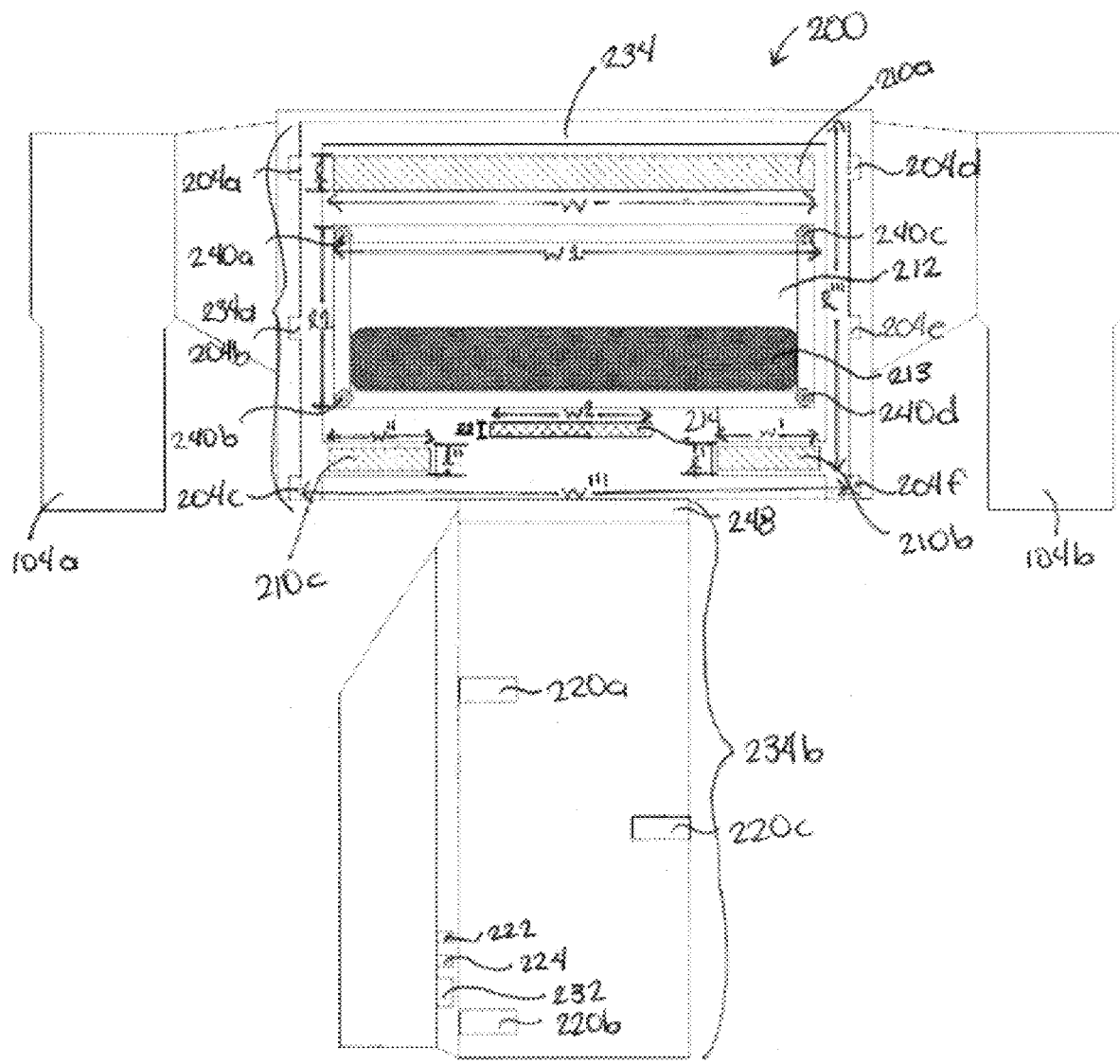
FIG. 6 illustrates a bottom view of another embodiment of the insertion device.

FIG. 6 shows a bottom view of another embodiment of the insertion device. An insertion device 200, as shown in FIG. 6, comprises a cartridge 234. In some embodiments, the cartridge 234 comprises a distal portion 234a and a proximal portion 234b, with respect to the user, as shown in FIG. 6. In some embodiments, the distal portion of the cartridge 234a sits in between the first handle 104a and the second handle 104b. In some embodiments, the distal portion of the cartridge 234a is reversibly attached to the insertion device. In some embodiments, the distal portion of the cartridge 234a is permanently attached to the insertion device. In some embodiments, the distal portion of the cartridge 234a is attached to the insertion device 200 via a first attachment locking point 204a, a second attachment locking point 204b, a third attachment locking point 204c, a fourth attachment locking point 204d, a fifth attachment locking point 204e, and a sixth attachment locking point 204f. In some embodiments, the attachment locking point is a tab. In some embodiments, the attachment locking point is a snap-on fixture. In some embodiments, the attachment locking point is a magnet.

In some embodiments, the distal portion of the cartridge 234a comprises a first suction area 210c, a second suction area 210b, and a third suction area 210c. In some embodiments, the first suction area 210a is located distally from the proximal portion of the cartridge 234b. In some embodiments, the first suction area 210a is located distally from the second suction area 210b and the third suction area 210c, as shown in FIG. 6. In some embodiments, the first suction area 210a is located distally from the second suction area 210b and the third suction area 210c, as shown in FIG. 6. Alternatively, in some embodiments, the second suction area 210b and the third suction area 210c are located distally from the first suction area 210a. In some embodiments, the first suction area 210a, the second suction area 210b, and the third suction area 210c are aligned along the length l''' of the distal portion of the cartridge 234a. In some embodiments, the first suction area 210a, the second suction area 210b, and the third suction area 210c are aligned along the width w''' of the distal portion of the cartridge 234a. In other embodiments, any other suitable arrangement of the first suction area 210a, the second suction area 210b, and the third suction area 210c is used.

In some embodiments, the first suction area 210a is larger in surface area than the second suction area 210b and the third suction area 210c, as shown in FIG. 6. Alternatively, in other embodiments, the surface area of the first suction area 210a is smaller than the surface area of the second suction area 210b and the third suction area 210c. In yet another embodiment, the surface areas of the first suction area 210a, the second suction area 210b, and the third suction area 210c are all about equal.

In some embodiments, the distal portion of the cartridge 234a has a rectangular shape having a length l''' and a width w''', as shown in FIG. 6. In some embodiments, the first suction area 210a has a rectangular shape having a length l and a width w, as shown in FIG. 6. In some embodiments, the width w of the first suction area 210a spans about 90% of the width w''' of the distal portion of the cartridge 234a. In some embodiments, the length l of the first suction area 210a is about 15% of the length l''' of the distal portion of the cartridge 234a. In some embodiments, the first suction area 210a is centered between the first attachment locking point 204a and the fourth attachment locking point 204d, as shown in FIG. 6. In some embodiments, the first suction area 210a has a circular shape, a triangular shape, a square shape, or any other suitable shape.

In some embodiments, the first suction area 210a has a width w ranging from about 0.5 inches (in.) to about 6 in. or more. In some embodiments, the first suction area 210a has a width w ranging from at least about 0.5 in. In some embodiments, the first suction area 210a has a width w ranging from at most about 6 in. In some embodiments, the first suction area 210a has a width w ranging from about 0.5 in. to about 1 in., about 0.5 in. to about 1.5 in., about 0.5 in. to about 2 in., about 0.5 in. to about 2.5 in., about 0.5 in. to about 3 in., about 0.5 in. to about 3.5 in., about 0.5 in. to about 4 in., about 0.5 in. to about 4.5 in., about 0.5 in. to about 5 in., about 0.5 in. to about 5.5 in., about 0.5 in. to about 6 in., about 1 in. to about 1.5 in., about 1 in. to about 2 in., about 1 in. to about 2.5 in., about 1 in. to about 3 in., about 1 in. to about 3.5 in., about 1 in. to about 4 in., about 1 in. to about 4.5 in., about 1 in. to about 5 in., about 1 in. to about 5.5 in., about 1 in. to about 6 in., about 1.5 in. to about 2 in., about 1.5 in. to about 2.5 in., about 1.5 in. to about 3 in., about 1.5 in. to about 3.5 in., about 1.5 in. to about 4 in., about 1.5 in. to about 4.5 in., about 1.5 in. to about 5 in., about 1.5 in. to about 5.5 in., about 1.5 in. to about 6 in., about 2 in. to about 2.5 in., about 2 in. to about 3 in., about 2 in. to about 3.5 in., about 2 in. to about 4 in., about 2 in. to about 4.5 in., about 2 in. to about 5 in., about 2 in. to about 5.5 in., about 2 in. to about 6 in., about 2.5 in. to about 3 in., about 2.5 in. to about 3.5 in., about 2.5 in. to about 4 in., about 2.5 in. to about 4.5 in., about 2.5 in. to about 5 in., about 2.5 in. to about 5.5 in., about 2.5 in. to about 6 in., about 3 in. to about 3.5 in., about 3 in. to about 4 in., about 3 in. to about 4.5 in., about 3 in. to about 5 in., about 3 in. to about 5.5 in., about 3 in. to about 6 in., about 3.5 in. to about 4 in., about 3.5 in. to about 4.5 in., about 3.5 in. to about 5 in., about 3.5 in. to about 5.5 in., about 3.5 in. to about 6 in., about 4 in. to about 4.5 in., about 4 in. to about 5 in., about 4 in. to about 5.5 in., about 4 in. to about 6 in., about 4.5 in. to about 5 in., about 4.5 in. to about 5.5 in., about 4.5 in. to about 6 in., about 5 in. to about 5.5 in., about 5 in. to about 6 in., or about 5.5 in. to about 6 in. In some embodiments, the first suction area 210a has a width w ranging from about 0.5 in., about 1 in., about 1.5 in., about 2 in., about 2.5 in., about 3 in., about 3.5 in., about 4 in., about 4.5 in., about 5 in., about 5.5 in., or about 6 in.

In some embodiments, the first suction area 210a has a length l ranging from about 0.25 in. to about 5.5 in. or more. In some embodiments, the first suction area 210a has a length l ranging from at least about 0.25 in. In some embodiments, the first suction area 210a has a length l ranging from at most about 5.5 in. In some embodiments, the first suction area 210a has a length l ranging from about 0.25 in. to about 0.5 in., about 0.25 in. to about 1 in., about 0.25 in. to about 1.5 in., about 0.25 in. to about 2 in., about 0.25 in. to about 2.5 in., about 0.25 in. to about 3 in., about 0.25 in. to about 3.5 in., about 0.25 in. to about 4 in., about 0.25 in. to about 4.5 in., about 0.25 in. to about 5 in., about 0.25 in. to about 5.5 in., about 0.5 in. to about 1 in., about 0.5 in. to about 1.5 in., about 0.5 in. to about 2 in., about 0.5 in. to about 2.5 in., about 0.5 in. to about 3 in., about 0.5 in. to about 3.5 in., about 0.5 in. to about 4 in., about 0.5 in. to about 4.5 in., about 0.5 in. to about 5 in., about 0.5 in. to about 5.5 in., about 1 in. to about 1.5 in., about 1 in. to about 2 in., about 1 in. to about 2.5 in., about 1 in. to about 3 in., about 1 in. to about 3.5 in., about 1 in. to about 4 in., about 1 in. to about 4.5 in., about 1 in. to about 5 in., about 1 in. to about 5.5 in., about 1.5 in. to about 2 in., about 1.5 in. to about 2.5 in., about 1.5 in. to about 3 in., about 1.5 in. to about 3.5 in., about 1.5 in. to about 4 in., about 1.5 in. to about 4.5 in., about 1.5 in. to about 5 in., about 1.5 in. to about 5.5 in., about 2 in. to about 2.5 in., about 2 in. to about 3 in., about 2 in. to about 3.5 in., about 2 in. to about 4 in., about 2 in. to about 4.5 in., about 2 in. to about 5 in., about 2 in. to about 5.5 in., about 2.5 in. to about 3 in., about 2.5 in. to about 3.5 in., about 2.5 in. to about 4 in., about 2.5 in. to about 4.5 in., about 2.5 in. to about 5 in., about 2.5 in. to about 5.5 in., about 3 in. to about 3.5 in., about 3 in. to about 4 in., about 3 in. to about 4.5 in., about 3 in. to about 5 in., about 3 in. to about 5.5 in., about 3.5 in. to about 4 in., about 3.5 in. to about 4.5 in., about 3.5 in. to about 5 in., about 3.5 in. to about 5.5 in., about 4 in. to about 4.5 in., about 4 in. to about 5 in., about 4 in. to about 5.5 in., about 4.5 in. to about 5 in., about 4.5 in. to about 5.5 in., or about 5 in. to about 5.5 in. In some embodiments, the first suction area 210a has a length l ranging from about 0.25 in., about 0.5 in., about 1 in., about 1.5 in., about 2 in., about 2.5 in., about 3 in., about 3.5 in., about 4 in., about 4.5 in., about 5 in., or about 5.5 in.

In some embodiments, the second suction area 210*b* has a rectangular shape having a length l''' and a width w'''. In some embodiments, the width of the second suction area 210*b* spans about 25% of the width w''' of the distal portion of the cartridge 234*a*. In some embodiments, the length l' of the second suction area 210*b* is about 10% of the length l''' of the distal portion of the cartridge 234*a*. In some embodiments, the second suction area 210*b* is located on a lateral region of the distal portion of the cartridge 234*a*, as shown in FIG. 6. In some embodiments, the second suction area 210*b* is adjacent to the third attachment locking point 204*c*, as shown in FIG. 6. In some embodiments, the second suction area 210*b* is located at the base of the distal portion of the cartridge 234*a*, as shown in FIG. 6. In some embodiments, the second suction area 210*b* is proximal to the sensor area 212, as shown in FIG. 6. In some embodiments, the second suction area 210*b* has a circular shape, a triangular shape, a square shape, or any other suitable shape.

In some embodiments, the second suction area 210*b* has a width w' ranging from about 0.1 in. to about 5 in. or more. In some embodiments, the second suction area 210*b* has a width w' ranging from at least about 0.1 in. In some embodiments, the second suction area 210*b* has a width w' ranging from at most about 5 in. In some embodiments, the second suction area 210*b* has a width w' ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the second suction area 210*b* has a width w' ranging from about 0.1 in., about 0.2 in., about 0.3 in., about 0.4 in., about 0.5 in., about 0.75 in., about 1 in., about 1.5 in., about 3 in., or about 5 in.

In some embodiments, the second suction area 210*b* has a length l' ranging from about 0.1 in. to about 5 in. or more. In some embodiments, the second suction area 210*b* has a length l' ranging from at least about 0.1 in. In some embodiments, the second suction area 210*b* has a length l' ranging from at most about 5 in. In some embodiments, the second suction area 210*b* has a length l' ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the second suction area 210*b* has a length l' ranging from about 0.1 in., about 0.2 in., about 0.3 in., about 0.4 in., about 0.5 in., about 0.75 in., about 1 in., about 1.5 in., about 3 in., or about 5 in.

In some embodiments, the third suction area 210*c* has a rectangular shape having a length l'' and a width w''. In some embodiments, the width of the third suction area 210*c* spans about 25% of the width w''' of the distal portion of the cartridge 234*a*. In some embodiments, the length l'' of the third suction area 210*c* is about 10% of the length l''' of the distal portion of the cartridge 234*a*. In some embodiments, the third suction area 210*c* is located on a lateral region of the distal portion of the cartridge 234*a*, as shown in FIG. 6. In some embodiments, the third suction area 210*c* is adjacent to the sixth attachment locking point 204*f*, as shown in FIG. 6. In some embodiments, the third suction area 210*c* is located at the base of the distal portion of the cartridge 234*a*, as shown in FIG. 6. In some embodiments, the third suction area 210*c* is proximal to the sensor area 212, as shown in FIG. 6. In some embodiments, the third suction area 210*c* has a circular shape, a triangular shape, a square shape, or any other suitable shape.

In some embodiments, the third suction area 210*c* has a width w'' ranging from about 0.1 in. to about 5 in. or more. In some embodiments, the third suction area 210*c* has a width w'' ranging from at least about 0.1 in. In some embodiments, the third suction area 210*c* has a width w'' ranging from at most about 5 in. In some embodiments, the third suction area 210*c* has a width w'' ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the third suction area 210c has a width w" ranging from about 0.1 in., about 0.2 in., about 0.3 in., about 0.4 in., about 0.5 in., about 0.75 in., about 1 in., about 1.5 in., about 3 in., or about 5 in.

In some embodiments, the third suction area 210c has a length l" ranging from about 0.1 in. to about 5 in. or more. In some embodiments, the third suction area 210c has a length l" ranging from at least about 0.1 in. In some embodiments, the third suction area 210c has a length l" ranging from at most about 5 in. In some embodiments, the third suction area 210c has a length l" ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the third suction area 210c has a length l" ranging from about 0.1 in., about 0.2 in., about 0.3 in., about 0.4 in., about 0.5 in., about 0.75 in., about 1 in., about 1.5 in., about 3 in., or about 5 in.

In some embodiments, the distal portion of the cartridge 234a comprises a sensor area 212. In some embodiments, the sensor area 212 has a rectangular shape having a length l1 and a width w1, as shown in FIG. 6. In some embodiments, the width w1 of the sensor area 212 spans about 90% of the width w''' of the distal portion of the cartridge 234a. In some embodiments, the length l1 of the sensor area 212 is about 50% of the length l''' of the distal portion of the cartridge 234a. In some embodiments, the distal portion of the cartridge 234a comprises one or more sensor areas. For example, in some embodiments, the distal portion of the cartridge 234a comprises two, three, four, five, six, seven, eight, nine, ten, or more sensor areas. In some embodiments, the sensor area 212 comprises an ultrasound sensor area. In some embodiments, the ultrasound sensor area is the surface area of an ultrasound transducer. In some embodiments, the sensor area 212 comprises an ultrasound transducer 213. Alternatively, in some embodiments, the sensor area 212 does not comprise an ultrasound transducer 213. In some embodiments, the ultrasound transducer 213 is located within the housing of the insertion device. In some embodiments, the cartridge 234 does not comprise the ultrasound transducer 213. In some embodiments, the sensor area 212 is an area that allows for the transmission of ultrasound waves. In some embodiments, the body of the ultrasound transducer 213 is located within the housing. In some embodiments, the ultrasound transducer 213 occupies the entire sensor area 212. In some embodiments, the ultrasound transducer 213 occupies a part of the sensor area 212.

In some embodiments, the sensor area 212 does not comprise an infrared sensor. In some embodiments, the infrared sensor is located within the housing of the insertion device. In some embodiments, the cartridge 234 does not comprise infrared sensor. In some embodiments, the sensor area 212 is an area that allows for the transmission of infrared wavelengths and/or wavelengths within the visible light spectrum. Alternatively, in some embodiments, the sensor area 212 comprises an infrared sensor area. In some embodiments, the sensor area comprises a first infrared sensor 240a, a second infrared sensor 240b, a third infrared sensor 240c, and a fourth infrared sensor 240d. In some embodiments, the sensor area 212 comprises five or more infrared sensors. For example, in some embodiments, the sensor area 212 comprises six, seven, eight, nine, ten, eleven, twelve, thirteen, fourteen, fifteen, or more infrared sensors. In some embodiments, the first infrared sensor 240a, the second infrared sensor 240b, the third infrared sensor 240c, and the fourth infrared sensor 240d are each located in a corner of the sensor area 212, as shown in FIG. 6. In some embodiments, the infrared sensors are located throughout the surface of the distal portion of the cartridge 234a. In some embodiments, the first infrared sensor 240a, the second infrared sensor 240b, the third infrared sensor 240c, and the fourth infrared sensor 240d are each located in a corner of the distal portion of the cartridge 234a. In some embodiments, the first infrared sensor 240a, the second infrared sensor 240b, the third infrared sensor 240c, and the fourth infrared sensor 240d are each located adjacent to an attachment locking point in the distal portion of the cartridge 234a.

In some embodiments, the sensor area 212 comprises a thermoelectric cooling and vibration area 214. In some embodiments, the thermoelectric cooling and vibration area 214 has a rectangular shape having a length l2 and a width w2, as shown in FIG. 6. In some embodiments, the width w2 of the thermoelectric cooling and vibration area 214 spans about 5% of the width w''' of the distal portion of the cartridge 234a. In some embodiments, the length l2 of the sensor area 212 is about 25% of the length l''' of the distal portion of the cartridge 234a. In some embodiments, the thermoelectric cooling and vibration area 214 comprises a thermoelectric cooler. In some embodiments, the thermoelectric cooling and vibration area 214 comprises a vibrator. In some embodiments, the thermoelectric cooling and vibration area 214 has a rectangular shape, as shown in FIG. 6. In some embodiments, the thermoelectric cooling and vibration area 214 has a circular shape, a triangular shape, a square shape, or any other suitable shape. In some embodiments, the thermoelectric cooling and vibration area 214 is located at the base of the distal portion of the cartridge 234a, as shown in FIG. 6. In some embodiments, the thermoelectric cooling and vibration area 214 is located between the second suction area 210b and the third suction area 210c. In some embodiments, the thermoelectric cooling and vibration area 214 is located adjacent to the sensor area 212. In some embodiments, the thermoelectric cooling and vibration area 214 is located adjacent to the ultrasound transducer 213. In some embodiments, the distal portion of the cartridge 234a comprises one or more thermoelectric cooling and vibration areas. For example, in some embodiments, the distal portion of the cartridge 234a comprises two, three, four, five, six, seven, eight, nine, ten, or more thermoelectric cooling and vibration areas.

In some embodiments, the thermoelectric cooling and vibration area 214 has a width w2 ranging from about 0.1 in. to about 5 in. or more. In some embodiments, the thermoelectric cooling and vibration area 214 has a width w2 ranging from at least about 0.1 in. In some embodiments, the thermoelectric cooling and vibration area 214 has a width w2 ranging from at most about 5 in. In some embodiments, the thermoelectric cooling and vibration area 214 has a width w2 ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the thermoelectric cooling and vibration area 214 has a width w2 ranging from about 0.1 in., about 0.2 in., about 0.3 in., about 0.4 in., about 0.5 in., about 0.75 in., about 1 in., about 1.5 in., about 3 in., or about 5 in.

In some embodiments, the thermoelectric cooling and vibration area 214 has a length l2 ranging from about 0.1 in. to about 5 in. or more. In some embodiments, the thermoelectric cooling and vibration area 214 has a length l2 ranging from at least about 0.1 in. In some embodiments, the thermoelectric cooling and vibration area 214 has a length l2 ranging from at most about 5 in. In some embodiments, the thermoelectric cooling and vibration area 214 has a length l2 ranging from about 0.1 in. to about 0.2 in., about 0.1 in. to about 0.3 in., about 0.1 in. to about 0.4 in., about 0.1 in. to about 0.5 in., about 0.1 in. to about 0.75 in., about 0.1 in. to about 1 in., about 0.1 in. to about 1.5 in., about 0.1 in. to about 3 in., about 0.1 in. to about 5 in., about 0.2 in. to about 0.3 in., about 0.2 in. to about 0.4 in., about 0.2 in. to about 0.5 in., about 0.2 in. to about 0.75 in., about 0.2 in. to about 1 in., about 0.2 in. to about 1.5 in., about 0.2 in. to about 3 in., about 0.2 in. to about 5 in., about 0.3 in. to about 0.4 in., about 0.3 in. to about 0.5 in., about 0.3 in. to about 0.75 in., about 0.3 in. to about 1 in., about 0.3 in. to about 1.5 in., about 0.3 in. to about 3 in., about 0.3 in. to about 5 in., about 0.4 in. to about 0.5 in., about 0.4 in. to about 0.75 in., about 0.4 in. to about 1 in., about 0.4 in. to about 1.5 in., about 0.4 in. to about 3 in., about 0.4 in. to about 5 in., about 0.5 in. to about 0.75 in., about 0.5 in. to about 1 in., about 0.5 in. to about 1.5 in., about 0.5 in. to about 3 in., about 0.5 in. to about 5 in., about 0.75 in. to about 1 in., about 0.75 in. to about 1.5 in., about 0.75 in. to about 3 in., about 0.75 in. to about 5 in., about 1 in. to about 1.5 in., about 1 in. to about 3 in., about 1 in. to about 5 in., about 1.5 in. to about 3 in., about 1.5 in. to about 5 in., or about 3 in. to about 5 in. In some embodiments, the thermoelectric cooling and vibration area 214 has a length l2 ranging from about 0.1 in., about 0.2 in., about 0.3 in., about 0.4 in., about 0.5 in., about 0.75 in., about 1 in., about 1.5 in., about 3 in., or about 5 in.

In some embodiments, the cartridge 234 comprises a proximal portion 234b, with respect to the user when operating the insertion device. In some embodiments, the proximal portion of the cartridge 234b comprises a first attachment point 220a, a second attachment point 220b, and a third attachment point 220c. In some embodiments, the proximal portion of the cartridge 234b is reversibly attached to the insertion device. In some embodiments, the proximal portion of the cartridge 234b is permanently attached to the insertion device. In some embodiments, the proximal portion of the cartridge 234b is attached to the insertion device 200 via the first attachment point 220a, the second attachment point 220b, and the third attachment point 220c. In some embodiments, the attachment point is a tab that inserts into an opening of the housing. In some embodiments, the attachment point is a snap-on notch. In some embodiments, the user inserts the proximal portion of the cartridge 234b into the into the snap-on notch by pushing the proximal portion of the cartridge 234b into the snap-on notch, with a light force so that the body of the proximal portion of the cartridge 234b overcomes the projections of the snap-on notch. In some embodiments, the user releases the proximal portion of the cartridge 234b, by pulling on its proximal end, with a light force so that the body of the proximal portion of the cartridge 234b passes the projections of the snap-on notch. In some embodiments, the attachment point is a magnet. In some embodiments, the proximal portion of the cartridge 234b comprises a magnet. In some embodiments, the magnet of the proximal portion of the cartridge 234b and the magnet of the attachment point engage together magnetically (e.g., via a magnetic attraction). In some embodiments, the attachment point is a prong that inserts into an opening of the housing.

In some embodiments, the proximal portion of the cartridge 234b is reversibly attached to the distal portion of the cartridge 234a. In some embodiments, the proximal portion of the cartridge 234b comprises a collar 248. In some embodiments, the collar 248 connects the proximal portion of the cartridge 234b and the distal portion of the cartridge 234a. In some embodiments, the collar 248 comprises one or more tabs that insert into an opening in the proximal portion of the cartridge 234a. In some embodiments, the distal portion of the cartridge 234a comprises one or more snap-on notches. In some embodiments, the user inserts the collar 248 into the into the snap-on notch by pushing the proximal portion of the cartridge 234b into the snap-on notch, with a light force so that the collar 248 overcomes the projections of the snap-on notch. In some embodiments, the user releases the proximal portion of the cartridge 234b, by pulling on its proximal end, with a light force so that the collar 248 passes the projections of the snap-on notch. In some embodiments, the distal portion of the cartridge 234a comprises a magnet located at its base. In some embodiments, the collar 248 comprises a magnet. In some embodiments, the collar 248 is magnetized. In some embodiments, the magnet of the distal portion of the cartridge 234a and the magnet of the collar 248 engage together magnetically (e.g., via a magnetic attraction). In some embodiments, the collar 248 comprises one or more prongs that insert into an opening of the distal portion of the cartridge 234a.

In some embodiments, the collar 248 is a flexible collar. In some embodiments, the collar 248 is composed of an elastic, pliant, supple, or yielding material. In some embodiments, the collar 248 is composed of a flexible material. In some embodiments, the flexible material is polymeric material. In some embodiments, the flexible material is an elastomer. In some embodiments, the flexible material is rubber. In some embodiments, the flexible material is silicone. Non-limiting examples of the flexible material include polyurethanes, urethanes, silicone resins, foam rubber, polysiloxane, saturated rubbers, thermoplastic elastomers, elastolefin, and unsaturated rubbers. In some embodiments, the collar 248 is in a compressed state. In some embodiments, the collar 248 is in an extended state (i.e., the length of the collar 248 in the extended state is greater than the length of the collar 248 in the compressed state). In some embodiments, the user controls the length of the collar 248 by pushing and/or pulling on the proximal portion of the cartridge 234b with a light force.

In some embodiments, the proximal portion of the cartridge 234b comprises a catheter controlling needle slot 222. In some embodiments, the catheter-controlling slot 222 is an example of a female control slot that controls the advancement and/or retraction of a catheter over the needle in a proximal and/or a distal direction. In some embodiments, the insertion device comprises a corresponding catheter-controlling male connector (not shown in FIGS. 1-12) that is configured to insert into the catheter-controlling slot 222 once the cartridge 234 is connected to the insertion device. In some embodiments, the insertion device comprises an actuator that detects the location of the catheter-controlling slot 222 and/or its corresponding catheter-controlling male connector. In some embodiments, the insertion device comprises an actuator that advances the catheter-controlling male connector and subsequently advances the female catheter-controlling slot 222 to a proximal and/or a distal location, in a linear motion. In some embodiments, the cartridge 234 comprises a flexible portion of material in the proximal and distal location of the catheter-controlling slot 222 that has a spring-like action. In some embodiments, this flexible portion of material resists movement of the catheter-controlling slot 222. In some embodiments, when the catheter-controlling slot 222 and its corresponding catheter-controlling slot 222 are disconnected, the flexible portions of material, in the proximal and distal locations of the catheter-controlling slot 222, exert a force on the catheter-controlling slot 222 such that it retracts and returns to its initial position.

In some embodiments, the proximal portion of the cartridge 234b comprises a needle-controlling slot 224. In some embodiments, the needle-controlling slot 224 is an example of a female control slot that controls the advancement and/or retraction of a needle in a proximal and/or a distal direction. In some embodiments, the insertion device comprises a corresponding needle-controlling male connector (not shown in FIGS. 1-12) that is configured to insert into the needle-controlling slot 224 once the cartridge 234 is connected to the insertion device. In some embodiments, the insertion device comprises an actuator that detects the location of the needle-controlling slot 224 and/or its corresponding needle-controlling male connector. In some embodiments, the insertion device comprises an actuator that advances the needle-controlling male connector and subsequently advances the female needle-controlling slot 224 to a proximal and/or a distal location, in a linear motion.

In some embodiments, the proximal portion of the cartridge 234b comprises a guidewire-controlling slot 232. In some embodiments, the guidewire-controlling needle slot 232 is an example of a female control slot that controls the advancement and/or retraction of a guidewire in a proximal and/or a distal direction. In some embodiments, the guidewire-controlling needle slot 232 is hexagonal in shape. In some embodiments, the guidewire-controlling needle slot 232 is connected to a guidewire-containing spindle (not shown in FIGS. 1-12). In some embodiments, the guidewire rests within the insertion device and in the guidewire-containing spindle. In some embodiments, the guidewire-containing spindle and the distal end of the guidewire rest inside the needle. In some embodiments, the guidewire is held in its resting position by a spiral torsion spring (not shown in FIGS. 1-12). In some embodiments, the guidewire-controlling needle slot 232 moves rotationally. In some embodiments, the guidewire-controlling needle slot 232 acts against or with the force of the spiral torsion spring and advances or retracts the guidewire within the needle. In some embodiments, the guidewire is advanced out of the distal end of the needle such that it is advanced flexibly down the target tissue (e.g., a lumen of a target blood vessel) after the needle has already been inserted into the target tissue (e.g., a target blood vessel). In some embodiments, once the distal end of the guidewire is advanced into the target tissue (e.g., the lumen of the target blood vessel), the catheter is advanced forward over the needle and over the guidewire into the target tissue (e.g., the lumen of the blood vessel). In some embodiments, the introduction of a needle, a catheter, and/or a guidewire using the devices, methods, and systems described herein is consistent with the Seldinger technique. The Seldinger technique is a medical procedure used to obtain safe access to blood vessels and/or hollow organs. In some embodiments, the devices, methods, and systems described herein improve the success of insertion of a needle, a catheter, and/or a guidewire into the lumen of a target tissue (e.g., a blood vessel and/or a hollow organ). In some embodiments, the devices, methods, and systems described herein decrease the risk of insertion of a needle, a catheter, and/or a guidewire into a false lumen of a target tissue (e.g., a blood vessel and/or a hollow organ).

In some embodiments, the insertion device comprises a corresponding guidewire-controlling male connector (not shown in FIGS. 1-12) that is configured to insert into the guidewire-controlling slot 232 once the cartridge 234 is connected to the insertion device. In some embodiments, the guidewire-controlling male connector is hexagonal in shape. In some embodiments, the insertion device comprises an actuator that detects the location of the guidewire-controlling slot 232 and/or its corresponding guidewire-controlling male connector. In some embodiments, the insertion device comprises an actuator that advances the guidewire-controlling male connector and subsequently advances the female guidewire-controlling slot 232 to a proximal and/or a distal location, in a linear motion. In some embodiments, the actuator is a rotational actuator.

In some embodiments, the catheter-controlling slot 222 is located on a lateral face of the proximal portion of the cartridge 234b, as shown in FIG. 6. In some embodiments, the catheter-controlling slot 222 is located on a frontal face of the proximal portion of the cartridge 234b. In some embodiments, the catheter-controlling slot 222 is located on a rear face of the proximal portion of the cartridge 234b.

In some embodiments, the needle-controlling slot 224 is located on a lateral face of the proximal portion of the cartridge 234b, as shown in FIG. 6. In some embodiments, the needle-controlling slot 224 is located on a frontal face of the proximal portion of the cartridge 234b. In some embodiments, the needle-controlling slot 224 is located on a rear face of the proximal portion of the cartridge 234b.

In some embodiments, the guidewire-controlling slot 232 is located on a lateral face of the proximal portion of the cartridge 234b, as shown in FIG. 6. In some embodiments, the guidewire-controlling slot 232 is located on a frontal face of the proximal portion of the cartridge 234b. In some embodiments, the guidewire-controlling slot 232 is located on a rear face of the proximal portion of the cartridge 234b.

In some embodiments, the catheter-controlling slot 222 is adjacent to the needle-controlling slot 224 and/or to the guidewire-controlling slot 232. In some embodiments, the needle-controlling slot 224 is adjacent to the catheter-controlling slot 222 and/or to the guidewire-controlling slot 232. In some embodiments, the guidewire-controlling slot 232 is adjacent to the needle-controlling slot 224 and/or to the catheter-controlling slot 222.

Figure 7:
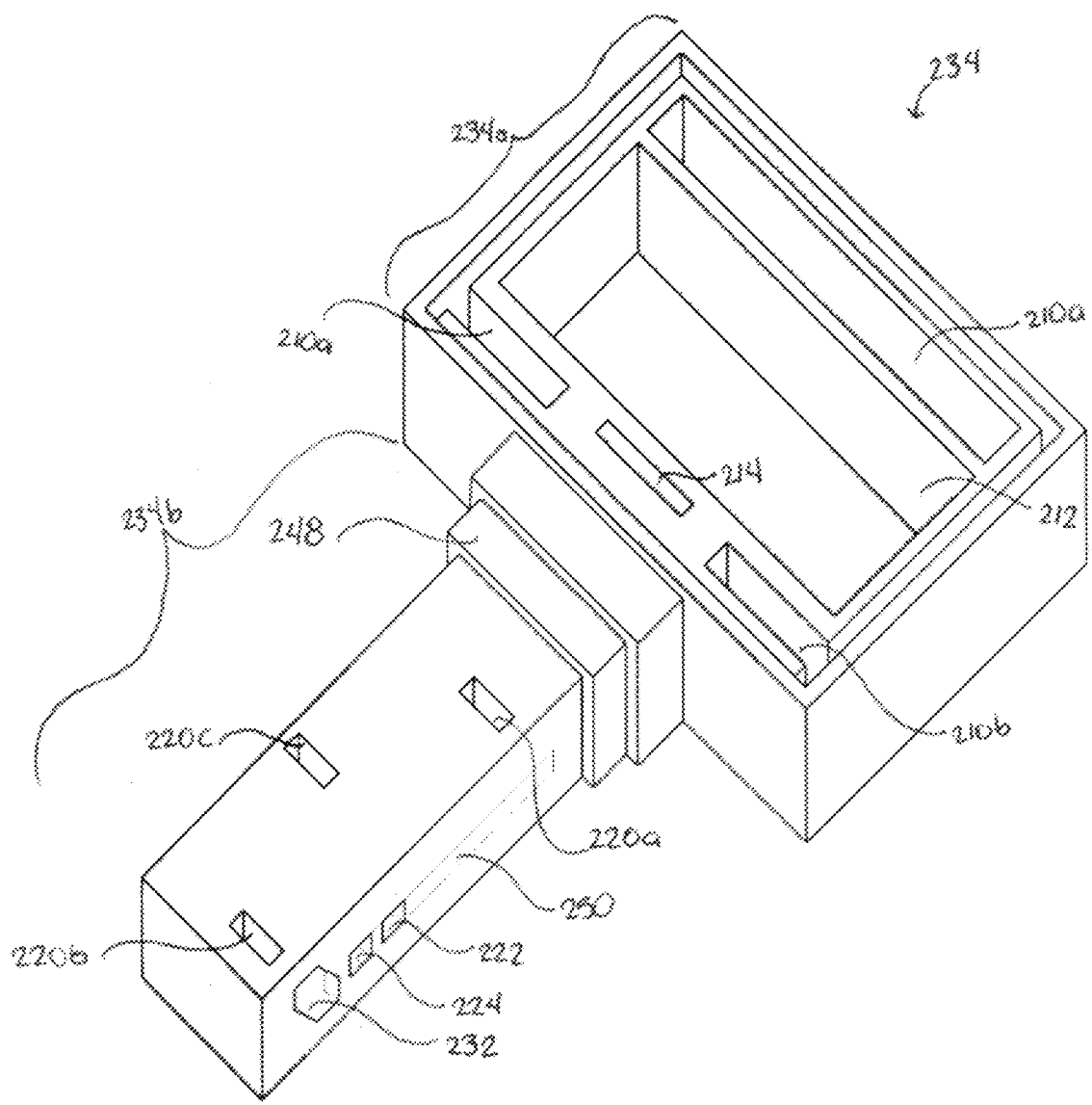
FIG. 7 illustrates an isometric view of an embodiment of a cartridge of the insertion device.

FIG. 7 shows a perspective representation of an embodiment of the cartridge 234 of the insertion device. In some embodiments, the proximal portion of the cartridge 234b comprises a cartridge slit 250. In some embodiments, the cartridge slit 250 is an opening configured to receive the catheter-controlling slot 222 and the needle-controlling slot 224. In some embodiments, the cartridge slit 250 is a track configured to guide the catheter-controlling slot 222 and the needle-controlling slot 224. In some embodiments, the cartridge slit 250 comprises a flexible material. In some embodiments, the cartridge slit 250 is a linear slot or opening located on a lateral side of the proximal portion of the cartridge 234b, as shown in FIG. 7. In some embodiments, the cartridge slit 250 allows for a linear movement of the catheter-controlling slot 222 and the needle-controlling slot 224. In some embodiments, the cartridge slit 250 allows proximal and distal movement of the catheter-controlling slot 222 and the needle-controlling slot 224. In some embodiments, the flexible material located in the cartridge slit 250 provides a spring-type force that acts to keep the catheter-controlling slot 222 and the needle-controlling slot 224 in their resting positions. In some embodiments, the flexible material located in the cartridge slit 250 pushes the catheter-controlling slot 222 and the needle-controlling slot 224 to their resting positions when the cartridge 234 is disconnected from the insertion device 200.

Figure 8:
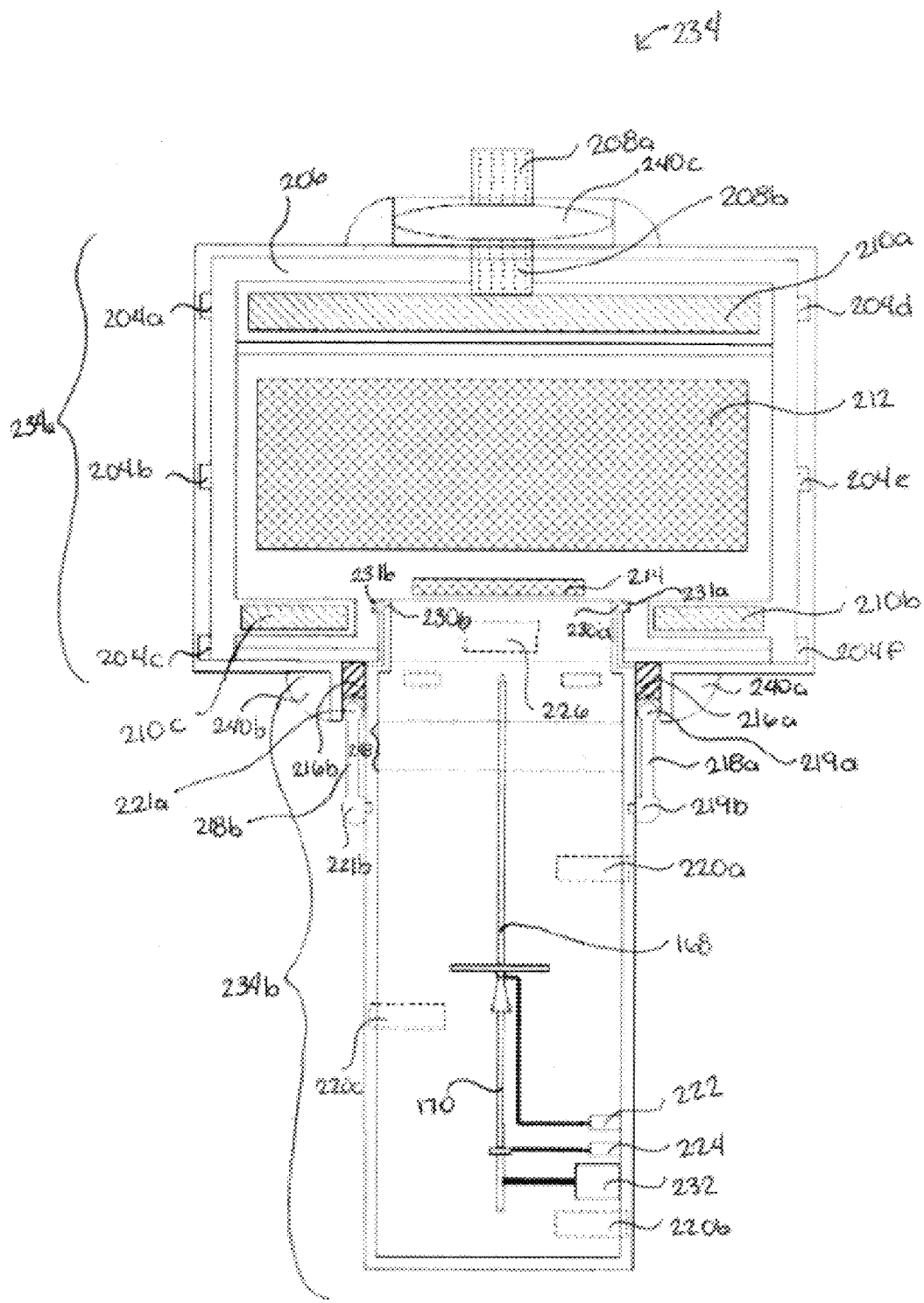
FIG. 8 illustrates a bottom view of an embodiment of a cartridge of the insertion device.

FIG. 8 illustrates a bottom view of an embodiment of the cartridge 234 of the insertion device. In some embodiments, the cartridge 234 comprises a first control arm 218a and a second control arm 218b. In some embodiments, the first control arm 218a and a second control arm 218b comprise at least one ball joint. In some embodiments, the ball joint comprises a bearing stud and a socket (not shown in FIG. 8) enclosed in a casing. In some embodiments, the first control arm 218a and a second control arm 218b control the movement and/or angle of the proximal portion of the cartridge 234b. In some embodiments, the first control arm 218a and a second control arm 218b are operatively connected to an actuator of the insertion device.

In some embodiments, the first control arm 218a comprises a proximal ball joint 219b and a distal ball joint 219a. In some embodiments, the proximal ball joint 219b of the first control arm 218a is attached to a lateral face of the proximal portion of the cartridge 234b, as shown in FIG. 8. In some embodiments, the distal ball joint 219a of the first control arm 218a connects to a first collar spring 216a. In some embodiments, the first collar spring 216a is located at the base of the distal portion of the cartridge 234a and adjacent to the proximal portion of the cartridge 234b. In some embodiments, the first collar spring 216a is enclosed in a casing.

In some embodiments, the second control arm 218b comprises a proximal ball joint 221b and a distal ball joint 221a. In some embodiments, the proximal ball joint 221b of the second control arm 218b is attached to a lateral face of the proximal portion of the cartridge 234b that is opposite to the lateral side comprising the first ball joint 218a, as shown in FIG. 8. For example, in some embodiments, the first control arm 218a is located on the right side of the proximal portion of the cartridge 234b and the second control arm 218b is located on the left side of the proximal portion of the cartridge 234b, as shown in FIG. 8. In some embodiments, the distal ball joint 221a of the second control arm 218b connects to a second collar spring 216b. In some embodiments, the second collar spring 216b is located at the base of the distal portion of the cartridge 234a and adjacent to the proximal portion of the cartridge 234b. In some embodiments, the second collar spring 216b is enclosed in a casing.

In some embodiments, the first control arm 218a and the second control arm 218b allow for simultaneous free rotation in two planes while preventing translation in any direction. In some embodiments, the first control arm 218a and the second control arm 218b allow for a degree of rotation in movement of the proximal portion of the cartridge 234b with respect to the distal portion of the cartridge 234a.

In some embodiments, the proximal portion of the cartridge 234b comprises a first arm 230a and a second arm 230b, as shown in FIG. 8. In some embodiments, the distal portion of the cartridge 234a comprises a first notch 231a and a second notch 231b, as shown in FIG. 8. In some embodiments, the first notch 213a is configured to receive the first arm 230a. In some embodiments, the second notch 213b is configured to receive the second arm 230b. In some embodiments, the first arm 230a and the second arm 230b are flexible. In some embodiments, the first arm 230a and the second arm 230b are configured to bend. In some embodiments, the user inserts the proximal portion of the cartridge 234b into the distal portion of the cartridge 234a by pushing the proximal portion of the cartridge 234b with a light force so that the first arm 230a and the second arm 230b overcome the projections of the first notch 231a and the second notch 231b. In some embodiments, the user releases the proximal portion of the cartridge 234b, by pulling on its proximal end, with a light force so that the first arm 230a and the second arm 230b pass the projections of the first notch 231a and the second notch 231b.

In some embodiments, the cartridge 234 comprises one or more suction valves. In some embodiments, the cartridge 234 comprises a first suction valve 208a and a second suction valve 208b, as shown in FIG. 8. In some embodiments, the first suction valve 208a and a suction valve 208b are one-way valves. In some embodiments, the suction valve is controlled manually.

In some embodiments, manual control of the vacuum action of the cartridge is controlled by the user.

In some embodiments, the cartridge 234 comprises a vacuum button or a vacuum bulb (not shown in FIGS. 1-12). In some embodiments, the surface of the vacuum button or the vacuum bulb is a pliable membrane. In some embodiments, the pliable membrane is composed of a shape-memory polymer. In some embodiments, the user activates the vacuum button and/or the vacuum bulb to activate the suction. In some embodiments, the vacuum button is a flexible, dome-shaped button. In some embodiments, the vacuum bulb is a flexible bulb. In some embodiments, the user depresses the vacuum button or the vacuum bulb to initiate suction. In some embodiments, once depressed, the area under the vacuum button is decreased thereby displacing the air under its surface (e.g., a membrane), which pushes that air through the first suction valve 208a to outside of the outer edge of the cartridge 234. In some embodiments, once the pressure exerted by the user onto the surface of the vacuum button and/or vacuum bulb is the released, the vacuum button and/or vacuum bulb returns to its original shape, creates an area of low pressure under the vacuum button and/or vacuum bulb, and consequently draws air through the second suction valve 208b from the suction area under the cartridge, between the cartridge and the surface of the skin of the patient.

Alternatively, in some embodiments, the cartridge comprises a manually controlled centrifugal pump. In some embodiments, the centrifugal pump comprises an impeller. In some embodiments, the user mechanically activates the impeller by depressing a button. In some embodiments, the depression of the button causes a rotation of the impeller to start. In some embodiments, the rotation of the impeller pushes air out of the first suction valve 208a to outside of the cartridge, thereby creating an area of low pressure in an impeller chamber. In some embodiments, the low pressure draws air through the second suction valve 208b from the suction area under the cartridge, between the cartridge and the surface of the skin of the patient.

Alternatively, in yet another embodiment, the vacuum button and/or the vacuum bulb is automatically activated by the insertion device. In some embodiments, an actuator of the insertion device causes the depression of the vacuum button and/or the vacuum bulb on the cartridge.

Alternatively, in other cases, the vacuum between the surface of the skin and the cartridge is created by a vacuum pump located within the housing of the insertion device.

In some embodiments, the first suction valve 208a and a suction valve 208b are operatively connected to a vacuum source (not shown in FIG. 8). In some embodiments, the first suction valve 208a and the second suction valve 208b are in fluid communication with a vacuum source (not shown in FIG. 8). In some embodiments, the first suction valve 208a and the second suction valve 208b are controlled automatically by the insertion device.

In some embodiments, the first suction valve 208a and the second suction valve 208b are located at the distal end of the distal portion of the cartridge 234a, as shown in FIG. 8. Alternatively, in some embodiments, the first suction valve 208a and the second suction valve 208b are located at the proximal end of the distal portion of the cartridge 234a. In other cases, the first suction valve 208a and the second suction valve 208b are located at the lateral ends of the distal portion of the cartridge 234a.

In some embodiments, the proximal portion of the cartridge 234b comprises a first infrared sensor 240a, a second infrared sensor 240b, and a third infrared sensor 240c, as shown in FIG. 8. In some embodiments, the first infrared sensor 240a is located adjacent to the distal ball joint 221a and the second collar spring 216b. In some embodiments, the second infrared sensor 240b is located adjacent to the distal ball joint 219a and the first collar spring 216a. In some embodiments, the third infrared sensor 240c is located in between the first suction valve 208a and the second suction valve 208b.

In some embodiments, the infrared sensors are positioned elsewhere in the insertion device. In some embodiments, the infrared sensors are positioned elsewhere in the cartridge. For example, in some embodiments, the infrared sensor is positioned in the distal portion of the cartridge 234a. In alternative embodiments, the first infrared sensor 240a, the second infrared sensor 240b, and the third infrared sensor 240c are light projectors. For example, in some embodiments, the light projectors project light in the infrared wavelength spectrum. In some embodiments, the light projectors project light in the visible wavelength spectrum. In some embodiments, the light projectors project light with a wavelength ranging from about at least 400 nm to about 800 nm or more. In some embodiments, the light projectors project a laser. In some embodiments, the light projectors project light that is beyond the outer edges of the cartridge 234. In some embodiments, the first infrared sensor 240a, the second infrared sensor 240b, and the third infrared sensor 240c detect light that is beyond the outer edges of the cartridge 234.

In some embodiments, the light projectors project a light in the visible spectrum onto the surface of the skin of the patient while the cartridge and/or the insertion device are separated from (e.g., not in contact with) the surface of the skin. In some embodiments, the light projectors project a light in the visible spectrum onto the surface of the skin of the patient once the cartridge is connected to the insertion device. In some embodiments, the user activates the light projectors and projects the light onto the surface of the skin of the patient in order to identify where the target blood vessel (e.g., a vein) is located. In some embodiments, a visible light image is displayed on the display screen. In some embodiments, the visible light image comprises an approximate location of a needle insertion point on the surface of the skin (e.g., an insertion indicator marking) and/or a linear needle insertion line (e.g., an indicator line).

In some embodiments, the proximal portion of the cartridge 234b comprises an aperture 226, as shown in FIG. 8. In some embodiments, the needle 168 exits the proximal portion of the cartridge 234b through the aperture 226. In some embodiments, the needle is connected to a catheter 170.

Figure 9:
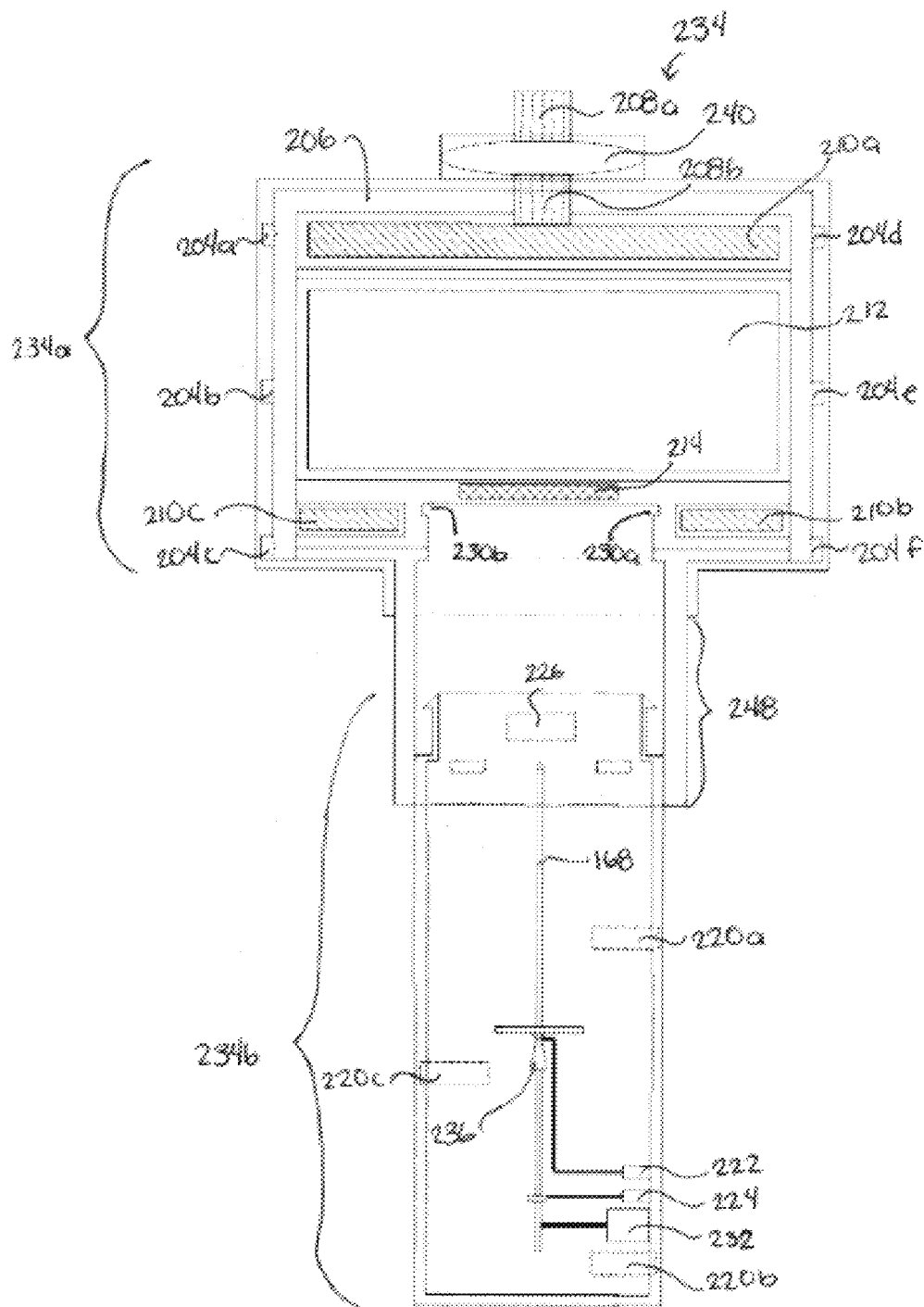
FIG. 9 illustrates a bottom view of an embodiment of a cartridge of the insertion device comprising a flexible collar in a stretched-out position.

FIG. 9 illustrates a bottom view of an embodiment of the cartridge 234 of the insertion device comprising the collar 248 in an extended position.

In some embodiments, the collar 248 is a flexible connection portion between the area of the cartridge under the sensor area of the device and the proximal portion of the cartridge 234b that contains the needle, catheter, and/or other insertion components. In some embodiments, the collar 248 has a lock (not shown in FIGS. 1-12) that prevents the movement of the proximal portion of the cartridge 234b relative to the distal portion of the cartridge 234a. In some embodiments, the lock is automatically locked prior to connecting the cartridge 234 to the insertion device 200. In some embodiments, the lock is automatically unlocked after connecting the cartridge 234 to the insertion device 200. In some embodiments, the lock is manually controlled (i.e., locked and unlocked) by the user at any point in time (e.g., before or after connecting the cartridge 234 to the insertion device 200). In some embodiments, the proximal portion of the cartridge 234b is sterile prior to use. In some embodiments, unlocking the lock of the collar 248, directly or indirectly opens the contents of the sterile proximal portion of the cartridge 234b to the environment. For example, in some embodiments, unlocking the lock of the collar 248 exposes the forward line of insertion for a needle and/or cannula. In some embodiments, collar 248 automatically assumes a locked and fixed position between the distal portion of the cartridge 234a and the proximal portion of the cartridge 234b, once the cartridge 234 is removed from the insertion device 200.

Figure 10:
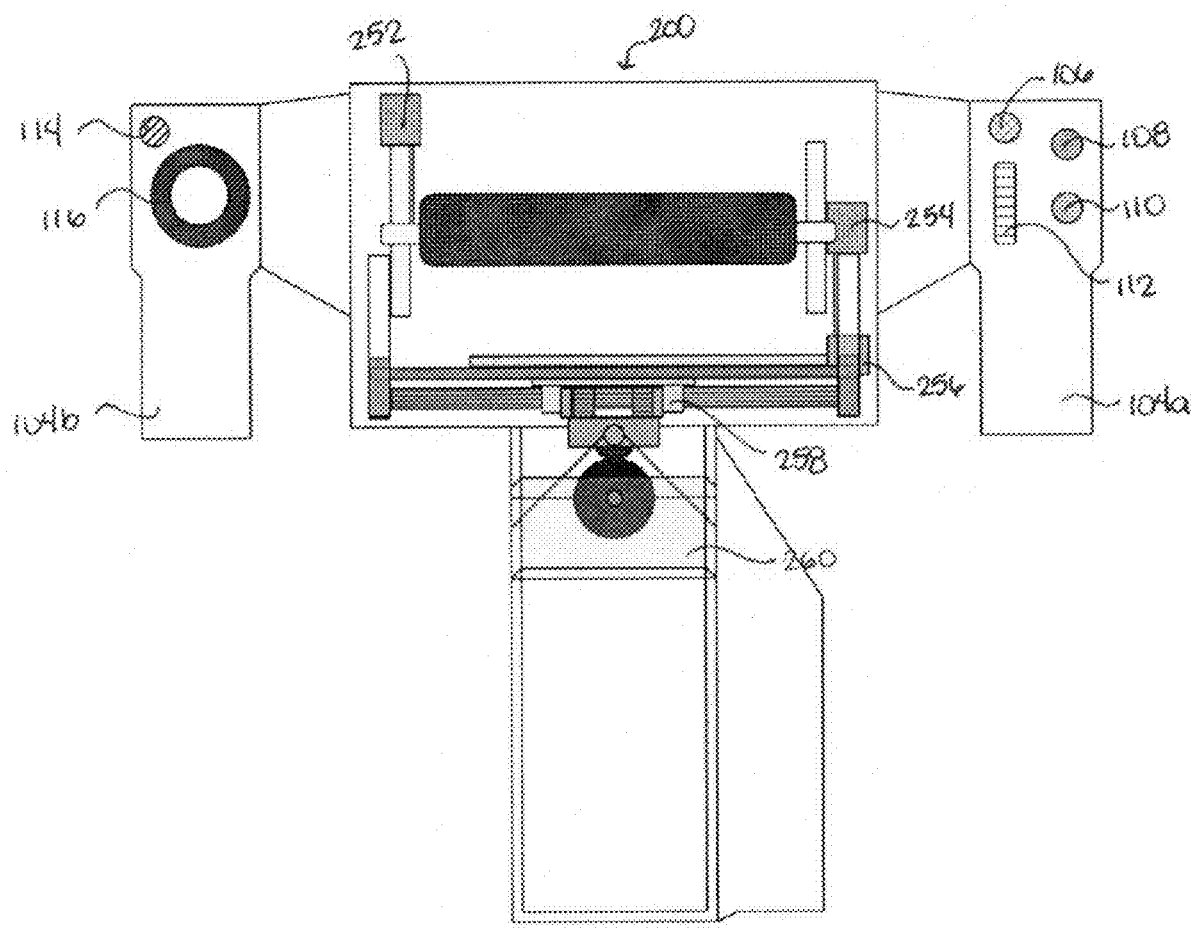
FIG. 10 illustrates a partial section view of an embodiment of the insertion device showing the actuator mechanisms.

FIG. 10 illustrates a partial section view of an embodiment of the insertion device showing the actuator mechanisms. In some embodiments, the insertion device comprises an ultrasound probe actuator 252. In some embodiments, the ultrasound probe actuator 252 controls the position of the ultrasound probe. In some embodiments, the ultrasound probe actuator 252 controls the angle of the ultrasound probe. In some embodiments, the ultrasound probe (i.e., the ultrasound transducer) is mobile within the body of the insertion device. In some embodiments, the ultrasound probe changes locations within the insertion device, thereby changing the position of the ultrasound plane. In some embodiments, the ultrasound probe actuator 252 controls the location of the ultrasound transducer.

In some embodiments, the insertion device comprises a first control arm actuator 254. In some embodiments, the first control arm actuator 254 is operatively connected to the first control arm 218a and the second control arm 218b. In some embodiments, the first control arm actuator 254 controls the longitudinal position of the first control arm 218a and the second control arm 218b. In some embodiments, the first control arm actuator 254 controls the distal and proximal position of the first control arm 218a and the second control arm 218b. In some embodiments, the first control arm actuator 254 tracks the longitudinal position of the first control arm 218a and the second control arm 218b. In some embodiments, the first control arm actuator 254 sends the tracked longitudinal positions to the computing device of the insertion device. In some embodiments, the computing device uses these tracked longitudinal positions to calculate the position of components such as, but not limited to the first control arm 218a, the second control arm 218b, the cartridge 234, and the needle 168.

In some embodiments, the insertion device comprises a second control arm actuator 256. In some embodiments, the second control arm actuator 256 is operatively connected to the first control arm 218a and the second control arm 218b. In some embodiments, the second control arm actuator 256 controls the horizontal position of the first control arm 218a and the second control arm 218b. In some embodiments, the first control arm actuator 254 controls the lateral position of the first control arm 218a and the second control arm 218b. In some embodiments, the second control arm actuator 256 tracks the horizontal position of the first control arm 218a and the second control arm 218b. In some embodiments, the second control arm actuator 256 sends the tracked horizontal positions to the computing device of the insertion device. In some embodiments, the computing device uses these tracked horizontal positions to calculate the position of components such as, but not limited to the first control arm 218a, the second control arm 218b, the cartridge 234, and the needle 168.

In some embodiments, the insertion device comprises a first rotary actuator 258. In some embodiments, the first rotary actuator 258 is operatively connected to the first control arm 218a and the second control arm 218b. In some embodiments, the first rotary actuator 258 controls the vertical angle of the first control arm 218a and the second control arm 218b. In some embodiments, the vertical angle is the angle defined as the vertical angle between the first control arm 218a and the main body of the insertion device and/or between the second control arm 218b and the main body of the insertion device. In some embodiments, the first rotary actuator 258 tracks the vertical angle of the first control arm 218a and the second control arm 218b. In some embodiments, the first rotary actuator 256 sends the tracked vertical angles to the computing device of the insertion device. In some embodiments, the computing device uses these tracked vertical angles to calculate the position of components such as, but not limited to the first control arm 218a, the second control arm 218b, the cartridge 234, and the needle 168.

In some embodiments, the insertion device comprises a second rotary actuator 260. In some embodiments, the second rotary actuator 260 is operatively connected to the first control arm 218a and the second control arm 218b. In some embodiments, the second rotary actuator 260 controls the horizontal angle of the first control arm 218a and the second control arm 218b. In some embodiments, the second rotary actuator 260 tracks the horizontal angle of the first control arm 218a and the second control arm 218b. In some embodiments, the second rotary actuator 260 sends the tracked horizontal angles to the computing device of the insertion device. In some embodiments, the computing device uses these tracked horizontal angles to calculate the position of components such as, but not limited to the first control arm 218a, the second control arm 218b, the cartridge 234, and the needle 168.

FIG. 11A shows a top view of the skin attachment cup 262 (i.e., FIG. 11A shows the anterior side of the skin attachment cup 262). FIG. 11B shows an isometric view of the skin attachment cup 262. FIG. 11C shows a front view of the skin attachment cup 262. In some embodiments, the insertion device 200 comprises a skin attachment cup 262. In some embodiments, the skin attachment cup 262 rapidly stabilizes and/or secures a medical instrument (e.g., a needle, a catheter, a cannula, and/or a guidewire) to the patient. In some embodiments, the skin attachment cup 262 locks the needle, cannula, and/or guidewire in place on the surface of the skin of the patient. In some embodiments, the skin attachment cup 262 is not used in combination with the insertion device 200 and/or the cartridge 234. In some embodiments, the skin attachment cup 262 is used in combination with the insertion device 200 and/or the cartridge 234. In some embodiments, the skin attachment cup 262 stays in place after removing the cartridge 234 from the surface of the skin of the patient.

In some embodiments, the skin attachment cup 262 comprises an adhesive area (not shown in FIGS. 11A-C) that reversibly binds to the skin. In some embodiments, the adhesive area is located on the posterior side of the skin attachment cup 262. In some embodiments, the adhesive area comprises an adhesive tape and a release liner. In some embodiments, the user removes the release liner in order to expose the adhesive tape prior to adhering the adhesive area onto the surface of the skin of the patient. In some embodiments, the posterior surface of the skin attachment cup 262 (not shown in FIGS. 11A-C) comprises a surface with a rough texture.

Alternatively, in some embodiments, the skin attachment cup 262 comprises one or more suction cups. In some embodiments, the user presses the skin attachment cup 262 onto the surface of the skin of the patient, thereby extruding air out of the suction cups and creating a vacuum. In some embodiments, the vacuum created causes the suction cups to cling to the surface of the skin of the patient immediately. In some embodiments, the skin attachment cup 262 comprises a mechanical connection to the insertion device 200. In some embodiments, the skin attachment cup 262 comprises a reversible, mechanical connection to a medical instrument (e.g., a needle, a catheter, a cannula, and/or a guidewire). In some embodiments, the skin attachment cup 262 is removed by the user from the medical instrument and/or the surface of the skin. In some embodiments, the user replaces the skin attachment cup 262 with a different dressing.

In some embodiments, the skin attachment cup 262 comprises a cylinder 274. In some embodiments, the cylinder 274 extends upwardly (i.e., along the z-axis) from the top surface of the skin attachment cup 262. In some embodiments, the cylinder comprises an opening 270 located at distal end of the cylinder, with respect to the top surface of the skin attachment cup 262 (i.e., the surface shown in FIG. 11B). In some embodiments, the cylinder 274 remains tightly closed if a wing spring 268 is not manually compressed. In some embodiments, the interior surface of the cylinder created by 264 is coated with an adhesive. In some embodiments, the interior surface of the cylinder created by 264 comprises a rough texture. In some embodiments, the skin attachment cup 262 comprises a first grip 264a and a second grip 264b. In some embodiments, the cylinder 274 is formed by the reversible coupling of the first grip 264a and the second grip 264b. In some embodiments, the first grip 264a and the second grip 264b are flexible. In some embodiments, the first grip 264a and the second grip 264b secure a catheter and/or a guidewire. In some embodiments, the first grip 264a and the second grip 264b overlap. In some embodiments, the first grip 264a and the second grip 264b are attached on one side of a semicircle. In some embodiments, the open end of the semicircle remains tightly opposed to one another through friction, adherent surfaces, and an angular force created by a wing spring 268, a first release tab 272a, and a second release tab 272b. The inferior surface, which corresponds to the distal end of the wire or catheter, is coated with an adhesive and has a rough surface, which binds to the skin of the patient after being deployed.

In some embodiments, the skin attachment cup 262 comprises a first wing leg 266a and a second wing leg 266b. In some embodiments, the first wing 266a and the second wing 266b are semi-rigid. In some embodiments, the first wing leg 266a and the second wing leg 266b are less flexible than the first grip 264a and the second grip 264b. In some embodiments, the first wing leg 266a and the second wing leg 266b distribute the mechanical forces produced by the wing spring 268, the first release tab 272a, and the second release tab 272b. In some embodiments, the first wing leg 266a and the second wing leg 266b distribute the linear force generated by the wing spring 268 in an arc shape, thereby creating an angular force on the first grip 264a and the second grip 264b. In some embodiments, the first wing leg 266a and the second wing leg 266b create a centripetal force on the arc created between the first grip 264a and the second grip 264b.

In some embodiments, the skin attachment cup 262 comprises the wing spring 268. In some embodiments, the wing spring 268, when extended, pushes the first wing 266a and the second wing 266b outward. In some embodiments, the skin attachment cup 262 comprises a first release tab 272a and a second release tab 272b. In some embodiments, the first wing 266a and the second wing 266b are pulled apart when the user compresses the first release tab 272a and the second release tab 272b. In some embodiments, the wing spring 268 exerts a linear force on the first release tab 272a and the second release tab 272b in opposing directions, away from the center of the wing spring 268. In some embodiments, the first release tab 272a and the second release tab 272b are attached firmly to the cylinder 274, such that the wing spring 268 exerts a linear force on the first release tab 272a and the second release tab 272b. In some embodiments, the linear force creates an angular and/or rotational force which further creates a rotational force on the first grip 264a and the second grip 264b with respect to one another. In some embodiments, the linear force creates an angular and/or rotational force which further creates an angular and/or centripetal force on the cylinder 274.

In some embodiments, the frictional and adherent surface of the cylinder 274, which together with the centripetal force caused by the wing spring 268, the first release tab 272a, and the second release tab 272b, holds a catheter and/or a guidewire in place with respect to the skin attachment cup 262.

In some embodiments, the skin attachment cup 262 comprises an opening 270. In some embodiments, the medical instrument (e.g., a needle, a catheter, a cannula, and/or a guidewire) exits and/or enters through the opening 270. In some embodiments, the user applies an inward directed force on the first release tab 272a and the second release tab 272b, thereby compressing the wing spring 268. In some embodiments, compression of the wing spring 268 produces an outward angular force on the first grip 264a and the second grip 264b. In some embodiments, the outward angular force on the first grip 264a and the second grip 264b causes the adherent connection between the first grip 264a and the second grip 264b to break. In some embodiments, the outward angular force on the first grip 264a and the second grip 264b causes the first grip 264a and the second grip 264b to separate. In some embodiments, the outward angular force on the first grip 264a and the second grip 264b causes the cylinder of 274 to open, thereby releasing the catheter and/or the guidewire. In some embodiments, the outward angular force on the first grip 264a and the second grip 264b creates an outward and vertical force (i.e., along the z-axis) on the first grip 264a and the second grip 264b, thereby pulling the majority of the skin attachment cup 262 off of the surface of the skin. In some embodiments, the outward angular force on the first grip 264a and the second grip 264b disconnects the first grip 264a and the second grip 264b. In some embodiments, of the rest of the skin attachment cup 262 is easily pulled off of the remaining surface of the skin by pulling of the skin attachment cup 262 by the user.

In some embodiments, before use, the skin attachment cup 262 adheres to the catheter and/or guidewire while the catheter sits in its initial resting position. In some embodiments, the skin attachment cup 262 is attached to the surface of the skin once the catheter and/or guidewire are advanced to its full insertion position. In some embodiments, the skin attachment cup 262 holds the catheter and/or guidewire to the surface of the skin with enough force to overcome a withdrawing of the needle through the interior surface of the catheter lumen.

Housing

In some embodiments, the housing 122 comprises an ultrasound transducer, a cartridge receiver, a needle holder, an infrared sensor, and/or a computing device. In some embodiments, the housing 122 encloses the ultrasound transducer, the cartridge receiver, the needle holder, the infrared sensor, and/or a computing device. In some embodiments, the housing 122 comprises the outer layer of the device, providing substantive and structural protection to the inner components. In some embodiments, the housing 122 is composed of a plastic material, for example. In some embodiments, the housing 122 is composed of polyvinyl chloride (PVC), polyethylene, polypropylene, or polystyrene. In some embodiments, the housing 122 is a plastic or an elastomer material including, but not limited to: polyethylene; polypropylene; polystyrene; polyester; polylactic acid (PLA); polycarbonate, polyvinyl chloride, polyethersulfone, polyacrylate or acrylic or polymethylmethacrylate (PMMA); polysulfone; polyetheretherketone (PEEK); thermoplastic elastomers or thermoplastic urethanes; or poly-p-xylylene or parylene. In some embodiments, the housing 122 is a metal such as, but not limited to, aluminum or stainless steel.

Ultrasound Transducer

The insertion device can comprise one or more imaging devices. The imaging device can be an ultrasound transducer. In some embodiments, the ultrasound transducer 213 is configured to emit and receive an ultrasound wave. In some embodiments, the ultrasound transducer (i.e., the ultrasound probe) is an ultrasound transmitter. In some embodiments, the ultrasound transmitter converts electrical signals into ultrasound waves. In some embodiments, the ultrasound transducer is an ultrasound receiver. In some embodiments, the ultrasound receiver converts ultrasound waves into electrical signals. In some embodiments, the ultrasound transducer is an ultrasound transceiver. In some embodiments, the ultrasound transceiver converts both electrical signals into ultrasound waves and ultrasound waves into electrical signals. In some embodiments, the ultrasound transducer is sized to fit within the housing 122. In some embodiments, the ultrasound transducer is used to generate cross-sectional images of the target tissue. In some embodiments, the ultrasound transducer comprises a non-invasive air bubble detector. In some embodiments, the non-invasive air bubble detector identifies the presence of a break in flow of a liquid (e.g., blood). In some embodiments, the ultrasound transducer is designed for use with a Doppler ultrasound system. In some embodiments, the ultrasound transducer is a linear array transducer. In some embodiments, the ultrasound transducer maintains a normal temperature that is safely tolerated by the surface of the skin of the individual (e.g., between about 25° C. to about 36° C.). In some embodiments, the ultrasound transducer has a frequency range varied based on the applicable examination. In some embodiments, for example, a frequency of 50 mega Hertz (MHz) is used for vascular examination. In some embodiments, an ultrasound transducer contains more than one operating frequency. In some embodiments the ultrasound transducer comprises a piezoelectric crystal, which generates and receives ultrasound waves. In some embodiments, the arrangement of the piezoelectric crystal is linear, curved (or convex), or phased. In some embodiments, the ultrasound transducer is a linear ultrasound transducer. In some embodiments, the ultrasound transducer is a curved or convex ultrasound transducer. In some embodiments, the ultrasound transducer is a phased array ultrasound transducer. In some embodiments, the ultrasound transducer is a pencil ultrasound transducer. In some embodiments, the ultrasound transducer is an endocavity transducer. In some embodiments, the ultrasound transducer is a transesophageal probe. In some embodiments, the dimensions of the device vary. In some embodiments, the device is suitable for handheld use.

In some embodiments, the ultrasound transducer has a frequency of about 2 MHz to about 12 MHz. In some embodiments, the ultrasound transducer has a frequency of at least about 2 MHz. In some embodiments, the ultrasound transducer has a frequency of at most about 12 MHz. In some embodiments, the ultrasound transducer has a frequency of about 2 MHz to about 3 MHz, about 2 MHz to about 4 MHz, about 2 MHz to about 5 MHz, about 2 MHz to about 6 MHz, about 2 MHz to about 7 MHz, about 2 MHz to about 8 MHz, about 2 MHz to about 9 MHz, about 2 MHz to about 10 MHz, about 2 MHz to about 11 MHz, about 2 MHz to about 12 MHz, about 3 MHz to about 4 MHz, about 3 MHz to about 5 MHz, about 3 MHz to about 6 MHz, about 3 MHz to about 7 MHz, about 3 MHz to about 8 MHz, about 3 MHz to about 9 MHz, about 3 MHz to about 10 MHz, about 3 MHz to about 11 MHz, about 3 MHz to about 12 MHz, about 4 MHz to about 5 MHz, about 4 MHz to about 6 MHz, about 4 MHz to about 7 MHz, about 4 MHz to about 8 MHz, about 4 MHz to about 9 MHz, about 4 MHz to about 10 MHz, about 4 MHz to about 11 MHz, about 4 MHz to about 12 MHz, about 5 MHz to about 6 MHz, about 5 MHz to about 7 MHz, about 5 MHz to about 8 MHz, about 5 MHz to about 9 MHz, about 5 MHz to about 10 MHz, about 5 MHz to about 11 MHz, about 5 MHz to about 12 MHz, about 6 MHz to about 7 MHz, about 6 MHz to about 8 MHz, about 6 MHz to about 9 MHz, about 6 MHz to about 10 MHz, about 6 MHz to about 11 MHz, about 6 MHz to about 12 MHz, about 7 MHz to about 8 MHz, about 7 MHz to about 9 MHz, about 7 MHz to about 10 MHz, about 7 MHz to about 11 MHz, about 7 MHz to about 12 MHz, about 8 MHz to about 9 MHz, about 8 MHz to about 10 MHz, about 8 MHz to about 11 MHz, about 8 MHz to about 12 MHz, about 9 MHz to about 10 MHz, about 9 MHz to about 11 MHz, about 9 MHz to about 12 MHz, about 10 MHz to about 11 MHz, about 10 MHz to about 12 MHz, or about 11 MHz to about 12 MHz. In some embodiments, the ultrasound transducer has a frequency of about 2 MHz, about 3 MHz, about 4 MHz, about 5 MHz, about 6 MHz, about 7 MHz, about 8 MHz, about 9 MHz, about 9 MHz, about 10 MHz, about 11 MHz, or about 12 MHz.

Infrared Sensor

In some embodiments, the insertion device comprises an infrared sensor. In some embodiments, the infrared sensor is configured to emit and receive an infrared radiation. In some embodiments, the infrared sensor comprises an infrared radiation source. In some embodiments, the infrared radiation source is a light emitting diode (LED) or an organic light emitting diode (OLED). In some embodiments, the infrared sensor comprises an infrared radiation detector. In some embodiments, the infrared radiation detector is an infrared photodetector or a temperature detector.

In some embodiments, the infrared sensor is configured to emit and/or receive an infrared wave. In some embodiments, the infrared sensor is configured to emit, receive, and/or detect an infrared radiation in the near infrared region, in the mid infrared region, or in the far infrared region. In some embodiments, the infrared wave ranges between about 0.70 microns (μm) to about 1000 μm. In some embodiments, the infrared wave ranges from about 0.70 μm to about 1,000 μm. In some embodiments, the infrared wave ranges from at least about 0.70 μm. In some embodiments, the infrared wave ranges from at most about 1,000 μm. In some embodiments, the infrared wave ranges from about 0.70 μm to about 1 μm, about 0.70 μm to about 3 μm, about 0.70 μm to about 4 μm, about 0.70 μm to about 5 μm, about 0.70 μm to about 6 μm, about 0.70 μm to about 10 μm, about 0.70 μm to about 50 μm, about 0.70 μm to about 100 μm, about 0.70 μm to about 500 μm, about 0.70 μm to about 750 μM, about 0.70 μm to about 1,000 μm, about 1 μm to about 3 μm, about 1 μm to about 4 μm, about 1 μm to about 5 μm, about 1 μm to about 6 μm, about 1 μm to about 10 μm, about 1 μm to about 50 μm, about 1 μm to about 100 μm, about 1 μm to about 500 μm, about 1 μm to about 750 μm, about 1 μm to about 1,000 μm, about 3 μm to about 4 μm, about 3 μm to about 5 μm, about 3 μm to about 6 μm, about 3 μm to about 10 μm, about 3 μm to about 50 μm, about 3 μm to about 100 μm, about 3 μm to about 500 μm, about 3 μm to about 750 μm, about 3 μm to about 1,000 μm, about 4 μm to about 5 μm, about 4 μm to about 6 μm, about 4 μm to about 10 μm, about 4 μm to about 50 about 4 μm to about 100 μm, about 4 μm to about 500 μm, about 4 μm to about 750 μm, about 4 μm to about 1,000 μm, about 5 μm to about 6 μm, about 5 μm to about 10 μm, about 5 μm to about 50 μm, about 5 μm to about 100 μm, about 5 μm to about 500 μm, about 5 μm to about 750 μm, about 5 μm to about 1,000 μm, about 6 μm to about 10 μm, about 6 μm to about 50 μm, about 6 μm to about 100 μm, about 6 μm to about 500 μm, about 6 μm to about 750 μm, about 6 μm to about 1,000 μm, about 10 μm to about 50 μm, about 10 μm to about 100 μm, about 10 μm to about 500 about 10 μm to about 750 μm, about 10 μm to about 1,000

μm, about 50 μm to about 100 μm, about 50 μm to about 500 μm, about 50 μm to about 750 μm, about 50 μm to about 1,000 μm, about 100 μm to about 500 μm, about 100 μm to about 750 μm, about 100 μm to about 1,000 μm, about 500 μm to about 750 μm, about 500 μm to about 1,000 μm, or about 750 μm to about 1,000 μm. In some embodiments, the infrared wave ranges from about 0.75 μm, about 1 μm, about 3 μm, about 4 μm, about 5 μm, about 6 μm, about 10 μm, about 50 μm, about 100 μm, about 500 μm, about 750 μm, or about 1,000 μm.

In some embodiments, the insertion device comprises about 1 infrared sensor to about 10 infrared sensors or more. In some embodiments, the insertion device comprises at least about 1 infrared sensor. In some embodiments, the insertion device comprises at most about 10 infrared sensors. In some embodiments, the insertion device comprises about 1 infrared sensor to about 2 infrared sensors, about 1 infrared sensor to about 3 infrared sensors, about 1 infrared sensor to about 4 infrared sensors, about 1 infrared sensor to about 5 infrared sensors, about 1 infrared sensor to about 6 infrared sensors, about 1 infrared sensor to about 7 infrared sensors, about 1 infrared sensor to about 8 infrared sensors, about 1 infrared sensor to about 9 infrared sensors, about 1 infrared sensor to about 10 infrared sensors, about 2 infrared sensors to about 3 infrared sensors, about 2 infrared sensors to about 4 infrared sensors, about 2 infrared sensors to about 5 infrared sensors, about 2 infrared sensors to about 6 infrared sensors, about 2 infrared sensors to about 7 infrared sensors, about 2 infrared sensors to about 8 infrared sensors, about 2 infrared sensors to about 9 infrared sensors, about 2 infrared sensors to about 10 infrared sensors, about 3 infrared sensors to about 4 infrared sensors, about 3 infrared sensors to about 5 infrared sensors, about 3 infrared sensors to about 6 infrared sensors, about 3 infrared sensors to about 7 infrared sensors, about 3 infrared sensors to about 8 infrared sensors, about 3 infrared sensors to about 9 infrared sensors, about 3 infrared sensors to about 10 infrared sensors, about 4 infrared sensors to about 5 infrared sensors, about 4 infrared sensors to about 6 infrared sensors, about 4 infrared sensors to about 7 infrared sensors, about 4 infrared sensors to about 8 infrared sensors, about 4 infrared sensors to about 9 infrared sensors, about 4 infrared sensors to about 10 infrared sensors, about 5 infrared sensors to about 6 infrared sensors, about 5 infrared sensors to about 7 infrared sensors, about 5 infrared sensors to about 8 infrared sensors, about 5 infrared sensors to about 9 infrared sensors, about 5 infrared sensors to about 10 infrared sensors, about 6 infrared sensors to about 7 infrared sensors, about 6 infrared sensors to about 8 infrared sensors, about 6 infrared sensors to about 9 infrared sensors, about 6 infrared sensors to about 10 infrared sensors, about 7 infrared sensors to about 8 infrared sensors, about 7 infrared sensors to about 9 infrared sensors, about 7 infrared sensors to about 10 infrared sensors, about 8 infrared sensors to about 9 infrared sensors, about 8 infrared sensors to about 10 infrared sensors, or about 9 infrared sensors to about 10 infrared sensors. In some embodiments, the insertion device comprises about 1 infrared sensor, about 2 infrared sensors, about 3 infrared sensors, about 4 infrared sensors, about 5 infrared sensors, about 6 infrared sensors, about 7 infrared sensors, about 8 infrared sensors, about 9 infrared sensors, or about 10 infrared sensors.

In some embodiments, the infrared sensor is a thermal infrared sensor. In some embodiments, the infrared sensor is a quantum infrared sensor. In some embodiments, the infrared sensor is a passive infrared sensor. In some embodiments, the infrared sensor is an infrared radiation source. In some embodiments, the infrared radiation source is an infrared diode (e.g., a light emitting diode (LED)). In some embodiments, the infrared diode emits a radiation with a wavelength ranging from at least about 740 nanometers (nm) to about 760 nm or more.

In some embodiments, the infrared diode emits a radiation with a wavelength ranging from about 700 nm to about 900 nm. In some embodiments, the infrared diode emits a radiation with a wavelength ranging from at least about 700 nm. In some embodiments, the infrared diode emits a radiation with a wavelength ranging from at most about 900 nm. In some embodiments, the infrared diode emits a radiation with a wavelength ranging from about 700 nm to about 710 nm, about 700 nm to about 720 nm, about 700 nm to about 730 nm, about 700 nm to about 740 nm, about 700 nm to about 750 nm, about 700 nm to about 760 nm, about 700 nm to about 770 nm, about 700 nm to about 780 nm, about 700 nm to about 790 nm, about 700 nm to about 800 nm, about 700 nm to about 900 nm, about 710 nm to about 720 nm, about 710 nm to about 730 nm, about 710 nm to about 740 nm, about 710 nm to about 750 nm, about 710 nm to about 760 nm, about 710 nm to about 770 nm, about 710 nm to about 780 nm, about 710 nm to about 790 nm, about 710 nm to about 800 nm, about 710 nm to about 900 nm, about 720 nm to about 730 nm, about 720 nm to about 740 nm, about 720 nm to about 750 nm, about 720 nm to about 760 nm, about 720 nm to about 770 nm, about 720 nm to about 780 nm, about 720 nm to about 790 nm, about 720 nm to about 800 nm, about 720 nm to about 900 nm, about 730 nm to about 740 nm, about 730 nm to about 750 nm, about 730 nm to about 760 nm, about 730 nm to about 770 nm, about 730 nm to about 780 nm, about 730 nm to about 790 nm, about 730 nm to about 800 nm, about 730 nm to about 900 nm, about 740 nm to about 750 nm, about 740 nm to about 760 nm, about 740 nm to about 770 nm, about 740 nm to about 780 nm, about 740 nm to about 790 nm, about 740 nm to about 800 nm, about 740 nm to about 900 nm, about 750 nm to about 760 nm, about 750 nm to about 770 nm, about 750 nm to about 780 nm, about 750 nm to about 790 nm, about 750 nm to about 800 nm, about 750 nm to about 900 nm, about 760 nm to about 770 nm, about 760 nm to about 780 nm, about 760 nm to about 790 nm, about 760 nm to about 800 nm, about 760 nm to about 900 nm, about 770 nm to about 780 nm, about 770 nm to about 790 nm, about 770 nm to about 800 nm, about 770 nm to about 900 nm, about 780 nm to about 790 nm, about 780 nm to about 800 nm, about 780 nm to about 900 nm, about 790 nm to about 800 nm, about 790 nm to about 900 nm, or about 800 nm to about 900 nm. In some embodiments, the infrared diode emits a radiation with a wavelength ranging from about 700 nm, about 710 nm, about 720 nm, about 730 nm, about 740 nm, about 750 nm, about 760 nm, about 770 nm, about 780 nm, about 790 nm, about 800 nm, or about 900 nm.

Alternatively, in other embodiments, the insertion device comprises a digital camera. In some embodiments, the digital camera detects an infrared wave or signal. In some embodiments, the digital camera detects a near-infrared wave or signal. In some embodiments, the digital camera is a near-infrared camera. In some embodiments, the digital camera is a webcam. In some embodiments, the digital camera is a smart phone camera or a camera phone. In some embodiments, the digital camera is a computer camera. In some embodiments, the digital camera is a thermographic camera or a thermal imaging camera. In some embodiments, the digital camera comprises an optical filter. In some embodiments, the optical filter facilitates detection of an infrared and/or a near-infrared radiation.

In some embodiments, the digital camera is used in combination with the infrared radiation source. In some embodiments, the insertion device comprises the infrared radiation source. In some embodiments, the infrared radiation source produces a radiation that is absorbed by deoxidized hemoglobin in blood. In some embodiments, the digital camera detects a radiation wave that is absorbed by the deoxygenated blood in blood vessels (e.g., in veins) in a target tissue. In some embodiments, the digital camera sends the detected radiation wave to the computing device. In some embodiments, the computing device generates an infrared image of the blood vessels containing deoxygenated blood in the target tissue. In some embodiments, the infrared image is ed on the display screen of the insertion device.

In some embodiments, the digital camera detects a radiation with a wavelength ranging from about 700 nm to about 900 nm. In some embodiments, the digital camera detects a radiation with a wavelength ranging from at least about 700 nm. In some embodiments, the digital camera detects a radiation with a wavelength ranging from at most about 900 nm. In some embodiments, the digital camera detects a radiation with a wavelength ranging from about 700 nm to about 710 nm, about 700 nm to about 720 nm, about 700 nm to about 730 nm, about 700 nm to about 740 nm, about 700 nm to about 750 nm, about 700 nm to about 760 nm, about 700 nm to about 770 nm, about 700 nm to about 780 nm, about 700 nm to about 790 nm, about 700 nm to about 800 nm, about 700 nm to about 900 nm, about 710 nm to about 720 nm, about 710 nm to about 730 nm, about 710 nm to about 740 nm, about 710 nm to about 750 nm, about 710 nm to about 760 nm, about 710 nm to about 770 nm, about 710 nm to about 780 nm, about 710 nm to about 790 nm, about 710 nm to about 800 nm, about 710 nm to about 900 nm, about 720 nm to about 730 nm, about 720 nm to about 740 nm, about 720 nm to about 750 nm, about 720 nm to about 760 nm, about 720 nm to about 770 nm, about 720 nm to about 780 nm, about 720 nm to about 790 nm, about 720 nm to about 800 nm, about 720 nm to about 900 nm, about 730 nm to about 740 nm, about 730 nm to about 750 nm, about 730 nm to about 760 nm, about 730 nm to about 770 nm, about 730 nm to about 780 nm, about 730 nm to about 790 nm, about 730 nm to about 800 nm, about 730 nm to about 900 nm, about 740 nm to about 750 nm, about 740 nm to about 760 nm, about 740 nm to about 770 nm, about 740 nm to about 780 nm, about 740 nm to about 790 nm, about 740 nm to about 800 nm, about 740 nm to about 900 nm, about 750 nm to about 760 nm, about 750 nm to about 770 nm, about 750 nm to about 780 nm, about 750 nm to about 790 nm, about 750 nm to about 800 nm, about 750 nm to about 900 nm, about 760 nm to about 770 nm, about 760 nm to about 780 nm, about 760 nm to about 790 nm, about 760 nm to about 800 nm, about 760 nm to about 900 nm, about 770 nm to about 780 nm, about 770 nm to about 790 nm, about 770 nm to about 800 nm, about 770 nm to about 900 nm, about 780 nm to about 790 nm, about 780 nm to about 800 nm, about 780 nm to about 900 nm, about 790 nm to about 800 nm, about 790 nm to about 900 nm, or about 800 nm to about 900 nm. In some embodiments, the digital camera detects a radiation with a wavelength ranging from about 700 nm, about 710 nm, about 720 nm, about 730 nm, about 740 nm, about 750 nm, about 760 nm, about 770 nm, about 780 nm, about 790 nm, about 800 nm, or about 900 nm.

Imaging Device Stage

In some embodiments, the imaging device stage can be used to manipulate the position of the one or more imaging devices with respect to the housing. The one or more imaging devices can be an ultrasound transducer, infrared sensor, and/or digital camera. In certain embodiments, the one or more imaging devices is an ultrasound transducer. In some embodiments, the imaging device stage can be an ultrasound stage. In some embodiments, the ultrasound stage can maintain a reference to the insertion device in any orientation. In some embodiments, the ultrasound stage can maintain a reference to the needle tip. The ultrasound stage can accommodate transverse and longitudinal scans of the vein anatomy along a central axis.

Figure 16:
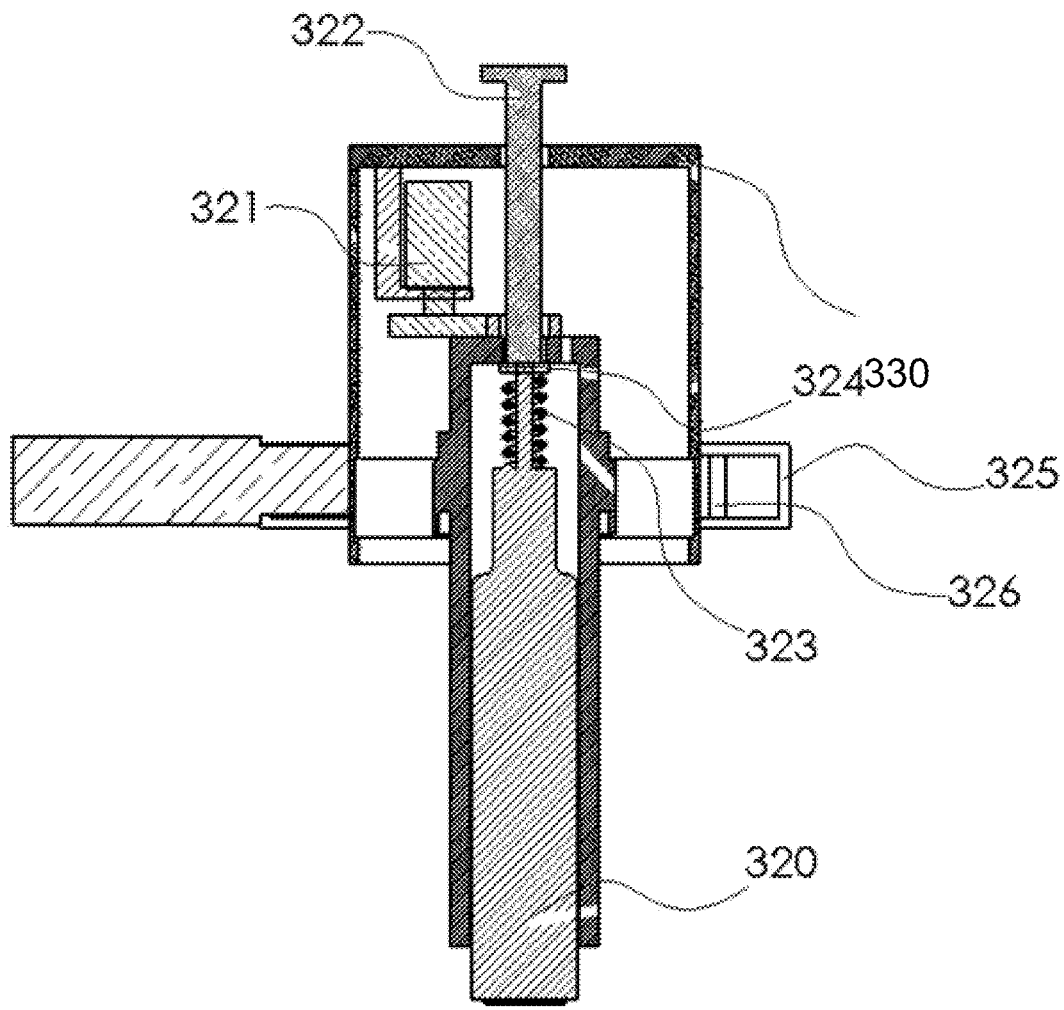
FIG. 16 illustrates a cross-sectional view of an ultrasound stage with translation and rotation mechanisms to move the ultrasound probe.

FIG. 16 illustrates an ultrasound stage 330 and the actuators that can provide translation and rotation for the ultrasound probe 320. In some embodiments, the translational mechanism is based on a linear rail 325 coupled to the ultrasound holder. In other embodiments, the translational mechanism is based on a rack and pinion. In other embodiments, the translational mechanism is based on a pulley system in combination with a polished rod and bushing. In some embodiments, the ultrasound transducer is translationally positioned using a linear actuator. In some embodiments, the linear actuator is a stepper motor and lead screw. In other embodiments, the linear actuator is driven with piezo electric elements. In other embodiments, the ultrasound probe is positioned using a servo and cam mechanism.

In some embodiments, the ultrasound stage 330 contains a rotation mechanism 321 for rotating the ultrasound probe 320. In some embodiments, the ultrasound stage can sweep and/or rotate ultrasound probe at least 10, 20, 30, 40, 50, 60, 70, 80, 90, 100, 110, 120, 130, 140, 150, 160, 170, or 180 degrees. In some embodiments, the ultrasound probe can be rotated at least 90, 120, 150, 180, 210, 240, 270, 300, 330, or 360 degrees. In some embodiments, the rotation mechanism comprises a stepper motor. In some embodiments, the rotation mechanism comprises a servo motor. In some embodiments, the rotation mechanism is a linear actuator pushing offset from a predefined rotation point. In some embodiments, the rotation mechanism comprises a cam.

The ultrasound stage can comprise a contact mechanism to provide an appropriate force on the ultrasound probe to maintain sufficient contact with the skin in order to produce a clear and consistent image. The contact mechanism can apply a range of forces sufficient to produce clear images while low enough to avoid collapsing a vein being imaged. In some embodiments, the contact mechanism can be adjusted to vary the contact force applied on different patient anatomies as patients with high levels of adipose tissue may require different amounts of force than those with normal levels of adipose tissue.

In some embodiments, the ultrasound holder 330 comprises a contact mechanism 323 to provide a downward force between the skin and ultrasound probe 320. In some embodiments, the contact mechanism is a spring driven system coupled mechanically to the ultrasound probe. In some embodiments, the contact mechanism comprises a linear actuator. In other embodiments, the contact mechanism is a cam mechanism actuated by a servomotor or stepper motor. In other embodiments, the contact mechanism comprises an electromagnetic coil that can generate a higher downward force with increasing current draw. In other embodiments, the contact mechanism comprises passive magnets coupled to a linear rail. In other embodiments, the contact mechanism applies air pressure to the ultrasound probe. In other embodiments, the contact mechanism comprises a compliant membrane. The membrane can comprise an elastomeric material. In other embodiments, the contact mechanism is any combination thereof.

The ultrasound stage can comprise an ultrasound control that allows users to manipulate the position of the ultrasound probe and to apply the downward contact force. The users can adjust the position and contact force applied based on the assessment of the target anatomy and determination of the appropriate path/alignment of the needle advancing through the lumen. The ultrasound control can be adjustable based on user input or controlled automatically through feedback from various sensors.

In some embodiments, the user can manually adjust the ultrasound control 322 to translate and/or rotate the ultrasound probe. In other embodiments, the control can comprise electrical switches attached to the insertion device. In other embodiments, the control can be automatically adjusted by the insertion device. In certain embodiments, the control can be any combination thereof.

In some embodiments, the amount of the downward force is manually adjusted by the user. In other embodiments, the amount force is electronically adjusted by the user using a lever or switch. In other embodiments, the amount of the force is automatically adjusted based on feedback from the sensor unit 324. In other embodiments, the sensors are pressure transducers based on either a piezo resistive strain gauge, capacitive diaphragm, electromagnetic diaphragm, piezoelectric strain, optical fiber strain gauge, or potentiometric wiper. In other embodiments, the sensors are any combination thereof.

The position ultrasound probe can be calibrated to a known value and/or maintained within a defined range. This can prevent the insertion device from operating beyond its available technical limits.

In some embodiments, the ultrasound holder contains ultrasound stop 326 to prevent the ultrasound probe 320 from moving beyond the intended range of motion and the calibration range of the probe. In other embodiments, the ultrasound stop comprises electrical limit switches. In other embodiments, the ultrasound stop comprises optical flags. In other embodiments, the ultrasound stop is operatively coupled to a drive mechanism. In other embodiments, the ultrasound stop is manually set by a user to limit the range of motion. In some embodiments, the ultrasound stop is set by the manufacturer. In some embodiments, the ultrasound stop is adjusted depending on the type of cartridge installed in the insertion unit. In other embodiments, the ultrasound stop is any combination thereof.

Thermoelectric Cooler

In some embodiments, the insertion device comprises a thermoelectric cooler. The thermoelectric cooler functions based on the Peltier effect; namely, it creates a heat flux between the junction of two different types of materials. In some embodiments, the thermoelectric cooler has a first side and a second side which upon application of a direct current (DC) electric current, heat is transferred from the first side to the second side. In some embodiments, the thermoelectric cooler decreases the temperature of a distal side of the thermoelectric cooler and increases the temperature of a proximal side of the thermoelectric cooler. In some embodiments, the distal side of the thermoelectric is a cooling plate having an active-cooling surface. In some embodiments, the thermoelectric cooler is mounted against the inner surface of the distal portion of the cartridge 234a. In some embodiments, the thermoelectric cooler sits adjacent to and makes thermal contact with the inner surface of the distal portion of the cartridge 234a. In some embodiments, the active-cooling surface of the thermoelectric cooler sits adjacent to and makes thermal contact with the inner surface of the distal portion of the cartridge 234a. In some embodiments, the thermoelectric cooler is mounted against the inner surface of the distal portion of the cartridge 234a. In some embodiments, the thermoelectric cooler transfers heat from the surface of the skin of the patient, to an active-cooling surface of the thermoelectric cooler. In some embodiments, this thermal transfer occurs through the inner surface of the distal portion of the cartridge 234a, to the cooling plate of the thermoelectric cooler, and finally to the heating plate and heat sink of the thermoelectric cooler; thereby reducing the surface temperature of the surface of the skin (e.g., an injection area) of a patient. In some embodiments, the heat transferred to the heating plate and/or the heat sink of the thermoelectric cooler is dissipated. In some embodiments, the thermoelectric cooler is configured to cool the active-cooling surface of the thermoelectric cooler by conduction.

In some embodiments, the insertion device comprises a temperature sensor (not shown in FIGS. 1-12). In some embodiments, the temperature sensor is operatively connected to the computing device of the insertion device. In some embodiments, the temperature sensor is operatively connected to the thermoelectric cooler. In some embodiments, the temperature sensor is operatively connected to the active-cooling surface. In some embodiments, the temperature sensor is configured to detect a temperature of the cooling plate. In some embodiments, the temperature sensor is configured to detect a temperature of the active-cooling surface of the thermoelectric cooler.

In some embodiments, the thermoelectric cooler comprises a heating plate facing away from the inner surface of the distal portion of the cartridge 234a. In some embodiments, the heating plate is in thermal connection with a heat sink. In some embodiments, the heat sink absorbs heat emitted by the heating plate. In some embodiments, the thermoelectric cooler comprises a fan. In some embodiments, the fan is configured to dissipate heat emitted by the heating plate. In some embodiments, the cooling plate and the heating plate of the thermoelectric cooler are separated by a material that does not conduct heat. In some embodiments, the controller controls and/or limits the length of time when the thermoelectric cooler is activated. In some embodiments, the computing device controls and/or limits the activation of the thermoelectric cooler. In some embodiments, the temperature sensor provides a feedback signal to the controller. In some embodiments, the feedback signal is a temperature of the cooling plate, a temperature of the heating plate, the temperature of the active-cooling surface, and/or the temperature of the surface of the skin of the patient. In some embodiments, the temperature sensor assists the computing device in controlling and/or limiting the length of time during which the thermoelectric cooler is activated. In some embodiments, the temperature sensor assists the computing device in controlling and/or limiting the activation of the thermoelectric cooler. In some embodiments, the computing device limits the length of time in which the thermoelectric cooler is activated.

In some embodiments, the thermoelectric cooler absorbs heat from a surface of the skin of a patient. In some embodiments, the thermoelectric cooler absorbs heat from a surface of the skin of a patient by direct contact between the cooled active-cooling surface and the surface of the skin. In some embodiments, the absorption of heat from the surface of the skin of the patient creates an anesthetic effect on the surface of the skin and/or in underlying tissue of the patient. In some embodiments, activating the thermoelectric cooler of the insertion device decreases the pain level that the patient feels during a medical procedure using the insertion device (e.g., needle insertion and/or catheter insertion and/or deployment). In some embodiments, activating the thermoelectric cooler of the insertion device anesthetizes the surface of the skin and/or underlying tissue of the patient during a medical procedure using the insertion device (e.g., needle insertion and/or catheter insertion and/or deployment). In some embodiments, activating the thermoelectric cooler of the insertion device has a local anesthetic effect on the patient. In some embodiments, activating the thermoelectric cooler of the insertion device has a local anesthetic effect on an injection region of the patient. In some embodiments, activating the thermoelectric cooler of the insertion device desensitizes, numbs, or deprives of sensation the surface of the skin and/or underlying tissue of the patient during a medical procedure using the insertion device (e.g., needle insertion and/or catheter insertion and/or deployment).

In some embodiments, the active-cooling surface of the thermoelectric cooler is cooled to a temperature ranging between about at least −10 to about 10 degrees Celsius or more. In some embodiments, the active-cooling surface is cooled to a temperature ranging between about at least −10 to about 5 degrees Celsius or more. In some embodiments, the active-cooling surface is cooled to a temperature ranging between at least about −10 to about 0 degrees Celsius or more. In some embodiments, the active-cooling surface is cooled to a temperature ranging between at least about −10 to about −5 degrees Celsius or more. In some embodiments, the active-cooling surface is cooled to a temperature ranging between at least about −15 to about 15 degrees Celsius or more. In some embodiments, the active-cooling surface is cooled to a temperature ranging between at least about −15 to about 10 degrees Celsius or more. In some embodiments, the active-cooling surface is cooled to a temperature ranging between at least about −15 to about 5 degrees Celsius or more. In some embodiments, the active-cooling surface is cooled to a temperature ranging between at least about −15 to about 0 degrees Celsius or more. In some embodiments, the active-cooling surface is cooled to a temperature ranging between at least about −15 to about −5 degrees Celsius or more. In some embodiments, the active-cooling surface is cooled to a temperature ranging between at least about −15 to about −10 degrees Celsius or more.

In some embodiments, the active-cooling surface is cooled to a temperature of about −15 degrees Celsius. In some embodiments, the active-cooling surface is cooled to a temperature of about −14 degrees Celsius. In some embodiments, the active-cooling surface is cooled to a temperature of about −13 degrees Celsius. In some embodiments, the active-cooling surface is cooled to a temperature of about −12 degrees Celsius. In some embodiments, the active-cooling surface is cooled to a temperature of about −11 degrees Celsius. In some embodiments, the active-cooling surface is cooled to a temperature of about −10 degrees Celsius. In some embodiments, the active-cooling surface is cooled to a temperature of about −9 degrees Celsius. In some embodiments, the active-cooling surface is cooled to a temperature of about −8 degrees Celsius. In some embodiments, the active-cooling surface is cooled to a temperature of about −7 degrees Celsius. In some embodiments, the active-cooling surface is cooled to a temperature of about −6 degrees Celsius. In some embodiments, the active-cooling surface is cooled to a temperature of about −5 degrees Celsius. In some embodiments, the active-cooling surface is cooled to a temperature of about −4 degrees Celsius. In some embodiments, the active-cooling surface is cooled to a temperature of about −3 degrees Celsius. In some embodiments, the active-cooling surface is cooled to a temperature of about −2 degrees Celsius. In some embodiments, the active-cooling surface is cooled to a temperature of about −1 degree Celsius. In some embodiments, the active-cooling surface is cooled to a temperature of about 0 degrees Celsius. In some embodiments, the active-cooling surface is cooled to a temperature of about 1 degree Celsius. In some embodiments, the active-cooling surface is cooled to a temperature of about 2 degrees Celsius. In some embodiments, the active-cooling surface is cooled to a temperature of about 3 degrees Celsius. In some embodiments, the active-cooling surface is cooled to a temperature of about 4 degrees Celsius. In some embodiments, the active-cooling surface is cooled to a temperature of about 5 degrees Celsius. In some embodiments, the active-cooling surface is cooled to a temperature of about 6 degrees Celsius. In some embodiments, the active-cooling surface is cooled to a temperature of about 7 degrees Celsius. In some embodiments, the active-cooling surface is cooled to a temperature of about 8 degrees Celsius. In some embodiments, the active-cooling surface is cooled to a temperature of about 9 degrees Celsius. In some embodiments, the active-cooling surface is cooled to a temperature of about 10 degrees Celsius. In some embodiments, the active-cooling surface is cooled to a temperature of about 11 degrees Celsius. In some embodiments, the active-cooling surface is cooled to a temperature of about 12 degrees Celsius. In some embodiments, the active-cooling surface is cooled to a temperature of about 13 degrees Celsius. In some embodiments, the active-cooling surface is cooled to a temperature of about 14 degrees Celsius. In some embodiments, the active-cooling surface is cooled to a temperature of about 15 degrees Celsius.

In some embodiments, the injection region of a patient is cooled by direct contact with the active-cooling surface of the thermoelectric cooler of the insertion device. In some embodiments, the injection region is cooled to a temperature ranging between about at least −10 to about 10 degrees Celsius or more. In some embodiments, the injection region is cooled to a temperature ranging between about at least −10 to about 5 degrees Celsius or more. In some embodiments, the injection region is cooled to a temperature ranging between at least about −10 to about 0 degrees Celsius or more. In some embodiments, the injection region is cooled to a temperature ranging between at least about −10 to about −5 degrees Celsius or more. In some embodiments, the injection region is cooled to a temperature ranging between at least about −15 to about 15 degrees Celsius or more. In some embodiments, the injection region is cooled to a temperature ranging between at least about −15 to about 10 degrees Celsius or more. In some embodiments, the injection region is cooled to a temperature ranging between at least about −15 to about 5 degrees Celsius or more. In some embodiments, the injection region is cooled to a temperature ranging between at least about −15 to about 0 degrees Celsius or more. In some embodiments, the injection region is cooled to a temperature ranging between at least about −15 to about −5 degrees Celsius or more. In some embodiments, the injection region is cooled to a temperature ranging between at least about −15 to about −10 degrees Celsius or more.

In some embodiments, the injection region is cooled to a temperature of about −15 degrees Celsius. In some embodiments, the injection region is cooled to a temperature of about −14 degrees Celsius. In some embodiments, the injection region is cooled to a temperature of about −13 degrees Celsius. In some embodiments, the injection region is cooled to a temperature of about −12 degrees Celsius. In some embodiments, the injection region is cooled to a temperature of about −11 degrees Celsius. In some embodiments, the injection region is cooled to a temperature of about −10 degrees Celsius. In some embodiments, the injection region is cooled to a temperature of about −9 degrees Celsius. In some embodiments, the injection region is cooled to a temperature of about −8 degrees Celsius. In some embodiments, the injection region is cooled to a temperature of about −7 degrees Celsius. In some embodiments, the injection region is cooled to a temperature of about −6 degrees Celsius. In some embodiments, the injection region is cooled to a temperature of about −5 degrees Celsius. In some embodiments, the injection region is cooled to a temperature of about −4 degrees Celsius. In some embodiments, the injection region is cooled to a temperature of about −3 degrees Celsius. In some embodiments, the injection region is cooled to a temperature of about −2 degrees Celsius. In some embodiments, the injection region is cooled to a temperature of about −1 degree Celsius. In some embodiments, the injection region is cooled to a temperature of about 0 degrees Celsius. In some embodiments, the injection region is cooled to a temperature of about 1 degree Celsius. In some embodiments, the injection region is cooled to a temperature of about 2 degrees Celsius. In some embodiments, the injection region is cooled to a temperature of about 3 degrees Celsius. In some embodiments, the injection region is cooled to a temperature of about 4 degrees Celsius. In some embodiments, the injection region is cooled to a temperature of about 5 degrees Celsius. In some embodiments, the injection region is cooled to a temperature of about 6 degrees Celsius. In some embodiments, the injection region is cooled to a temperature of about 7 degrees Celsius. In some embodiments, the injection region is cooled to a temperature of about 8 degrees Celsius. In some embodiments, the injection region is cooled to a temperature of about 9 degrees Celsius. In some embodiments, the injection region is cooled to a temperature of about 10 degrees Celsius. In some embodiments, the injection region is cooled to a temperature of about 11 degrees Celsius. In some embodiments, the injection region is cooled to a temperature of about 12 degrees Celsius. In some embodiments, the injection region is cooled to a temperature of about 13 degrees Celsius. In some embodiments, the injection region is cooled to a temperature of about 14 degrees Celsius. In some embodiments, the injection region is cooled to a temperature of about 15 degrees Celsius.

In some embodiments, the injection region of the patient is cooled to a temperature of about 10 degrees Celsius by direct contact between the injection region and the active-cooling surface of the thermoelectric cooler. In some embodiments, when the injection region reaches a desired temperature (e.g., 10 degrees Celsius), the temperature sensor sends a feedback signal to the computing device in order to deactivate the thermoelectric cooler. In some embodiments, the feedback signal triggers a change in the color of an indicator light (not shown in FIGS. 1-12). In some embodiments, the change in color of the indicator light notifies the user that the injection region is at the correct temperature and appropriately anesthetized for needle insertion.

In some embodiments, the injection region is contacted with the active-cooling surface for at least about 1 minute to about 5 minutes or more prior to insertion of the needle. In some embodiments, the injection region is contacted with the active-cooling surface for at least about 15 seconds to about 10 minutes or more prior to insertion of the needle. In some embodiments, the injection region is contacted with the active-cooling surface for at least about 30 seconds to about 10 minutes or more prior to insertion of the needle. In some embodiments, the injection region is contacted with the active-cooling surface for at least about 45 seconds to about 10 minutes or more prior to insertion of the needle. In some embodiments, the injection region is contacted with the active-cooling surface for at least about 1 minute to about 10 minutes or more prior to insertion of the needle. In some embodiments, the injection region is contacted with the active-cooling surface for at least about 2 minutes to about 5 minutes or more prior to insertion of the needle. In some embodiments, the injection region is contacted with the active-cooling surface for at least about 1 minute to about 5 minutes or more prior to insertion of the needle. In some embodiments, the injection region is contacted with the active-cooling surface for at least about 3 minutes to about 5 minutes or more prior to insertion of the needle.

In some embodiments, the injection region is contacted with the active-cooling surface for about 5 seconds prior to insertion of the needle. In some embodiments, the injection region is contacted with the active-cooling surface for about 10 seconds prior to insertion of the needle. In some embodiments, the injection region is contacted with the active-cooling surface for about 15 seconds prior to insertion of the needle. In some embodiments, the injection region is contacted with the active-cooling surface for about 30 seconds prior to insertion of the needle. In some embodiments, the injection region is contacted with the active-cooling surface for about 45 seconds prior to insertion of the needle. In some embodiments, the injection region is contacted with the active-cooling surface for about 1 minute prior to insertion of the needle. In some embodiments, the injection region is contacted with the active-cooling surface for about 2 minutes prior to insertion of the needle. In some embodiments, the injection region is contacted with the active-cooling surface for about 3 minutes prior to insertion of the needle. In some embodiments, the injection region is contacted with the active-cooling surface for about 4 minutes prior to insertion of the needle. In some embodiments, the injection region is contacted with the active-cooling surface for about 5 minutes prior to insertion of the needle. In some embodiments, the injection region is contacted with the active-cooling surface for about 6 minutes prior to insertion of the needle. In some embodiments, the injection region is contacted with the active-cooling surface for about 7 minutes prior to insertion of the needle. In some embodiments, the injection region is contacted with the active-cooling surface for about 8 minutes prior to insertion of the needle. In some embodiments, the injection region is contacted with the active-cooling surface for about 9 minutes prior to insertion of the needle. In some embodiments, the injection region is contacted with the active-cooling surface for about 10 minutes prior to insertion of the needle. In some embodiments, the injection region is contacted with the active-cooling surface for about 15 minutes prior to insertion of the needle.

Vibrator

In some embodiments, the insertion device comprises a vibrator. In some embodiments, the vibrator is activated by the user depressing a button or switch. Alternatively, in other embodiments, the vibrator is activated remotely by activation of an additional button and/or switch. In some embodiments, the vibrator creates vibrations that are transmitted through surface of the distal portion of the cartridge 234a. In some embodiments, the vibrator generates vibrations that produce an anesthetic effect, as perceived by the patient. In some embodiments, the vibrations produced by the vibrator create an anesthetic effect on the surface of the skin and/or in underlying tissue of the patient. In some embodiments, activating the thermoelectric cooler of the insertion device decreases the pain level that the patient feels during a medical procedure using the insertion device (e.g., needle insertion and/or catheter insertion and/or deployment). In some embodiments, activating the vibrator of the insertion device anesthetizes the surface of the skin and/or underlying tissue of the patient during a medical procedure using the insertion device (e.g., needle insertion and/or catheter insertion and/or deployment). In some embodiments, activating the vibrator of the insertion device has a local anesthetic effect on the patient. In some embodiments, activating the vibrator of the insertion device has a local anesthetic effect on an injection region of the patient. In some embodiments, activating the vibrator of the insertion device desensitizes, numbs, or deprives of sensation the surface of the skin and/or underlying tissue of the patient during a medical procedure using the insertion device (e.g., needle insertion and/or catheter insertion and/or deployment). In some embodiments, activation of the vibrator is controlled by the computing device. In some embodiments, activation of the vibrator is stopped based on the activation time of the thermoelectric cooler.

In some embodiments, activation of the vibrator causes the surface of the distal portion of the cartridge 234a to vibrate when the needle is inserted into the injection region of the individual. In some embodiments, activation of the vibrator causes the needle to vibrate when the needle is inserted into the injection region of the individual.

In some embodiments, the vibration has a vibration frequency ranging from about 100 Hertz (Hz) to about 300 Hz. In some embodiments, the vibrator produces a vibration frequency from at least about 100 Hz. In some embodiments, the vibrator produces a vibration frequency from at most about 300 Hz. In some embodiments, the vibrator produces a vibration frequency from about 100 Hz to about 125 Hz, about 100 Hz to about 150 Hz, about 100 Hz to about 175 Hz, about 100 Hz to about 200 Hz, about 100 Hz to about 225 Hz, about 100 Hz to about 250 Hz, about 100 Hz to about 275 Hz, about 100 Hz to about 300 Hz, about 125 Hz to about 150 Hz, about 125 Hz to about 175 Hz, about 125 Hz to about 200 Hz, about 125 Hz to about 225 Hz, about 125 Hz to about 250 Hz, about 125 Hz to about 275 Hz, about 125 Hz to about 300 Hz, about 150 Hz to about 175 Hz, about 150 Hz to about 200 Hz, about 150 Hz to about 225 Hz, about 150 Hz to about 250 Hz, about 150 Hz to about 275 Hz, about 150 Hz to about 300 Hz, about 175 Hz to about 200 Hz, about 175 Hz to about 225 Hz, about 175 Hz to about 250 Hz, about 175 Hz to about 275 Hz, about 175 Hz to about 300 Hz, about 200 Hz to about 225 Hz, about 200 Hz to about 250 Hz, about 200 Hz to about 275 Hz, about 200 Hz to about 300 Hz, about 225 Hz to about 250 Hz, about 225 Hz to about 275 Hz, about 225 Hz to about 300 Hz, about 250 Hz to about 275 Hz, about 250 Hz to about 300 Hz, or about 275 Hz to about 300 Hz. In some embodiments, the vibrator produces a vibration frequency from about 100 Hz, about 125 Hz, about 150 Hz, about 175 Hz, about 200 Hz, about 225 Hz, about 250 Hz, about 275 Hz, or about 300 Hz.

In some embodiments, the vibration has an amplitude ranging from about 0.3 G (wherein G is gravitational acceleration, i.e., 9.8 meters per second squared) to about 125 G. In some embodiments, the vibrator produces a vibration with an amplitude from at least about 0.3 G. In some embodiments, the vibrator produces a vibration with an amplitude of at most about 125 G. In some embodiments, the vibrator produces a vibration with an amplitude from about 0.3 G to about 1 G, about 0.3 G to about 5 G, about 0.3 G to about 15 G, about 0.3 G to about 25 G, about 0.3 G to about 50 G, about 0.3 G to about 75 G, about 0.3 G to about 100 G, about 0.3 G to about 105 G, about 0.3 G to about 110 G, about 0.3 G to about 125 G, about 1 G to about 5 G, about 1 G to about 15 G, about 1 G to about 25 G, about 1 G to about 50 G, about 1 G to about 75 G, about 1 G to about 100 G, about 1 G to about 105 G, about 1 G to about 110 G, about 1 G to about 125 G, about 5 G to about 15 G, about 5 G to about 25 G, about 5 G to about 50 G, about 5 G to about 75 G, about 5 G to about 100 G, about 5 G to about 105 G, about 5 G to about 110 G, about 5 G to about 125 G, about 15 G to about 25 G, about 15 G to about 50 G, about 15 G to about 75 G, about 15 G to about 100 G, about 15 G to about 105 G, about 15 G to about 110 G, about 15 G to about 125 G, about 25 G to about 50 G, about 25 G to about 75 G, about 25 G to about 100 G, about 25 G to about 105 G, about 25 G to about 110 G, about 25 G to about 125 G, about 50 G to about 75 G, about 50 G to about 100 G, about 50 G to about 105 G, about 50 G to about 110 G, about 50 G to about 125 G, about 75 G to about 100 G, about 75 G to about 105 G, about 75 G to about 110 G, about 75 G to about 125 G, about 100 G to about 105 G, about 100 G to about 110 G, about 100 G to about 125 G, about 105 G to about 110 G, about 105 G to about 125 G, or about 110 G to about 125 G. In some embodiments, the vibrator produces a vibration with an amplitude from about 0.3 G, about 1 G, about 5 G, about 15 G, about 25 G, about 50 G, about 75 G, about 100 G, about 105 G, about 110 G, or about 125 G.

In some embodiments, the vibrator is configured to cause the active-cooling surface, the drug delivery device, and/or a needle to vibrate. In some embodiments, the vibrator is configured to cause the distal portion of the cartridge 234a to vibrate. In some embodiments, the vibrator is configured to cause the thermoelectric cooling and vibration area 214 to vibrate. In some embodiments, the vibrator comprises a motor. In some embodiments, the motor is an eccentric rotating mass vibration motor or a linear resonant actuator. In some embodiments, the control of the activation and inactivation of the vibration and thermoelectric cooler is automatically triggered by attaching the cartridge 234 to the insertion device.

Cartridge and Cartridge Receiver

Disclosed herein, in certain embodiments, are needle cartridges, comprising a needle; a plate having a planar surface and a thickness configured to allow an ultrasound wave to pass therethrough; a needle holder, comprising an interior having a proximal end and a distal end and a track therebetween, the track having track walls configured to guide the needle, a needle connector configured to couple the needle to a plurality of actuators, a needle holder opening located at the distal end of the needle holder, and a port located at the proximal end of the needle holder; wherein the needle exits through the needle holder opening.

In some embodiments, the needle cartridge may comprise one, two, or more needles, catheters, or medical devices which may be specifically selected and controlled by the user. In some embodiments, the user can choose which needle, catheter, or other device is activated or deactivated by pressing a button, using a touch screen, voice command, or other control. The activation or deactivation can signal the computer to change which portion of the device is activated or deactivated, or receives signal output from the computer and controls. In some embodiments, the purpose of one, some, or all of the of the needles, catheters, or medical devices can be to inject a medication, fluid, tissue, cells, blood, other biological substances, or other material into a specific area, organ, vessel, tissue, nerve, joint, bone, tendon, or space on or within the patient's body. In some embodiments, the purpose of one, some, or all of the of the needles, catheters, or medical devices may alternatively be to drain, extract, biopsy, remove, withdrawal a medication, fluid, tissue, cells, other biological substances, or other material into a specific area, organ, vessel, tissue, nerve, joint, bone, tendon, or space on or within the patient's body. In some embodiments, the purpose of one, some, or all of the of the needles, catheters, or medical devices may alternately be to drill, penetrate, cut, or various other actions performed on a specific area, organ, vessel, tissue, nerve, joint, bone, tendon, or space on or within the patient's body. In some embodiments, the purpose of one, some, or all of the of the needles, catheters, or medical devices may alternately be to introduce a catheter, tube, wire, cardiac device, stent, sensor, or other medical device to a specific area, organ, vessel, tissue, nerve, joint, bone, tendon, or space on or within the patient's body. In some embodiments, one needle catheter, catheter, or medical device can perform one, two, or more of these functions listed, or they may perform multiple functions, which may include two or more of the safe functions, or any combination of the functions above, or others functions not listed here.

In some embodiments, some non-limiting examples of cartridges comprising one, two, or more needles, catheters, or medical devices with various purposes can include, but not be limited to, those in the disclosed herein. In some embodiments, a cartridge intended for joint procedures that contains three needles, with one used for anesthetizing a target area, one used for extracting fluid from the joint, and one used for injecting medications, cells, or biological substances into the joint. In some embodiments, a cartridge intended for joint procedures that contains two needles, with one used for anesthetizing a target area, and one for penetrating the joint capsule and used for injecting medications, cells, or biological substances, or other material into the joint space and also used for withdrawing joint fluid, cells, tissue, or other substances. In some embodiments, the cartridge intended for central venous procedures may contain two needles, one which is used for introducing anesthetizing fluids into the tissue near the target vessel, and one for introducing a needle, guidewire, catheter into the vessel, and capable of injecting blood, medications, or other substances into the vessel, and capable of withdrawing blood, medications, or other substances as well. In some embodiments, a cartridge used for abdominal paracentesis procedures may contain two needles, with one needle for injecting anesthetizing fluid into a target tissue, and one needle for penetrating a portion of completely through the abdominal wall and removing fluid and capable of introducing a catheter, and also capable of introducing a safety needle from within that needle used to penetrate the interior aspect of the abdominal wall that decreases the likelihood of penetrating bowel wall once in the abdomen. In some embodiments, a cartridge used for peripheral venous procedures, with two needles, with one for injecting an anesthetizing fluid to target tissue, and one for penetrating a vessel wall and introducing a guide wire and catheter that is also capable of injecting other fluids or substances or withdrawing blood or other fluids.

In some embodiments, the user does not use the cartridge in combination with the insertion device for a medical procedure (e.g., a needle and/or catheter insertion). In some embodiments, the user only uses the insertion device and does not use the cartridge for a medical procedure (e.g., a needle and/or catheter insertion). In some embodiments, the cartridge is sterile. In some embodiments, the cartridge is disposable. In some embodiments, the cartridge allows the transmission of one or more imaging modalities (e.g., ultrasound waves and/or infrared radiation). In some embodiments, the cartridge comprises medical instrumentation that is manipulated by the user in accordance with those imaging modalities.

In some embodiments, the cartridge serves as a barrier between the patient and the insertion device. In some embodiments, the cartridge serves as a barrier between the cartridge and the insertion device. In some embodiments, the cartridge protects the insertion device from contamination of blood or any other bodily fluid. In some embodiments, the cartridge acts as a bodily fluid-insertion device barrier. In some embodiments, the cartridge prevents costly decontamination procedures that would have to be carried out if the insertion device were to be contaminated by a bodily fluid. In some embodiments, the cartridge prevents replacement of an insertion device due to contamination of blood or any other bodily fluid. In some embodiments, the cartridge protects the patient from a contaminant present in or on the insertion device. In some embodiments, the cartridge protects a sample (e.g., a blood sample) from a contaminant present in or on the insertion device. In some embodiments, one or more mechanical parts that comprise the cartridge are designed to act as barrier while allowing for movement of the needle cartridge. In some embodiments, the cartridge allows movement of a needle holder, a needle, a guidewire, a catheter, or any combinations thereof, without exposing and/or contacting the inner parts of the cartridge to and/or with the insertion device and/or the patient. In some embodiments, the cartridge is sterile. In some embodiments, the cartridge is non-sterile.

In some embodiments, the cartridge 134 is coupled to the cartridge receiver 118. In some embodiments, the cartridge 134 is reversibly coupled to the cartridge receiver 118. In some embodiments, the cartridge receiver 118 and the cartridge 134 are operatively connected. In some embodiments, the cartridge receiver 118 and the cartridge 134 are reversibly and operatively connected. In some embodiments, the upper left connector 142a, the upper right connector 142b, the lower right connector 142c, and the lower left connector 142d are configured to engage with the plurality of second connectors (not shown in FIGS. 2A and 2B).

In some embodiments, the cartridge receiver 118 comprises a plurality of tabs configured to release the cartridge receiver 118 from the cartridge 134, once it is depressed by a user. In some embodiments, the cartridge receiver 118 comprises a tab configured to be depressed or pushed by a user in order to detach the cartridge receiver 118 from the cartridge 134. In some embodiments, the cartridge 134 and the cartridge receiver 118 are reversibly, operatively coupled to each other via a mechanism that includes an audible indication, such as, but not limited to, a clicking noise, a recording, and/or a ding sound, that indicates when the cartridge 134 and the cartridge receiver 118 are attached or detached by a user.

In some embodiments, the cartridge receiver 118 comprises a frame having a rail on either of its sides, the rail configured to secure the needle holder. In some embodiments, the cartridge 134 has a top surface, a bottom surface, a proximal end, and a distal end. In some embodiments, the cartridge 134 comprises a plurality of second connectors located on the top surface of the cartridge 134 (not shown in FIGS. 2A and 2B). In some embodiments, the plurality of second connectors is configured to form an electrical connection with the plurality of first connectors of the cartridge receiver 118.

In some embodiments, the plurality of first connectors is a plurality of male connectors. In some embodiments, the plurality of second connectors is a plurality of male connectors. In some embodiments, the plurality of first connectors is a plurality of female connectors. In some embodiments, the plurality of second connectors is a plurality of female connectors. In some embodiments, the plurality of second connectors is a plurality of tabs located within the cartridge receiver 118. In some embodiments, the plurality of first connectors fit into the tabs and allow for attachment of the two components. In some embodiments, additional connectors are located along the housing of the needle holder 138. In some embodiments, additional connectors are located on the posterior inner housing of the cartridge receiver.

Non-limiting examples of how to load the cartridge 134 onto the insertion device 100, include, pressing the cartridge 134 into the insertion device 100, including using snap fit features that allow the cartridge 134 to stay in place once loaded onto the insertion device 100, any magnetic means to hold the cartridge 134 in place, and/or any mechanical means to hold the cartridge 134 in place. In some embodiments, a tugging string is used to snap the cartridge 134 out of the insertion device 100. In some embodiments the cartridge 134 comprises snap ledges or other reversible means of loading the disposable sensor unit into the insertion device 100. In some embodiments, the cartridge 134 remains in place simply because it abuts a ledge of the insertion device 100. In some embodiments, one or more tabs are present on the external surface of the insertion device 100. In some embodiments, the cartridge 134 is reversibly loaded onto the insertion device 100.

In some embodiments, the cartridge comprises a plate 135. In some embodiments, the plate 135 has a planar surface and a thickness configured to allow the ultrasound wave to pass therethrough. In some embodiments, the plate 135 is fixed relative to the cartridge receiver. In some embodiments, the insertion device 100 comprises a disposable sleeve (not shown in the figures) configured to receive the cartridge 134. In some embodiments, the disposable sleeve is a sterile sleeve. In some embodiments, the sterile sleeve provides a sterile barrier between the insertion device 100 and the patient.

In some embodiments, the planar surface of the plate 135 comes in contact with the surface of the skin of the individual when using the insertion device. In some embodiments, the plate 135 is fixed relative to the cartridge receiver 118. In some embodiments, the plate 135 is a ceramic plate. In some embodiments, the ceramic is a lead zirconate titanate composition. In some embodiments, the plate 135 is a piezoresistive material. In some embodiments, the plate 135 is a backing material that reduces and/or prevents excessive vibration. In some embodiments, the plate 135 is an acoustic matching material that enables the ultrasound wave to efficiently enter the target tissue. In some embodiments, the acoustic matching material reduces the impedance of the target tissue that is reflected onto the ultrasound transducer. In some embodiments, the acoustic matching material comprises a combination of different resins. In some embodiments, the plate 135 has a density similar to soft tissue. In some embodiments, the plate 135 comprises a gel. In some embodiments, the gel is a gel elastomer. In some embodiments, the plate 135 is a metal plate. In some embodiments, the plate 135 is a plastic plate. In some embodiments, the plate 135 is an elastomeric plate. In some embodiments, the plate 135 comprises a composition of a polymer, metal, or both. In some embodiments, the plate 135 has a solid surface. In some embodiments, the plate 135 is has an elastomeric surface. In some embodiments, the elastomeric plate is a thermoplastic elastomeric plate. In some embodiments, the thermoplastic elastomeric plate is a gel. Non-limiting examples of a plastic or an elastomer include polyethylene; polypropylene; polystyrene; polyester; polylactic acid (PLA); polycarbonate, polyvinyl chloride, polyvinyl chloride plastisol (PVCP), polyethersulfone, polyacrylate or acrylic or polymethylmethacrylate (PMMA); polysulfone; polyetheretherketone (PEEK); thermoplastic elastomers or thermoplastic urethanes; and poly-p-xylylene or parylene. In some embodiments, the plate 135 is a silicone plate. In some embodiments, the plate 135 is a PVCP plate. In some embodiments, the plate 135 is an epoxy plate.

Alternatively, in other embodiments, the insertion device comprises a cartridge 234, as shown in FIGS. 6-10 and as described elsewhere herein.

During an insertion procedure, correct alignment of the cartridge can be essential to correctly determine the needle/catheter position and/or the orientation relative to the ultrasound transducer. In certain embodiments, the cartridge is aligned/calibrated with respect to the needle/catheter position and the ultrasound transducer prior to the needle insertion.

In some embodiments, the insertion device comprises a cartridge loading sensor to identify when a cartridge is properly inserted into the cartridge receiver. In some embodiments, the cartridge loading sensor can comprise an electrical limit switch. In some embodiments, the cartridge loading sensor can comprise an optical switch. In other embodiments, the cartridge loading sensor can be a hall-effect sensor. In other embodiments, the cartridge loading sensor can comprise a series of electrical contacts on both the cartridge and the cartridge receiver. In certain embodiments, the cartridge loading sensor comprises alignment features. In other embodiments, the cartridge loading sensor is any combination thereof.

In some embodiments, different types of cartridges can be loaded to the cartridge receiver. The different cartridges can comprise different sized needles. The different cartridges can comprise the catheters of different length, diameter, and/or materials. The different cartridges can comprise different combination of the needle and the catheter. The different cartridges can allow different range of needle and/or needle stage motions.

In some embodiments, the insertion device comprises a cartridge detector to correctly identify the type of cartridge inserted into the cartridge receiver. In some embodiments, the cartridge detector is an NFC chip located in the cartridge. In other embodiments, the cartridge detector is a barcode scanning system built into the insertion device. In other embodiments, the cartridge detector comprises an internal printed circuit board (PCB). In other embodiments, the cartridge type is manually selected by the user. In other embodiments, the cartridge detector is any combination thereof.

In some embodiments, the cartridge or device may comprise a specific shape according to the anatomic features, body size, or age of the patient. In some embodiments, the cartridge device may have varying shapes related to anatomic differences such as thickness of skin, depth of target vessels, depth of target organs, size of target lumen or space, or other anatomic differences. In some embodiments, the cartridges or device may have varying shapes for intended body size and shape of the patient. In some embodiments, the cartridges may have specific shape according to the patient's age. Some non-limiting examples of cartridge and device specific shapes would include small bottom surfaces on the cartridges intended for pediatric patients, patients with small lumen vessels, patients with small stature, or various other intended or anticipated characteristics of the patient's body. Other anatomic differences for which some cartridges may be specifically shaped for would unusually deep target vessels or organs, thick layers of tissue over the target, unusually mobile or fragile vessels, all of which may be more successful with shape of cartridges that are larger or angled on the bottom of the cartridge such that the needle, catheter, or medical devices can be inserted deeper within the tissue. In some embodiments, many other size and shape variations of the cartridge and device can be used for specific anatomic features of the patient, body size of the patient, or age of patient. In some embodiments, the cartridge and device size and shape may vary according to a combination more than one anatomic feature, body size, age, type of procedure, or other variables not here listed.

In some embodiments, the starting position and allowable movement path of the imaging device is dictated by the cartridge attached to the device. In some embodiments, the cartridge may have a certain shape to optimize various aspects of the intended procedure, and the shape of the required cartridge may also be affected by other variables such as the size or anatomic features of the patient, and the intended procedural site of the procedure. When the user attaches the desired cartridge to the device, a sensor on the device detects the various features of the cartridge or detects a sign or signal of those shaped components, features, and intended procedure, which is sent to the onboard computer, computed, and output form that computer is sent to the mechanisms controlling the position of the imaging device, and moves it to a preferred starting position within the cartridge. When the user subsequently adjusts the location of the imaging device, the signals sending the control input are sent to the computer, which only will send output to the imaging control mechanisms to move the imaging device within those necessary parameters.

In some embodiments, the starting and allowable settings, displayed image depth, gain, and other aspects of the image screen and displayed information also are specific to the attached cartridge. As disclosed herein, in some embodiments, the cartridge may have a certain shape to optimize various aspects of the intended procedure, and the shape of the required cartridge may also be affected by other variables such as the size or anatomic features of the patient, and the intended procedural site of the procedure. Because of the variations in shape and need to optimize the displayed image for certain procedures, the starting and allowable settings, displayed image depth, gain, and other aspects of the image screen and displayed information can be varied appropriately. When the user attaches the desired cartridge to the device, a sensor on the device can detect the various features of the cartridge or detect a sign or signal of those shape components, features, and intended procedure, which is sent to the onboard computer, computed, and output form that computer is sent to the imaging device and display screen.

In some embodiments, the shape of the cartridge is unique to the intended procedure. The shape of the cartridge can be optimized for the type of procedure for which it is intended such that it provides for better surface contact between the patient and the cartridge, allows for better image quality, allows for better image fields, allows for more desirable movement of the imaging component relative to the device or patient's body, allows for more effective or useful vacuum actions of the cartridge or device, allows for better attachment to the patient, allows for more preferable angles of needle and device insertion, allows the user to be in a more comfortable or accessible position relative to the procedure location, allows for views or images for which the user are more familiar with, allows for improved safety, allows for increased likelihood of procedural success, provides more comfort for the patient, provides some other advantage, or some combination of the advantages thereof. When the user chooses to perform a certain procedure, the user can select a cartridge with a shape intended for use for that procedure.

In some embodiments, the cartridge is shaped for peripheral venous procedures, central venous procedures, arterial procedures, abscess drainage procedures, biopsy procedures, joint procedures, nerve procedures, spinal procedures, chest tube procedures, cardiac procedures, other thoracic procedures, cricothyroidotomy procedures, other neck procedures, abdominal paracentesis procedures, bladder procedures, other abdominal procedures, other extremity procedures, other head procedures, osseous procedures, other procedures, a procedure involving a certain approach of the device relative to body, a subset of any of these procedures, or any combination thereof.

In some embodiments, the shape and external of the cartridge is intended for peripheral venous procedures. In some embodiments, this cartridge has a slight curvature on the bottom of the device in the horizontal plane relative to the body of the device, such that the curvature allows for better contact between the lower surface of the cartridge and the skin surface of an extremity. This shape allows for the imaging component to move substantially in the longitudinal direction and horizontal directions, change axis direction relative to the surface of the skin, change vertical location, among other useful movements. This shape would provide a more comfortable positioning of the user. The shape would also allow the user to activate the vacuum components of the cartridge or device in a more useful manner, with vacuum area at the distal end of the device to provide a more effective tourniquet effect on the vessels running longitudinal relative to the body of the device, while providing stability of the device in the longitudinal plane relative to the longitudinal plane of the extremity. In other embodiments, the cartridge may have a different shape to optimize different aspects of this procedure.

In some embodiments, the shape of the cartridge is intended for central venous access. In some embodiments, the cartridge intended for central venous procedures, has a bottom surface that is slightly curved in the horizontal direction. In some embodiments, the cartridge shape also includes a longer proximal portion of the cartridge in the vertical as compared to the front portion of the cartridge, and a shorter bottom side compared to some other cartridges. The shape is such that the bottom portion of the device is angled relative to the patient's skin surface, with the posterior aspect of the device is farther from the surface of the skin. This shape can make it easier for the user to insert the needle at a more acute angle, as the central venous structures are located deeper than peripheral structures and increases the likelihood of procedural success. The smaller bottom surface of the cartridge in this embodiment, can make it easier for the user to perform the procedure on areas of the patient that have limited skin surface available, such as the side of the neck when accessing the internal jugular vein among other locations. In other embodiments, the cartridge intended for central venous access may have a different shape to optimize different aspects of this procedure.

In some embodiments, the shape of the cartridge is intended for arterial procedures. In some embodiments, the bottom of this cartridge has a significantly shorter bottom in the longitudinal direction as opposed to top side. This can decrease the longitudinal surface area of portion of the cartridge to allow better access the arteries of the wrist, which have a limited accessible area in the longitudinal direction in some patients. In other embodiments, the cartridge intended for arterial access may have a different shape to optimize different aspects of this procedure.

In some embodiments, the shape of the cartridge is intended for joint procedures. In some embodiments, the shape of the cartridge is intended specific to a subsegment of these procedures. In some embodiments, the shape of the cartridge is intended for knee procedures. In some embodiments, there is a curvature in a portion of the bottom side of the cartridge, with only the distal end of the cartridge where the imaging device images the patient's leg being curved in the longitudinal direction. This can allow the procedure to be performed with the long axis of the body of the device in a perpendicular orientation relative to the leg length direction. The needle insertion orientation can improve the likelihood of success of the procedure, while allowing for the vacuum effects of the cartridge or device to be more effective.

In some embodiments, the shape of the needle cartridge is intended for a different subsegment of the joint procedures. In some embodiments, the shape of the needle cartridge is intended for hip procedures. In some embodiments, there is a curvature in the horizontal direction on the entirety of the bottom surface of the cartridge. This allows for more stability of the device on the leg, more effective vacuum effects. In other embodiments, the cartridge intended for hip procedures may have a different shape to optimize different aspects of this procedure.

In some embodiments, the shape of the needle cartridge is intended for spinal procedures. In some embodiments, the cartridge intended for spinal procedures has a bottom surface is divided into two sections, which sit at different angles relative to the bottom of the device and to the surface of the skin. The more distal portion of the bottom surface is angled with the bottom surface facing distally, and the more proximal portion of the bottom surface of the cartridge may be angled forward as well, but at a less acute angle relative to the bottom of the device housing. This can allow for better imaging of the vertebral spinous processes and allow the angle for needle and medical device insertion to take place significantly closer to perpendicular to the skin surface, to go deeper and between those vertebral spinous processes. In this embodiment the vacuum portions of the cartridge and device are on the more distal surface of the bottom side of the cartridge. In other embodiments, the cartridge intended for spinal procedures may have a different shape to optimize different aspects of this procedure.

In some embodiments, the shape of the needle cartridge is intended for abdominal paracentesis. In some embodiments, the cartridge intended for abdominal paracentesis has a bottom shape which is curved in the horizontal axis, and the bottom side of the cartridge effacing the skin is shorter in length than the upper side which faces the device. The bottom side of the cartridge may also be angled slightly forward. This shape can improve the surface contact, the imaging angle, and increase ease of use by the user among other benefits. In other embodiments, the cartridge intended for abdominal paracentesis procedures may have a different shape to optimize different aspects of this procedure.

In some embodiments, the shape of the needle cartridge is intended for thoracic procedures, such as tube thoracostomy, thoracentesis, paracardiocentesis, or other thoracic procedures. In some embodiments, the cartridge intended for thoracic procedures has a bottom surface is divided into two sections, which sit at different angles relative to the bottom of the device and to the surface of the skin. The more distal portion of the bottom surface is angled with the bottom surface facing distally, and the more proximal portion of the bottom surface of the cartridge is angled forward as well, but at a less acute angle relative to the bottom of the device housing. This can allow for better imaging of the ribs, and allows the angle for needle and medical device insertion to take place at a steeper to the skin surface in order to go deeper and between the ribs. In this embodiment the vacuum portions of the cartridge and device are on the more distal surface of the bottom side of the cartridge. In other embodiments, the cartridge intended for thoracic procedures may have a different shape to optimize different aspects of this procedure.

In some embodiments, the shape of the needle cartridges is intended for osseous procedures, such as interosseous line placement in the extremity or sternum, or other osseous procedures. In some embodiments, the cartridge intended for osseous procedures has a bottom surface is divided into two sections, which sit at different angles relative to the bottom of the device and to the surface of the skin. The more distal portion of the bottom surface is angled with the bottom surface facing distally, and the more proximal portion of the bottom surface of the cartridge is angled forward as well, but at a less acute angle relative to the bottom of the device housing. This angle can be present so the user can apply more force on the device relative to the patient's body surface, and the needle or insertion component can be directed perpendicular to the surface of the skin and bone, among other advantages. In other embodiments, the cartridge intended for osseous procedures may have a different shape to optimize different aspects of this procedure.

In some embodiments, the cartridge contains one or more pain reduction mechanisms. This can include a thermal mass which may be pre-cooled before the procedure, constant or intermittent vibration mechanisms, thermal transduction area, rough distracting surface, evaporating liquid emitter, or other pain reduction mechanisms. The cartridge may comprise one or any combination of the disclosed pain reduction mechanisms.

In some embodiments, the cartridge may comprise one or more medication, fluid, tissue, cells, blood, other biological substances, or other material that is preloaded into a container or containers within the cartridge according to the specific intended purpose of that insertion device. In some embodiments, that preloaded substance can be one or more medications including, but not limited to, lidocaine, bupivacaine, epinephrine, vasopressin, norepinephrine, antibiotics, other medications, other fluids, other mixtures, and other substances. In some embodiments, the cartridge may comprise preloaded biological fluids, blood, antibodies, tissue, cells, stem cells, or other biological substances.

In some embodiments, the cartridge may comprise a fluid tube or other connection between the preloaded fluids or substance holding containers and one or more of the needles, catheters, medical devices.

In some embodiments, the device may be simplified such that a cartridge with manually controllable vacuum areas on the bottom surface is able to attach to a standard ultrasound probe while providing a barrier between the ultrasound probe and the patients' skin, tissue, and bodily fluids. In some embodiments, the vacuum area would draw air and tissue from under the cartridge, stabilizing the cartridge and probe. In some of the embodiments, the probe attachment portion of this cartridge would be mobile along the longitudinal length of the cartridge, or the axis may be turned from horizontal orientation relative to the cartridge, or moved vertically such that the probe is applying more or less pressure to the underlying tissue, or have the capability for some combination of those movements. In some embodiments, the device further comprises an attachment for a mobile device or screen which displays the ultrasound image, with other embodiments requiring the user to view the display which the probe is attached to.

In some embodiments, the device may comprise one or more controls, electrical connections, computing abilities, motion functions, or injections functions, such that the user can control with a high degree of accuracy the amount of fluid, blood, medication, cells, other biological fluids, or other substances injected through one of the needles, catheters, or other medical devices. In some embodiments these fluids, blood medications, may be preloaded in the cartridge or connected to the outer aspects of the cartridge, directly, through tubing, or through some other type of connection.

Needle Holder

In some embodiments, the cartridge 134 comprises a needle holder 138, as shown in FIGS. 2A and 2B. In some embodiments, the needle holder 138 holds the medical device to be inserted into the patient. In some embodiments, the needle holder 138 holds a syringe and/or a catheter. In some embodiments, the needle holder 138 comprises a rectangular compartment comprised of a metal and/or polymer material. In some embodiments, the needle holder 138 comprises an interior having a proximal end 127, a distal end 125, and a track (not shown in FIGS. 2A and 2B) therebetween. In some embodiments, the track has walls configured to guide a needle. In some embodiments, the track has walls configured to guide a syringe. In some embodiments, the needle holder 138 comprises a needle connector (not shown in FIGS. 2A and 2B) configured to couple the syringe to a plurality of actuators (not shown in FIGS. 2A and 2B). In some embodiments, the plurality of actuators comprises a spring actuator and an angle actuator. In some embodiments, the spring actuator controls the longitudinal movement of the needle. In some embodiments, the angle actuator controls the needle holder angle. In some embodiments, the insertion device comprises a hydraulic, pneumatic, electric, or mechanical actuator. In some embodiments, a hydraulic actuator converts hydraulic power into mechanical energy. In some embodiments, a pneumatic actuator converts the energy of compressed gas into motion. In some embodiments, electric actuators convert electrical energy into mechanical torque. In some embodiments, mechanical actuators convert rotary motion into linear motion. In some embodiments, the actuator implemented enables the device to adjust the position of the needle prior to injection.

In some embodiments, the needle holder 138 comprises an interior. In some embodiments, the interior has a proximal end, distal end, and a track therebetween. In some embodiments, the track 134 has at least one track wall configured to guide the needle 168. In some embodiments, the needle holder 138 comprises a needle connector configured to couple the needle to a plurality of actuators. In some embodiments, the plurality of actuators comprises a spring actuator and an angle actuator. In some embodiments, the spring actuator controls the longitudinal movement of the needle. In some embodiments, the angle actuator controls the needle holder angle. In some embodiments, the needle holder 138 comprises a port lever or a collection tube configured to be received by the port. In some embodiments, the port lever moves within a cartridge arc path as the needle holder is moved from one selected position to another.

In some embodiments, the needle holder comprises a needle holder opening 160 located at the distal end of the needle holder 138. In some embodiments, the needle holder comprises a port located at the proximal end of the needle holder 138. In some embodiments, the needle exits through the needle holder opening 160.

In some embodiments, the needle holder track 136, allows the needle holder to move when the user adjusts needle angle, as shown by the arrow in FIG. 2B. In some embodiments, the needle holder track 136 is located along a right lateral side or a left lateral side of the insertion device 100. In some embodiments, the needle holder track 136 has a curved shaped. In some embodiments, the needle holder track 136 extends uniformly in one direction only. In some embodiments, the needle holder track 136 is configured to receive a knob or a lever that is used to manually move and/or change the angle of the needle holder 138. In some embodiments, the tube 120 serves as a knob or a lever once inserted into the port 115, as shown in FIG. 2B. In some embodiments, the needle holder 138 is automatically moved along the needle holder track 136. In some embodiments, the angle of the needle holder 138 is automatically adjusted along the needle holder track 136.

In some embodiments, the needle holder 138 comprises a port 115. In some embodiments, the port 115 comprises a lever to manually adjust the angle of the needle holder 138 prior to needle insertion. In some embodiments, the port 115 comprises a vacutainer connection that creates a vacuum seal inside a collection tube. In some embodiments, the port 115 comprises a fluid connection with a collection tube. In some embodiments, the port 115 comprises a tubing connection. In some embodiments, the port 115 comprises an opening configured to receive a tube (e.g., a vacutainer tube or a collection tube) or tubing. In some embodiments, the opening of the port comprises a seal (e.g., a gasket or an O-ring) to create a hermetic seal between the tube and the port 115. In some embodiments, the seal is composed of synthetic rubber or a thermoplastic. In some embodiments, the seal sits on the rim of the port 115. In some embodiments, the seal sits on the outer edge of the port 115. In some embodiments, the port 115 is located on the distal end of the insertion device 100 and on the dorsal side of the insertion device 100.

In some embodiments, the port 115 is used as a terminal for tubing and manual adjustment of the needle holder angle. In some embodiments, tubing is inserted into the insertion device 100 through the port 115 for the collection of blood following needle insertion. In some embodiments, the tubing is latex free, sterile, and rubber. In most embodiments, the tubing length is 18 inches. In some embodiments, the tubing length is about 26 inches. In some embodiments, the tubing length comprises a variety of lengths. In some embodiments, the diameter of the tubing is about 7 millimeters (mm) or about 9/32 inches, for example. In some embodiments, the diameter of the tubing comprises standard tubing diameters.

In some embodiments, the needle holder 138 is movable angular-wise and moves within the housing 122. In some embodiments, the needle holder 138 is angled at a needle holder angle 139 as shown in FIG. 3B. In some embodiments, the needle holder angle 139 ranges between about 0° to about 80°. In some embodiments, the needle holder angle 139 is at least about 0 degrees. In some embodiments, the needle holder angle 139 is at most about 80 degrees. In some embodiments, the needle holder angle 139 is about 0 degrees to about 5 degrees, about 0 degrees to about 10 degrees, about 0 degrees to about 15 degrees, about 0 degrees to about 20 degrees, about 0 degrees to about 25 degrees, about 0 degrees to about 30 degrees, about 0 degrees to about 35 degrees, about 0 degrees to about 40 degrees, about 0 degrees to about 45 degrees, about 0 degrees to about 50 degrees, about 0 degrees to about 55 degrees, about 0 degrees to about 60 degrees, about 0 degrees to about 65 degrees, about 0 degrees to about 70 degrees, about 0 degrees to about 75 degrees, or about 0 degrees to about 80 degrees.

In some embodiments, the needle holder angle 139 is about 5 degrees to about 10 degrees, about 5 degrees to about 15 degrees, about 5 degrees to about 20 degrees, about 5 degrees to about 25 degrees, about 5 degrees to about 30 degrees, about 5 degrees to about 35 degrees, about 5 degrees to about 40 degrees, about 5 degrees to about 45 degrees, about 5 degrees to about 50 degrees, about 5 degrees to about 55 degrees, about 5 degrees to about 60 degrees, about 5 degrees to about 65 degrees, about 5 degrees to about 70 degrees, about 5 degrees to about 75 degrees, or about 5 degrees to about 80 degrees.

In some embodiments, the needle holder angle 139 is about 10 degrees to about 15 degrees, about 10 degrees to about 20 degrees, about 10 degrees to about 25 degrees, about 10 degrees to about 30 degrees, about 10 degrees to about 35 degrees, about 10 degrees to about 40 degrees, about 10 degrees to about 45 degrees, about 10 degrees to about 50 degrees, about 10 degrees to about 55 degrees, about 10 degrees to about 60 degrees, about 10 degrees to about 65 degrees, about 10 degrees to about 70 degrees, about 10 degrees to about 75 degrees, or about 10 degrees to about 80 degrees.

In some embodiments, the needle holder angle 139 is about 15 degrees to about 20 degrees, about 15 degrees to about 25 degrees, about 15 degrees to about 30 degrees, about 15 degrees to about 35 degrees, about 15 degrees to about 40 degrees, about 15 degrees to about 45 degrees, about 15 degrees to about 50 degrees, about 15 degrees to about 55 degrees, about 15 degrees to about 60 degrees, about 15 degrees to about 65 degrees, about 15 degrees to about 70 degrees, about 15 degrees to about 75 degrees, or about 15 degrees to about 80 degrees.

In some embodiments, the needle holder angle 139 is about 20 degrees to about 25 degrees, about 20 degrees to about 30 degrees, about 20 degrees to about 35 degrees, about 20 degrees to about 40 degrees, about 20 degrees to about 45 degrees, about 20 degrees to about 50 degrees, about 20 degrees to about 55 degrees, about 20 degrees to about 60 degrees, about 20 degrees to about 65 degrees, about 20 degrees to about 70 degrees, about 20 degrees to about 75 degrees, or about 20 degrees to about 80 degrees.

In some embodiments, the needle holder angle 139 is about 25 degrees to about 30 degrees, about 25 degrees to about 35 degrees, about 25 degrees to about 40 degrees, about 25 degrees to about 45 degrees, about 25 degrees to about 50 degrees, about 25 degrees to about 55 degrees, about 25 degrees to about 60 degrees, about 25 degrees to about 65 degrees, about 25 degrees to about 70 degrees, about 25 degrees to about 75 degrees, or about 25 degrees to about 80 degrees.

In some embodiments, the needle holder angle is about 30 degrees to about 35 degrees, about 30 degrees to about 40 degrees, about 30 degrees to about 45 degrees, about 30 degrees to about 50 degrees, about 30 degrees to about 55 degrees, about 30 degrees to about 60 degrees, about 30 degrees to about 65 degrees, about 30 degrees to about 70 degrees, about 30 degrees to about 75 degrees, or about 30 degrees to about 80 degrees.

In some embodiments, the needle holder angle 139 is about 35 degrees to about 40 degrees, about 35 degrees to about 45 degrees, about 35 degrees to about 50 degrees, about 35 degrees to about 55 degrees, about 35 degrees to about 60 degrees, about 35 degrees to about 65 degrees, about 35 degrees to about 70 degrees, about 35 degrees to about 75 degrees, or about 35 degrees to about 80 degrees.

In some embodiments, the needle holder angle 139 is about 40 degrees to about 45 degrees, about 40 degrees to about 50 degrees, about 40 degrees to about 55 degrees, about 40 degrees to about 60 degrees, about 40 degrees to about 65 degrees, about 40 degrees to about 70 degrees, about 40 degrees to about 75 degrees, or about 40 degrees to about 80 degrees.

In some embodiments, the needle holder angle 139 is about 45 degrees to about 50 degrees, about 45 degrees to about 55 degrees, about 45 degrees to about 60 degrees, about 45 degrees to about 65 degrees, about 45 degrees to about 70 degrees, about 45 degrees to about 75 degrees, or about 45 degrees to about 80 degrees.

In some embodiments, the needle holder angle 139 is about 50 degrees to about 55 degrees, about 50 degrees to about 60 degrees, about 50 degrees to about 65 degrees, about 50 degrees to about 70 degrees, about 50 degrees to about 75 degrees, or about 50 degrees to about 80 degrees.

In some embodiments, the needle holder angle 139 is about 55 degrees to about 60 degrees, about 55 degrees to about 65 degrees, about 55 degrees to about 70 degrees, about 55 degrees to about 75 degrees, or about 55 degrees to about 80 degrees.

In some embodiments, the needle holder angle 139 is about 60 degrees to about 65 degrees, about 60 degrees to about 70 degrees, about 60 degrees to about 75 degrees, or about 60 degrees to about 80 degrees. In some embodiments, the needle holder angle is about 65 degrees to about 70 degrees, about 65 degrees to about 75 degrees, or about 65 degrees to about 80 degrees. In some embodiments, the needle holder angle is about 70 degrees to about 75 degrees or about 70 degrees to about 80 degrees. In some embodiments, the needle holder angle is about 75 degrees or about 75 degrees to about 80 degrees.

In some embodiments, the needle holder angle 139 is about 0 degrees. In some embodiments, the needle holder angle is about 1 degree. In some embodiments, the needle holder angle 139 is about 2 degrees. In some embodiments, the needle holder angle 139 is about 3 degrees. In some embodiments, the needle holder angle 139 is about 4 degrees. In some embodiments, the needle holder angle 139 is about 5 degrees. In some embodiments, the needle holder angle 139 is about 6 degrees. In some embodiments, the needle holder angle 139 is about 7 degrees. In some embodiments, the needle holder angle 139 is about 8 degrees. In some embodiments, the needle holder angle 139 is about 9 degrees. In some embodiments, the needle holder angle 139 is about 10 degrees. In some embodiments, the needle holder angle 139 is about 11 degrees. In some embodiments, the needle holder angle 139 is about 12 degrees. In some embodiments, the needle holder angle 139 is about 13 degrees. In some embodiments, the needle holder angle 139 is about 14 degrees. In some embodiments, the needle holder angle 139 is about 15 degrees. In some embodiments, the needle holder angle 139 is about 16 degrees. In some embodiments, the needle holder angle 139 is about 17 degrees. In some embodiments, the needle holder angle 139 is about 18 degrees. In some embodiments, the needle holder angle 139 is about 19 degrees. In some embodiments, the needle holder angle 139 is about 20 degrees. In some embodiments, the needle holder angle 139 is about 21 degrees. In some embodiments, the needle holder angle 139 is about 22 degrees. In some embodiments, the needle holder angle 139 is about 23 degrees. In some embodiments, the needle holder angle 139 is about 24 degrees. In some embodiments, the needle holder angle 139 is about 25 degrees. In some embodiments, the needle holder angle 139 is about 26 degrees. In some embodiments, the needle holder angle 139 is about 27 degrees. In some embodiments, the needle holder angle 139 is about 28 degrees. In some embodiments, the needle holder angle 139 is about 29 degrees. In some embodiments, the needle holder angle 139 is about 30 degrees. In some embodiments, the needle holder angle 139 is about 31 degrees. In some embodiments, the needle holder angle 139 is about 32 degrees. In some embodiments, the needle holder angle 139 is about 33 degrees. In some embodiments, the needle holder angle 139 is about 34 degrees. In some embodiments, the needle holder angle 139 is about 35 degrees. In some embodiments, the needle holder angle 139 is about 36 degrees. In some embodiments, the needle holder angle 139 is about 37 degrees. In some embodiments, the needle holder angle 139 is about 38 degrees. In some embodiments, the needle holder angle 139 is about 39 degrees. In some embodiments, the needle holder angle 139 is about 40 degrees. In some embodiments, the needle holder angle 139 is about 41 degrees. In some embodiments, the needle holder angle 139 is about 42 degrees. In some embodiments, the needle holder angle 139 is about 43 degrees.

In some embodiments, the needle holder angle 139 is about 44 degrees. In some embodiments, the needle holder angle 139 is about 45 degrees. In some embodiments, the needle holder angle 139 is about 46 degrees. In some embodiments, the needle holder angle 139 is about 47 degrees. In some embodiments, the needle holder angle 139 is about 48 degrees. In some embodiments, the needle holder angle 139 is about 49 degrees. In some embodiments, the needle holder angle is about 50 degrees. In some embodiments, the needle holder angle 139 is about 51 degrees. In some embodiments, the needle holder angle 139 is about 52 degrees. In some embodiments, the needle holder angle 139 is about 53 degrees. In some embodiments, the needle holder angle 139 is about 54 degrees. In some embodiments, the needle holder angle 139 is about 55 degrees. In some embodiments, the needle holder angle 139 is about 56 degrees. In some embodiments, the needle holder angle 139 is about 57 degrees. In some embodiments, the needle holder angle 139 is about 58 degrees. In some embodiments, the needle holder angle 139 is about 59 degrees. In some embodiments, the needle holder angle 139 is about 60 degrees. In some embodiments, the needle holder angle 139 is about 61 degrees. In some embodiments, the needle holder angle 139 is about 62 degrees. In some embodiments, the needle holder angle 139 is about 63 degrees. In some embodiments, the needle holder angle 139 is about 64 degrees. In some embodiments, the needle holder angle 139 is about 65 degrees. In some embodiments, the needle holder angle 139 is about 66 degrees. In some embodiments, the needle holder angle 139 is about 67 degrees. In some embodiments, the needle holder angle 139 is about 68 degrees. In some embodiments, the needle holder angle 139 is about 69 degrees. In some embodiments, the needle holder angle 139 is about 70 degrees. In some embodiments, the needle holder angle is about 71 degrees. In some embodiments, the needle holder angle 139 is about 72 degrees. In some embodiments, the needle holder angle 139 is about 73 degrees. In some embodiments, the needle holder angle 139 is about 74 degrees. In some embodiments, the needle holder angle 139 is about 75 degrees. In some embodiments, the needle holder angle 139 is about 76 degrees. In some embodiments, the needle holder angle 139 is about 77 degrees. In some embodiments, the needle holder angle 139 is about 78 degrees. In some embodiments, the needle holder angle 139 is about 79 degrees. In some embodiments, the needle holder angle 139 is about 80 degrees.

Needle Drive Assembly

Proper needle insertion operation can require control of the insertion speed and needle position relative to the installed cartridge. In some embodiments, the insertion device comprises a needle drive assembly to control the insertion speed of the needle. The needle drive assembly may allow for guide wire placement.

Figure 15:
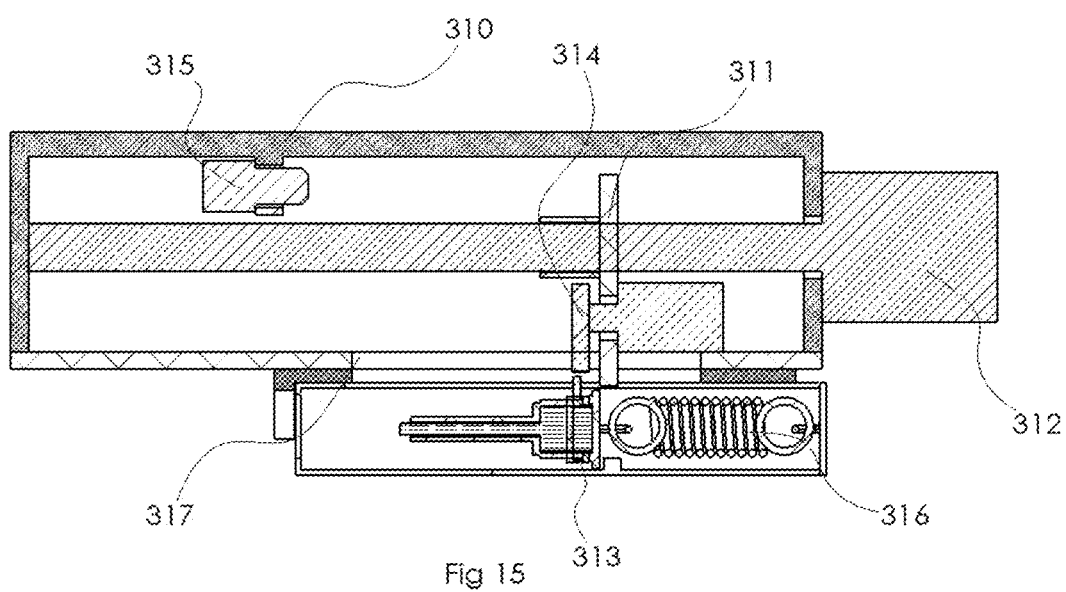
FIG. 15 illustrates a cross-sectional view of a needle drive assembly with drive mechanism for the insertion of the needle and/or catheter.

FIG. 15 illustrates the needle drive assembly 310, which can move the needle and/or catheter to the target location in a linear fashion through the drive mechanism 311. In some embodiments, the drive mechanism 311 comprises a lead screw/nut combination. In other embodiments, the drive mechanism comprises on a rack and pinion. In other embodiments, the drive mechanism comprises a belt or chain drive. In some embodiments, the drive mechanism comprises a linear rail. In some embodiments, the drive mechanism comprises a rod and bushing combination. In some embodiments, the drive mechanism comprises a cable driver. In other embodiments, the mechanism is any combination thereof. In some embodiments, the insertion by the needle drive assembly 310 is driven with a stepper motor and lead screw 312. In other embodiments, the needle is be driven by an electrical linear actuator. In other embodiments, the insertion is controlled using a piezo electric linear motor. In other embodiments, the actuator is a servo motor connected to a cam system. In other embodiments, the needle is controlled using a magnetic drive system. In other embodiments, the needle drive assembly is based on any combination thereof.

In some embodiments, the needle drive assembly 310 comprises a releasing mechanism 313 to safely detach the catheter from the needle after the insertion and prior to the removal of the device. In certain embodiments, releasing mechanism is mechanically triggered by a lever or push button on the side of the device. In other embodiments, releasing mechanism is electrically triggered by a user engaging an actuator 314. In other embodiments the releasing mechanism is triggered via an electrical needle/catheter stopper 315. In other embodiments, releasing mechanism is automatically triggered via a software algorithm.

In some embodiments, the releasing mechanism comprises a spring-driven quick release 316, in which a preloaded spring connected to the needle is released to withdraw the needle after insertion, thereby removing the catheter from the needle. In other embodiments, the catheter releasing mechanism comprises a solenoid. In other embodiments, catheter releasing mechanism comprises a cam connected to a servomotor. In other embodiments, the catheter is manually removed by the user. In other embodiments, the catheter releasing mechanism is pneumatic. In other embodiments, the catheter releasing mechanism is based on any combination thereof.

The insertion device may comprise needle/catheter stopper to prevent the needle from being inserted too far into the patient or beyond the safety limits. The degree of safety provided by the needle/catheter stopper may be manually adjusted or calibrated by the user or automatically defined by the device and the ultrasound image. The degree of safety may depend on the depth of insertion by the needle and/or catheter.

In some embodiments the needle drive assembly comprises mechanical needle/catheter stopper 317 to prevent the needle/catheter from moving beyond its intended range of motion. In other embodiments, the needle/catheter stopper comprises electrical limit switches 315. In other embodiments, the needle/catheter stopper comprises optical flags. In other embodiments, the needle/catheter stopper 317 is operatively connected to the drive mechanism 311. In other embodiments, the needle/catheter stopper is manually set by a user to maintain at least certain degree of safety. In some embodiments, the needle/catheter stopper is set by the manufacturer. In other embodiments, the needle/catheter stopper varies depending on the type of cartridge installed into the insertion unit. In other embodiments, the needle/catheter stopper is set automatically by the insertion device through image recognition of the target anatomy. In other embodiments, the needle/catheter stopper is any combination thereof.

The needle drive assembly can have a control for the user to initiate and/or end the needle insertion. In some embodiments, the control of the needle drive assembly may allow abortion of the insertion at any time. The needle drive assembly may not be automated. In other embodiments, the control may not allow abortion of needle insertion at any time. The needle drive assembly can be automated.

In some embodiments, the needle drive assembly is driven directly using a one to one mechanical control by the user. In some embodiments, the one to one control allows for direct feedback to the needle during insertion. In some embodiments, the control mechanism allows visualization of the needle during insertion through a window or a view port. In other embodiments, the one to one control allows for a visual gauge to determine penetration depth of the needle. In some embodiments, the one to one mechanical control comprises adjustable mechanical needle/catheter stopper. In some embodiments, the user may not stop needle insertion by manually withdrawing the control mechanism. In some embodiments, the user controls the insertion using electrical switches in a one to one motion. The electrical switches can be scaled up or scaled down to adjust the speed of needle insertion. In some embodiments, the device comprises an abort control mechanism that immediately retracts the needle.

The insertion device can comprise a force detector to determine the opposing force acting upon the needle from tissue being pierced. The force acting upon the needle may change depending on the density of the pierced tissue. This change in detected force may be used to determine the type of the subdermal tissue layer the needle is in and may aid in identifying when the needle enters the lumen of a vessel.

In some embodiments, the device contains a method of detecting required force for penetration of the needle through its given medium. In some embodiments, the force is determined from a pressure transducer. In other embodiments, the force is determined from motor drive current. In other embodiments, force is detected using a strain gauge. In yet other embodiments, the force is calculated in any combination thereof.

Needle Stage

In some embodiments, the insertion device comprises a needle stage to position the needle holder in preparation for the needle insertion. The needle stage may comprise a series of actuators around a specific coordinate system in order to obtain the required degrees of freedom for insertion. The coordinate system can require at least two, three, four, or five degrees of freedom that can allow the needle to puncture the skin at the required orientation for an intravenous insertion, with positional feedback from the ultrasound. The needle stage can then reduce the angle between needle and the vein's central axis, while maintaining the needle tip position within the lumen using reverse kinematics equations. The needle stage can further allow the needle to be advanced along the length of the lumen of the vein while maintaining a central position within the lumen.

Figure 13:
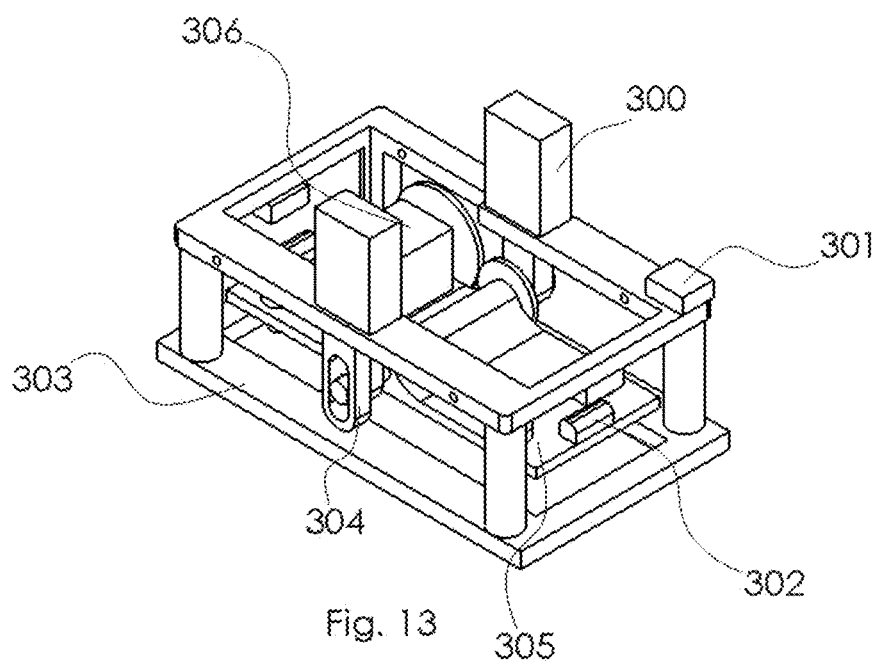
FIG. 13 illustrates a front perspective view of a needle stage with components for the rotation and height adjustment.

FIG. 13 shows the needle stage 303 and the components used for the rotation and height adjustment of the needle holder and/or the cartridge. In some embodiments, the rotation and adjustment mechanisms are based around a Cartesian coordinate system. In other embodiments, the mechanisms are based around a polar coordinate system. In some embodiments, the mechanisms are based around four-bar linkage mechanisms. In some embodiments, the mechanisms are based on a gimbal type mechanism. In other embodiments, the mechanisms are based on any combination thereof.

In some embodiments, the needle holder operatively connected to needle stage 303 is positioned using linear actuators 300. In other embodiments, the needle holder is positioned using stepper motors. In some embodiments, the needle holder is positioned using a stepper motor in combination with a lead screw. In other embodiments, the needle holder is positioned using servo motors 306. In other embodiments, the needle holder is positioned using a DC motor with an encoder. In other embodiments, the needle holder is positioned using a piezoelectric actuator. In other embodiments, the needle holder is positioned based on any combination thereof.

In some embodiments the needle stage 303 is coupled to the actuators using a series of spur, helical or worm gears. In other embodiments, the needle stage 303 mechanisms comprises a series of belts used to couple the actuators to the needle holder. In other embodiments, the needle stage is coupled to the actuators using a series of spur, helical or worm gears. In other embodiments, the needle stage is directly coupled to the shaft of the motors using a motor coupler. In other embodiments, the needle stage is coupled to the actuators using a series of cables. In other embodiments, the actuators are coupled to the needle holder based on any combination thereof.

In some embodiments the needle stage 303 comprises mechanical stoppers 304 to prevent the needle holder from moving beyond its intended range of motion. In some embodiments, the stoppers comprise electrical limit switches. In other embodiments, the stoppers comprise optical flags. In other embodiments, the stoppers are operatively connected to a drive mechanism. In some embodiments, the stopper is manually set by a user. In some embodiments, the stoppers are set by the manufacturer. In some embodiments, different stoppers can be used depending on the type of cartridge installed into the device. In other embodiments, the stoppers are any combination thereof.

The needle stage can be driven by a combination of prismatic and rotary actuators/joints. Each combination can create a three degrees of freedom (DOF) system capable of successfully creating the required insertion path based on actuator output and target anatomy location. Examples of the possible combination of actuators are given in Table 1. Beyond the simple three DOF systems, other mechanical mechanisms can take additional forms including: 4 bar linkages, alternative Cartesian systems, and hexapod actuators.

TABLE 1

3 DOF Mechanism Combinations Needle Stage

| First Joint | Second Joint | Third Joint |
| --- | --- | --- |
| Rotary | Rotary | Rotary |
| Rotary | Rotary | Prismatic |
| Rotary | Prismatic | Rotary |
| Prismatic | Rotary | Rotary |
| Rotary | Prismatic | Prismatic |
| Prismatic | Rotary | Prismatic |
| Prismatic | Prismatic | Rotary |

Figure 17A:
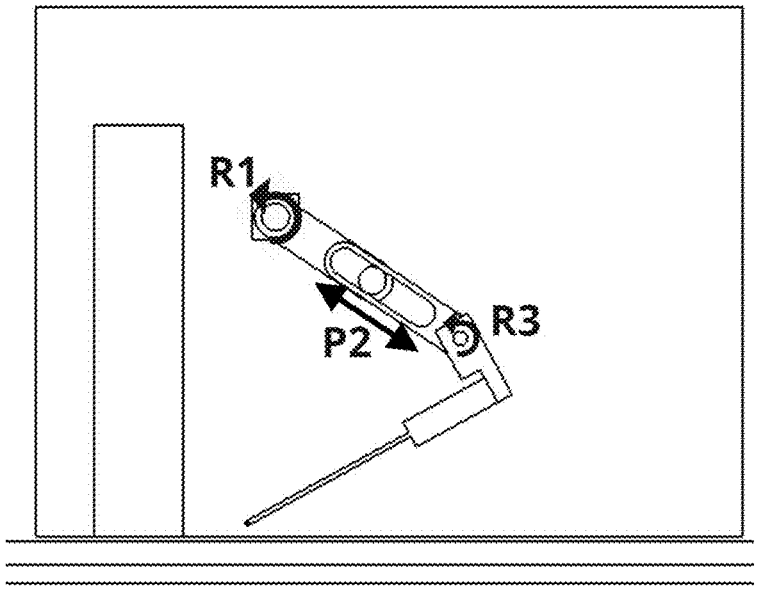
FIGS. 17A-17E illustrates a three degrees of freedom (DOF) mechanism with three joints.
Figure 17B:
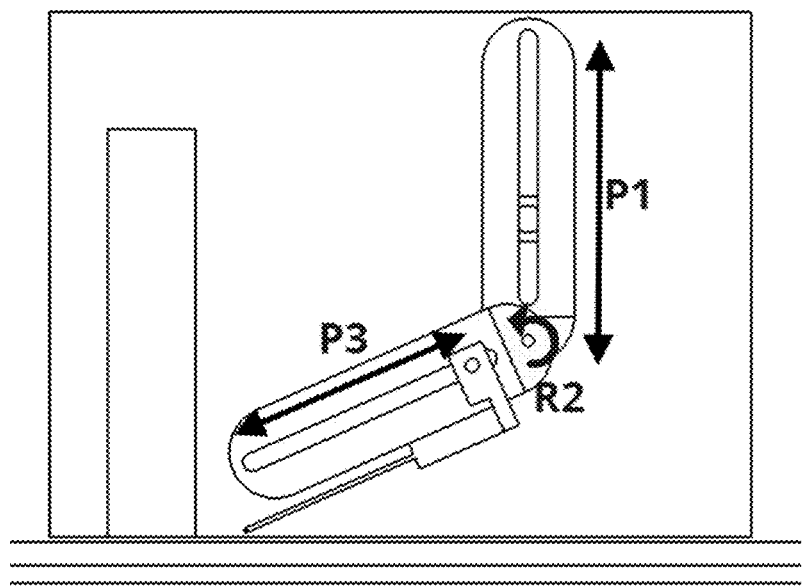
Figure 17C:
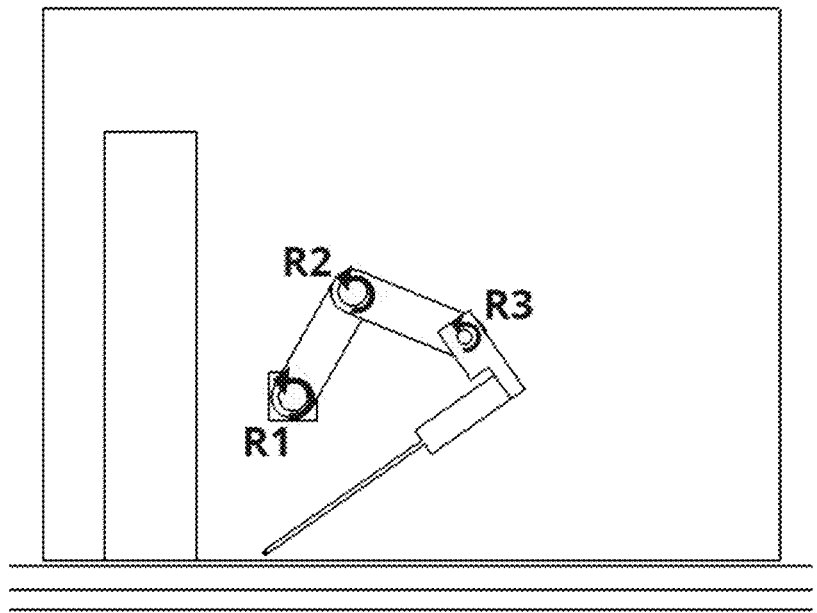
Figure 17D:
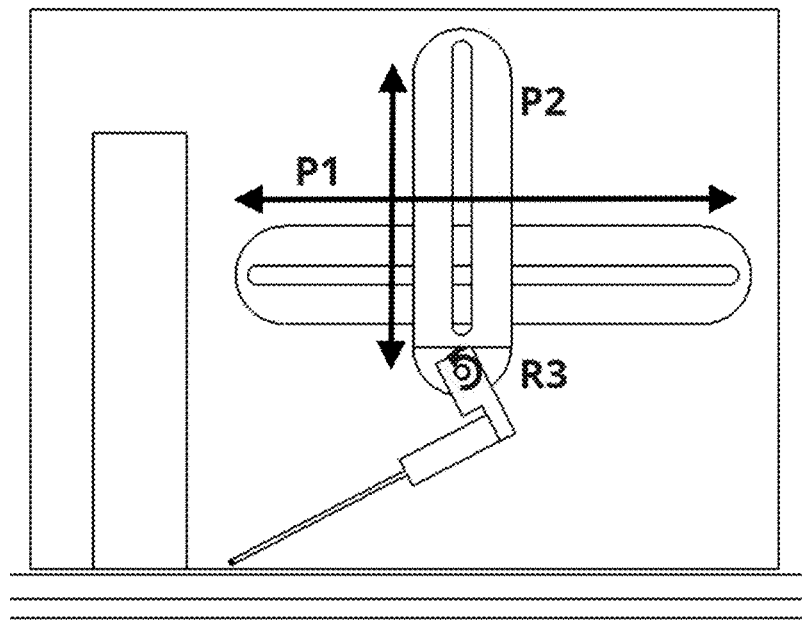
Figure 17E:
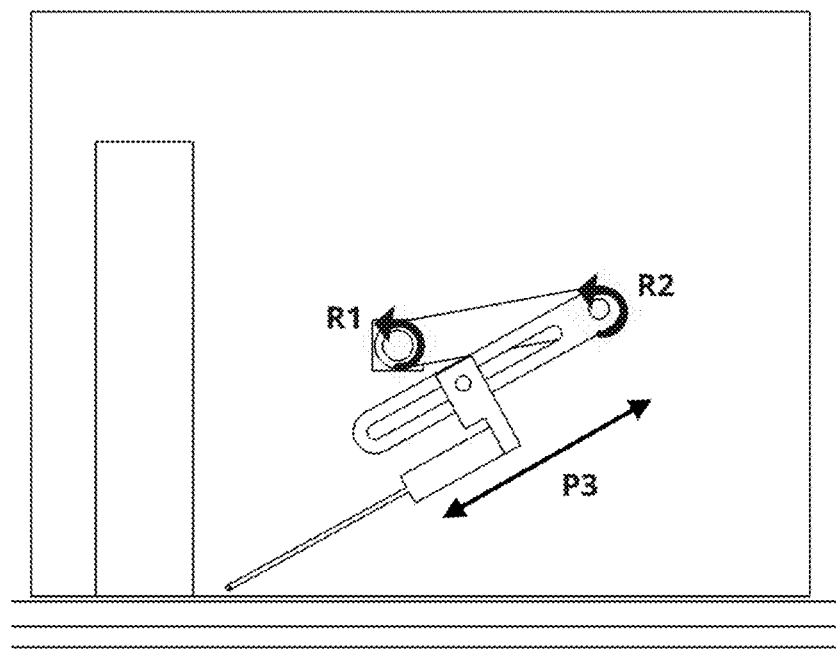

The three DOF system can comprise three mechanical joints. In some embodiments, the first, second, and third joints can be rotary R1, prismatic P2, and rotary R3, respectively (FIG. 17A). In another embodiment, the first, second, and third joints can be prismatic P1, rotary R2, and prismatic P3, respectively (FIG. 17B). In certain embodiments, the first, second, and third joints (R1, R2, and R3) can be all rotaries (FIG. 17C). In yet another embodiment, the first, second, and third joints can be prismatic P1, prismatic P2, rotary R3 (FIG. 17D). The first, second, and third joints can be rotary R1, rotary R2, and prismatic P3, respectively (FIG. 17E).

Prior to the needle insertion, the needle stage may be calibrated for the needle position with respect to the needle stage. The calibration process can be manual or automatic. An automatic calibration may involve an initial homing routine for the stage and the cartridge after installing the cartridge in the insertion device. The calibration can define the position of the needle tip prior to each insertion for reliability and safety of the device.

Figure 14:
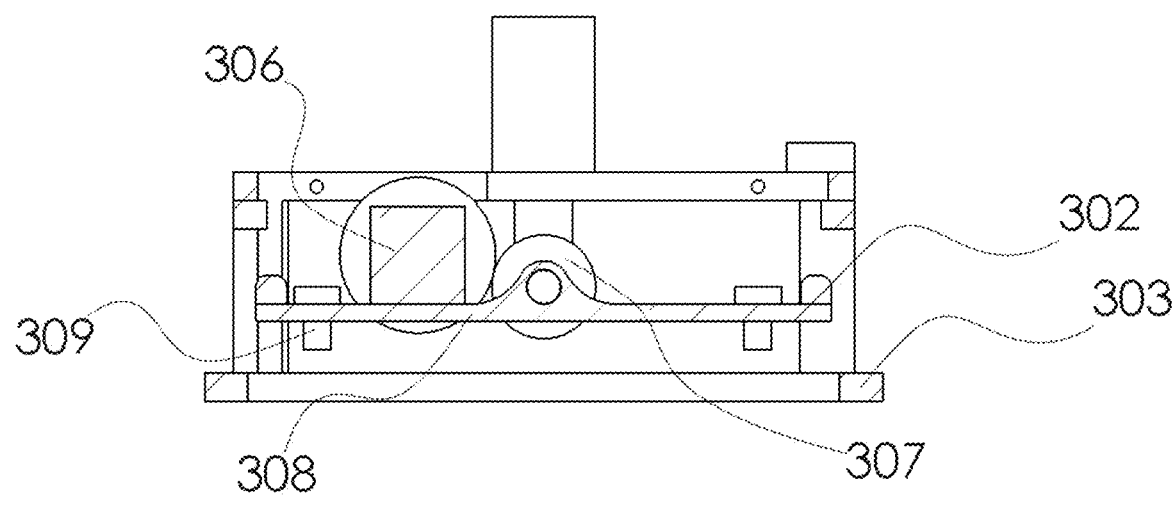
FIG. 14 illustrates a cross-sectional view of the needle stage shown in FIG. 13.

FIG. 14 illustrates a cross-sectional view of the needle stage and the mechanisms involved for homing the devices position. In some embodiments, the needle stage homing mechanism 302 calibrates its position to a reference frame using magnetic hall effect sensors. In other embodiments, the sensors are optical switches. In other embodiments, the sensors are mechanical limit switches. In some embodiments, the sensors can be combination of optical switches and mechanical limit switches. In some embodiments, the device is calibrated at the factory. In some embodiments, the device performs a calibration routine prior to each insertion.

In some embodiments, the needle stage 303 couples directly to the needle drive assembly by fasteners 309 (FIG. 14). In other embodiments, the needle stage and the needle drive assembly are built on the same body. In some embodiments, the position of the needle drive assembly is calibrated prior to insertion using the tip of the needle and a limit switch. In other embodiments, the position of the assembly is calibrated using a hall-effect sensor. In some embodiments, the tip of the needle is detected using the ultrasound internal to the device.

The needle stage may be calibrated to match the position of the needle and/or needle stage with respect to the ultrasound probe and in the corresponding image. A calibration can be done between the needle stage and the ultrasound to quantify the offset between the needle tip and the ultrasound plane. Prior to the needle insertion, the offset can be defined with reference to a physical point on the device.

To ensure a safe needle insertion, the needle stage may comprise one or more false insertion sensors to detect unacceptable levels of shock or vibration, either during or outside an insertion procedure.

In some embodiments, the device comprises false insertion sensors to detect shock or vibration above or below certain thresholds. The insertion procedure can be aborted when the shock or vibration reaches unacceptable levels to avoid false insertion, i.e. insertion into unintended target. In some embodiments, the false insertion sensors can continuously to detect any drop or impact that may affect the device's performance.

Vacuum Connection

In some embodiments, the insertion device comprises a vacuum connection. In some embodiments, the vacuum connection is located within the housing. In some embodiments, the vacuum connection comprises a vacuum connector. In some embodiments, the vacuum connection comprises a vacuum source. In some embodiments, the vacuum connection is operatively attached to the cartridge. In some embodiments, the vacuum connector is operatively attached to the cartridge. In some embodiments, the vacuum connection and the vacuum connector are operatively attached to the cartridge. In some embodiments, the vacuum connector is in vacuum communication with a vacuum source. In some embodiments, the vacuum source is configured to draw air through the needle holder opening. In some embodiments, the vacuum source is configured to draw air through the bottom surface of the cartridge.

In some embodiments, the cartridge 234 comprises a suction area 210. In some embodiments, the suction area 210 is the entire base of the cartridge. Alternatively, in some embodiments, the shape of the suction area 210 is a shape that serves to increase the likelihood of successful cannulation of the target tissue. For example, in some embodiments, the suction area 210 is a linear area of suction on the distal end of the insertion device (e.g., of the cartridge) that causes a tourniquet-like action on underlying tissue and vessels, thereby distending the portion of a lumen of one or more blood vessels in the target tissue.

In some embodiments, the suction is created by a vacuum source within the insertion device itself. In some embodiments, the vacuum source is a vacuum motor. In some embodiments, the vacuum motor creates a vacuum between the insertion device and a flexible portion of the cartridge, thereby creating a vacuum between the cartridge and the surface of the skin of the patient. In some embodiments, the suction is created by a pneumatic manipulation of the insertion device on a flexible portion of the cartridge (i.e., the vacuum button and/or the vacuum bulb described elsewhere herein). In some embodiments, the suction is created by a pneumatic manipulation of one or more one-way suction valves, thereby creating a vacuum between the cartridge and the surface of the skin of the patient.

In some embodiments, the suction is created by mechanical manipulation of the insertion device on the cartridge by a plurality of one-way valves and bulbs. In some embodiments, the plurality of one-way valves and bulbs transmit a force on interconnected flexible portions of the cartridge base, such that a vacuum action is created under the cartridge. In some embodiments, the suction is created by mechanical manipulation directly on the cartridge by the user. For example, in some embodiments, the user mechanically manipulates a bulb connected to one or more one-way valves, thereby creating a vacuum transmitted directly to the surface of the skin of the patient. Alternatively, in some embodiments, the vacuum is transmitted to the flexible portion of the cartridge, thereby creating a vacuum between the cartridge and the surface of the skin of the patient.

In some embodiments, the shape of the suction area is changed and/or adjusted during the course of an insertion procedure, such that it maximizes that success of the procedure (e.g., targeting the target tissue location). In some embodiments, the intensity of the suction is changed and/or adjusted during the course of an insertion procedure, such that it maximizes that success of the procedure (e.g., targeting the target tissue location).

In some embodiments, a suction device is connected to the cartridge. In some embodiments, the suction device is located externally with respect to the insertion device and the cartridge. In some embodiments, the suction device is used to create a vacuum for a medical procedure (e.g., a needle insertion). In some embodiments, the suction is created by mechanical manipulation of the suction device on the cartridge. For example, in some embodiments, the cartridge comprises flexible components that are integrated with rigid components that are pulled, in order to create a suction cup-like action. In some embodiments, the cartridge comprises the suction device. In some embodiments, having the suction device located within the cartridge (as opposed to having the suction device located within the housing of the insertion device) prevents and/or ameliorates the risk of a potential contamination of the insertion device (e.g., accidental suction of blood from the surface of the skin and into the insertion device). Furthermore, in some embodiments, the insertion device comprises an actuator that activates the suction device (e.g., depresses the vacuum button and/or vacuum bulb). In some embodiments, the actuator comprises a barrier (e.g., a casing) that protects it from a potential contamination (e.g., a blood contamination). In some embodiments, the automatic activation of the suction device by the actuator prevents and/or decreases the risk of user error when activating the suction device (e.g., the user not deactivating suction when blood is present on the surface of the skin). In some embodiments, the automatic activation of the suction device by the actuator prevents and/or decreases the risk of a potential contamination of the insertion device (e.g., a blood contamination) caused by user error.

Power Source

In some embodiments, the vacuum-assisted insertion device comprises a power source. In some embodiments, the power source is configured to power the ultrasound probe. In some embodiments, the power source is configured to power a vacuum source. In some embodiments, the power source is configured to power the display and/or electronics of the insertion device.

In some embodiments, the insertion device is portable. In some embodiments, the portable insertion device is powered by a battery. In some embodiments, the power source is a battery. In some embodiments, the battery is a rechargeable battery. In some embodiments, the battery is a removable battery. In some embodiments, the battery is an internal battery. In some embodiments, the battery is a non-removable battery. Non-limiting examples of a battery include a nickel cadmium (NiCd) battery, nickel-metal hydride (NiMH) battery, a nickel zinc (NiZn) battery, a lead acid battery, a lithium ion battery (Li-ion), or a lithium ion polymer (Li-ion polymer) battery. In some embodiments, the power source comprises a capacitor. In some embodiments, the power source is connected to the insertion device by a cable. In some embodiments, the power source comprises a power supply. In some embodiments, the power supply adjusts and regulates the power received from the power source. In some embodiments, the power supply provides electricity to the insertion device. In some embodiments, the power supply outputs a voltage to the insertion device. In some embodiments, the power supply regulates an output voltage.

Needle Types

In some embodiments, the medical device being introduced by the insertion device is a needle. In some embodiments, the needle is an introducer needle, a biopsy needle, or a needle trocar. In some embodiments, the needle comprises a catheter and/or a guidewire. In some embodiments, the catheter is a peripherally inserted central catheter (PICC). In some embodiments, the devices and systems disclosed herein facilitate the insertion of a peripherally inserted central catheter. In some embodiments, the catheter is a percutaneous indwelling central catheter. In some embodiments, the devices and systems disclosed herein facilitate the insertion of a percutaneous indwelling central catheter. In some embodiments, the catheter is a peripherally inserted central catheter, a central venous catheter, a urinary catheter, an arterial catheter, a venous catheter, a tunneled catheter, a port catheter, or a non-tunneled central catheter. In some embodiments, the needle is a winged steel or butterfly needle. In some embodiments, the needle comprises a syringe. In some embodiments, the needle is a single-use, hypodermic needle. In some embodiments, the needle is in fluid connection with a collection tube. In some embodiments, the collection tube is an evacuated tube. In some embodiments, the collection tube is a blood collection tube. In some embodiments, the collection tube is a vacutainer blood collection tube. In some embodiments, the needle is in flow communication with a fluid injection line. In some embodiments, the needle is a 6-gauge needle, an 8-gauge needle, a 13-gauge needle, a 15-gauge needle, a 17-gauge needle, an 18-gauge needle, a 19-gauge needle, a 20-gauge needle, a 21-gauge needle, a 22-gauge needle, a 23-gauge needle, a 24-gauge needle, a 25-gauge needle, a 26-gauge needle, a 27-gauge needle, a 28-gauge needle, a 29-gauge needle, a 30-gauge needle, a 31-gauge needle, or a 32-gauge needle. In some embodiments, the needle is a needle ranging between about 1 to about 10 inches in length. In some embodiments, the needle contains a stylet, also known as an obturator or an introducer, which is a fine wire, a slender probe, or a solid rod with a metal hub fitted to match a bevel of a needle.

Needle Insertion Methods

Disclosed herein, in certain embodiments, are methods for introducing a needle into a target tissue in an individual in need thereof using the insertion device. In some embodiments, the insertion device is configured to generate and/or transmit one or more imaging modalities and comprises medical instrumentation that is remotely manipulated by a user. In some embodiments, the insertion device is configured to generate and/or transmit one or more imaging modalities and comprises medical instrumentation that is not remotely manipulated by a user.

In some embodiments, the user selects the cartridge that is applicable to the medical procedure that will be carried out (e.g., one of the cartridges shown in FIG. 5). In some embodiments, first, the method comprises securing the cartridge to the cartridge receiver. In some embodiments, the user mechanically secures the cartridge 134 to the cartridge receiver 118. In some embodiments, the user uses a snap-on mechanism to attach the cartridge 134 to the cartridge receiver 118. In some embodiments, the method comprises using a reversible attachment mechanism to allow for temporary attachment of the cartridge 134 to the cartridge receiver 118. In some embodiments, the method comprises securing the cartridge 134 to the cartridge receiver 118 using a prong-attachment system. In some embodiments, the method comprises securing the cartridge 134 to the cartridge receiver 118 by using one or more chemicals. In some embodiments, the one or more chemical means comprise one or more chemicals that allow for adhesion (e.g., an adhesive). In some embodiments, the method comprises securing the cartridge 134 to the cartridge receiver 118 by using one or more magnets.

Next, in some embodiments, the method comprises imaging the target tissue using the ultrasound probe and the infrared sensor by contacting the surface of the skin of the individual with the bottom surface of the cartridge. In some embodiments, the user uses the ultrasound probe to target the tissue. In some embodiments, the user activates the infrared sensor to target the tissue. In some embodiments, the user obtains an ultrasound and/or infrared image by contacting the skin of the individual with the bottom surface of the cartridge. In some embodiments, the user images the target tissue remotely.

Next, in some embodiments, the method comprises identifying the needle insertion point on the display screen. In some embodiments, the user identifies the needle insertion point via the indicator marking 128 on the display screen. In some embodiments, the user actives a vacuum source to create a negative pressure around the target tissue insertion area at the surface of the skin of the patient. In some embodiments, the vacuum source provides tension within an area of suction. In some embodiments, a vacuum suction pump motor is activated to create suction. In some embodiments, the user activates a vacuum source via depression of a physical button or activation of a switch on the insertion device. In some embodiments, the amount of negative pressure applied to the surface of the skin of the patient is automatically regulated by the insertion device. For example, in some embodiments, the insertion device outputs the negative pressure applied on the display screen. In some embodiments, the computing device of the insertion device uses a feedback loop system to automatically regulate, activate, and/or deactivate a vacuum source. In some embodiments, the vacuum suction pump motor exerts a pulling force against the skin of the individual. In some embodiments, the vacuum source replicates the physical tension typically and mechanically induced by a health care worker (e.g., by holding the skin of the patient taut and/or by using a tourniquet prior to insertion of a needle).

Next, in some embodiments, the method comprises adjusting the needle holder angle and moving the needle longitudinally, through the cartridge inlet, thereby introducing the needle at the needle insertion point and into the target tissue. In some embodiments, adjusting the needle holder angle and moving the needle longitudinally are manually actuated. In some embodiments, adjusting the needle holder angle and moving the needle longitudinally are remotely actuated. In some embodiments, adjusting the needle holder angle and moving the needle longitudinally are automatically actuated by the computing device. In some embodiments, the method comprises administering a therapeutic agent using the needle. In some embodiments, the method comprises collecting a biopsy sample using the needle. In some embodiments, the method comprises inserting a guidewire into the target tissue. In some embodiments, the method comprises retracting the guidewire from the target tissue. In some embodiments, the method comprises inserting the catheter into the target tissue. In some embodiments, the method comprises retracting the catheter from the target tissue.

In some embodiments, the user implements the user interface to adjust the longitudinal location of the needle. In some embodiments, the user implements the user interface to adjust the needle holder angle via an angle actuator. In some embodiments, the user interface (e.g., the display screen, the gear wheel, or the positioning dial) of the insertion device is used to adjust the longitudinal location of the needle and/or the needle holder angle. In some embodiments, the user initially adjusts the longitudinal location via the user interface. In some embodiments, the user proceeds by adjusting the angle of the needle. In some embodiments, the user introduces the needle at the selected insertion point and into the target tissue. In some embodiments, the user inserts the needle into the selected tissue via the needle insertion button. In some embodiments, the user uses a digital selection method via the display screen to adjust the location, angle, and/or position of the needle. In some embodiments, the needle is guided and/or inserted into the target tissue via the vacuum-assisted insertion system. For example, in some embodiments, the user turns on the vacuum source in order to create vacuum between the insertion device and the cartridge, thereby creating a vacuum between the cartridge and the skin of the patient. In some embodiments, the suction is created by mechanical manipulation of the insertion device and the cartridge. For example, in some embodiments, the cartridge comprises flexible features integrated with more rigid elements that when pulled away from the patient, they create a suction cup-like action.

The method can further comprise adjusting the position of the needle holder with respect to the needle stage. The needle stage may comprise a series of actuators around a specific coordinate system in order to obtain the required degrees of freedom for insertion. The coordinate system can require at least two, three, four, or five degrees of freedom that can allow the needle to puncture the skin at the required orientation for an intravenous insertion, with positional feedback from the ultrasound. The needle stage can then reduce the angle between needle and the vein's central axis, while maintaining the needle tip position within the lumen using reverse kinematics equations. The needle stage can further allow the needle to be advanced along the length of the lumen of the vein while maintaining a central position within the lumen.

In some embodiment, it may be possible that the force applied on the needle results in deflection of the needle tip off its central axis during the insertion. A longitudinal ultrasound scan can allow the needle deflection to be visually recognized and insertion path adjusted in real time either automatically or manually.

In some embodiments, the needle insertion system can visually interpret in real-time the current position and deflection of the needle tip using a combination of longitudinal and transverse ultrasound scans. In some embodiments, the interpretation is used to compensate error in the insertion position. In some embodiment, the interpretation is used as a visual indicator for the operator, allowing them to adjust the needle. In other embodiments, the interpretation is used in any combination thereof.

In some embodiments, the imaging stage can be used to manipulate the position of the ultrasound probe and the infrared sensor with respect to the housing. During insertion and once the tip of the needle has entered the vessel lumen, the user may adjust the imaging stage to move the ultrasound probe and the infrared sensor to locate a second target. The second target may be an advanced section along the length of a vessel lumen. The needle stage can be adjusted to allow the needle to move to the advanced section while maintaining a central position within the lumen. The needle can be pivoted co-axially with the vessel and can subsequently release the catheter. To minimize the risk of tearing the outer wall of the vessel during the pivoting process, the insertion system can create a virtual pivot point at or around the intersection of the vessel wall and the needle. In another embodiment, the needle can be pivoted about the needle tip. In some embodiments, the device can interpret the ultrasound image to create a virtual pivot point at or around an intersection of the vein wall (tunica externa) and the needle body in order to minimize the risk of tearing the tunica externa during the insertion process.

Disclosed herein, in some embodiments, are methods of sampling venous blood using the insertion device. In some embodiments, the method comprises securing the cartridge to the cartridge receiver. In some embodiments, the step of securing the cartridge to the cartridge receiver comprises a snap-on mechanism. In some embodiments, the step of securing the cartridge to the cartridge receiver comprises a reversible attachment mechanism. In some embodiments, the step of securing the cartridge to the cartridge receiver comprises a prong-attachment mechanism. In some embodiments, the step of securing the cartridge to the cartridge receiver comprises chemical adhesion.

Next, in some embodiments, the method comprises securing an evacuated collection tube to the cartridge receiver. In some embodiments, the user threads the collection tube through the port and into insertion device. In some embodiments, the tube is previously attached to the needle and requires no additional insertion steps by the user. Next, in some embodiments, the method comprises imaging a blood vessel using the ultrasound probe and the infrared sensor by contacting the skin of the individual with the bottom surface of the cartridge. In some embodiments, the user is guided by the ultrasound and/or infrared images displayed on the display screen. In some embodiments, the ultrasound and/or infrared images displayed on the display screen are displayed in real time. In some embodiments, the image displayed on the display screen comprise an indicator line and/or an indicator marking that indicates the target tissue location and/or the location of the needle in real time. Next, in some embodiments, the method comprises identifying the needle insertion point on the display screen. In some embodiments, the user identifies the needle insertion point via the indicator line and/or the indicator marking on the display screen. In some embodiments, the user actives the vacuum source to draw air through the cartridge inlet. In some embodiments, the vacuum source provides tension within the area of suction. In some embodiments, the vacuum motor is activated by the user. In some embodiments, the user activates the vacuum motor by depressing a physical button and/or activating a switch on the interface of the insertion device. In some embodiments, the vacuum source is automatically activated by the computing device of the insertion device.

Next, in some embodiments, the method comprises adjusting the syringe holder angle and moving the needle longitudinally, through the cartridge inlet, thereby introducing the needle at the needle insertion point and into the blood vessel. Next, in some embodiments, the method comprises collecting venous blood from the individual into the evacuated collection tube.

Described herein, in some embodiments, are methods for introducing a catheter into a target tissue in an individual in need thereof, using the insertion device. First, in some embodiments, the method comprises securing the cartridge to the cartridge receiver. Next, in some embodiments, the method comprises imaging the target tissue using the ultrasound probe and the infrared sensor by contacting the surface of the skin of the individual with the bottom surface of the cartridge. Next, in some embodiments, the method comprises identifying the catheter insertion point on the display screen. Next, in some embodiments, the method comprises adjusting the syringe holder angle and moving the catheter longitudinally, through the cartridge inlet, thereby introducing the catheter at the catheter insertion point and into the target tissue.

Needle Insertion Algorithm

The needle insertion system can be used to determine the required needle insertion path of during the insertion process. The designated insertion path can be followed to place the needle and catheter within the lumen of the target vessel. The insertion path can be driven by an algorithm developed for the insertion device.

In some embodiments, the needle insertion algorithm for the insertion system can be generalized in 3D space as a 6+ Degree Of Freedom (DOF) system.

The insertion system can operate under a designed needle tip path, defined as:

$$N = f(\bar{x}, \vec{n})$$

Where: $\bar{x}$ is the needle tip position;

$\vec{n}$ is the vector direction pointing coaxially along the needle; and

Both $\bar{x}$ and $\vec{n}$ are parametrized as $\hat{x}(S)$, $\vec{n}(S) \cdot S$ is defined as the % of path for a given step.

The required needle path can be inputted into the insertion system by the user and the inputs can be translated and relayed by the insertion system to an actuator space defined as:

$$U = (A, B, C, D, \ldots)$$

Figure 20:
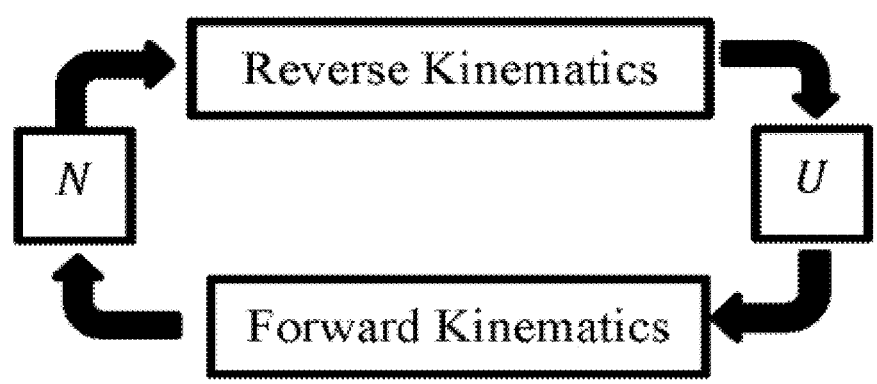
FIG. 20 depicts an operating principle for an insertion system.

In the given actuator space, user inputs can set the joint position/velocities through reverse kinematics. The operating principle for the insertion system can be a rigid body assumption as shown in FIG. 20.

Figure 18:
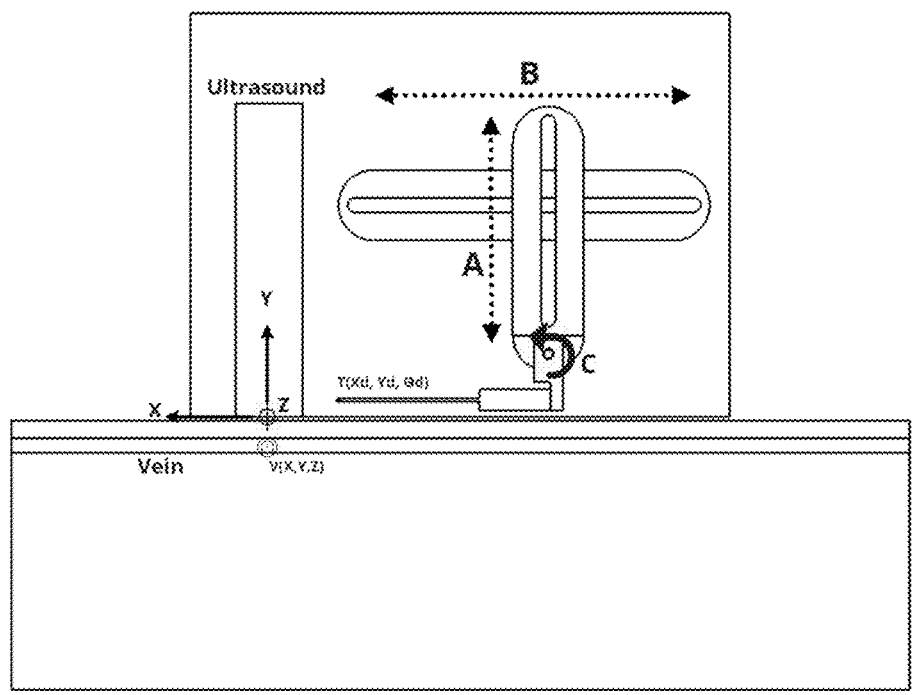
FIG. 18 shows a schematic of actuators and needle when the needle is in a docketed position.

The needle insertion algorithm can provide detailed steps of the needle path starting from the docked position. FIG. 18 illustrates the needle in the docked position. A and B are actuators that can drive the needle. The detailed steps can include mathematical equations and structures involved in the process. The equations disclosed herein can be adapted depending on the required input into the actuators.

In some embodiments, the needle docked position can be defined as below:

$$T(X_d, Y_d, \theta_d) = \text{Tip Docked Position}$$

$$T(X_d, Y_d, \theta_d) = \text{Tip Docked Position}$$

The ultrasound plane can be centered over V(X, Y, Z), where: Y=Vessel Depth. The origin may be defined at the ultrasound probe head. For 2D problem, Z can be equal to 0.

Stage 1: Horizontal Needle Tip Positioning

In the first stage, the needle tip position can be adjusted along the x-axis. In some embodiments, the needle tip is positioned such that when it rotates to the insertion angle, the needle body is lined up with the target vessel position V.

Figure 19A:
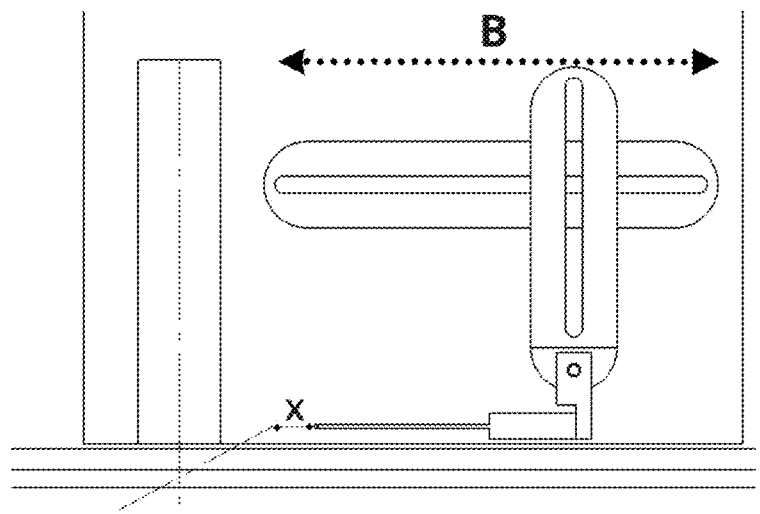
FIGS. 19A-19E show the schematic of actuators and needle at different stages of insertion path.
Figure 19B:
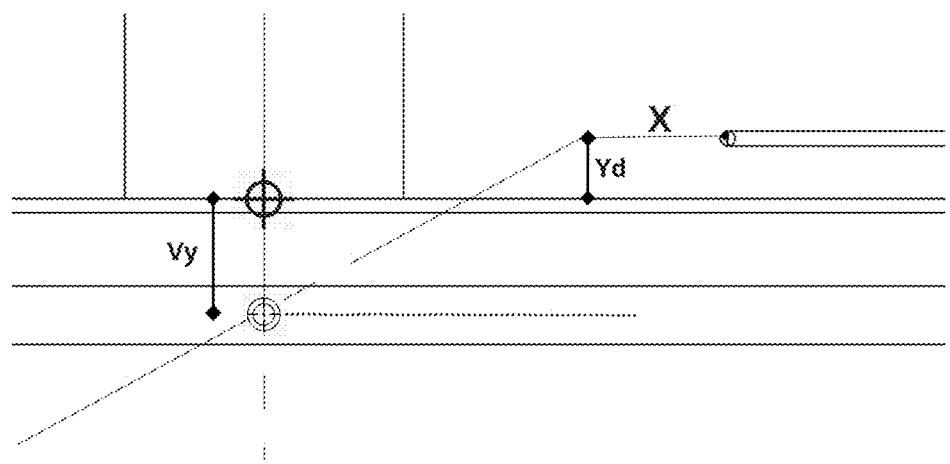

The needle tip can be adjusted via actuator B along the x-axis by a given displacement X as shown in FIG. 19A. FIG. 19B shows the movement of the needle for horizontal needle tip adjustment. The required position of X can be defined by the following equation and insertion angle.

$$\frac{V_y + Y_d}{X_d + X} = \tan\theta_I$$

$\theta_I$ = Insertion Angle( ~ 30°)

Where: $V_y$ is the vertical distance from the Ultrasound Probe head to the target vessel;
$Y_d$ is the vertical distance from the needle tip to the Ultrasound Probe head; and
$X_d$ is the starting positon of the needle tip along the X axis.

The insertion angle can be determined by the insertion parameters set by the user or defined by the insertion device. The required movement distance of actuator B can be defined as X given the equation:

$$X = \frac{V_y + Y_d}{\tan\theta_I} - X_d$$

Stage 2: Needle Rotation about Tip to Insertion Angle

In stage two, the needle can be rotated about the needle tip to reach the insertion angle $\theta_1$ defined by the user or the insertion system.

Figure 19C:
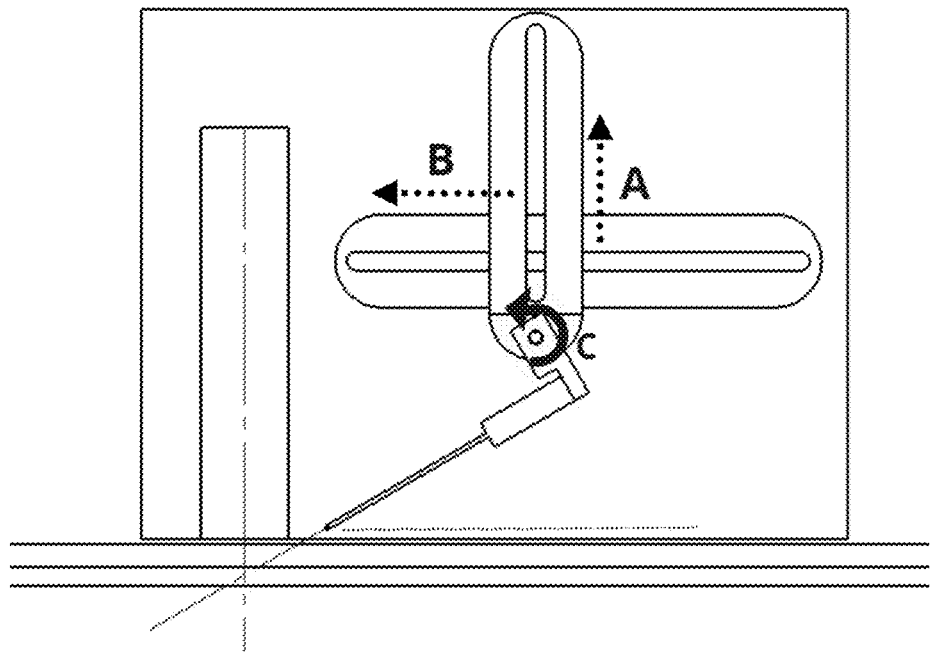

Each actuator can be adjusted in actuator space U (A, B C) to rotate the needle (FIG. 19C), given the following equations as a function of needle tip position θ, X, Y.

$C(\theta,X,Y)=\theta$ $B(\theta,X,Y)=B\circ+L_c \sin\theta-L_N \cos\theta$ $A(\theta,X,Y)=A\circ+L_c \cos\theta-L_N \sin\theta$ Where: B∘ is the starting position of the B actuator during stage 2;
A∘ is the starting point of the A actuator during stage 2;
$L_c$ is the length of the arm of actuator C (centerline of needle to center of rotation for C); and
$L_N$ is the length of the needle.

Stage 3: Inserting Needle to Vein

Figure 19D:
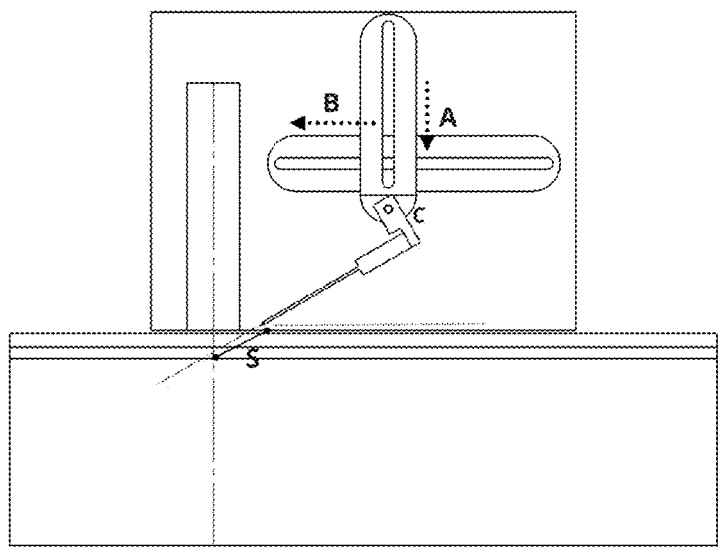

In stage three, the needle can be inserted by an insertion distance defined by the parameter S. The needle tip can start at position 0 and end at position S when the needle tip is inside the target vessel (FIG. 19D).

The value of S can be defined as:

$$S=\sqrt{(V_y+Y_d)^2+(V_x-X_d)^2}$$

Where: $V_y$ is the vertical distance from the Ultrasound Probe head to the target vessel.
$Y_d$ is the vertical distance from the needle tip to the Ultrasound Probe head.
$X_d$ is the horizontal position of the needle tip from the Ultrasound Probe head.
$V_x$ is the horizontal position of the vessel from the Ultrasound Probe head.

Given S, the actuator space equations for actuator A and B can be defined as below:

$B(\theta,X,Y)=S*\cos\theta+X_1$ $C(\theta,X,Y)=-S*\sin\theta+Y_1$

As the needle insertion goes from 0→S, actuator C can remain at $\theta_1$.

Stage 4: Needle Lowered from Insertion Angle

In stage four, the needle can be rotated by the needle tip to lower its insertion angle to some defined angle ($\theta_v$) for advancing into the lumen. The equations for rotations to $\theta_v$, can be the same as in stage two.

For stage four, the value of angle $\theta_v$, can depend on the patient's anatomy. It may not be possible to achieve a $\theta_v$, =0, rather θ, may be $\theta_v$>0.

$C=\theta_v<\theta_1 \&\& \theta_v>0$ $B(\theta,X,Y)=B\circ+L_c \sin\theta-L_N \cos\theta+X_f$ $A(\theta,X,Y)=A\circ+L_c \cos\theta-L_N \sin\theta+Y_f$ $Y_f=-\Delta Y_d$ One likely phenomenon the needle could experience is the fencepost effect. When trying to pivot the needle about the needle tip within an elastic medium (human tissue), the needle can experience a bending moment somewhere between the needle tip and the base of the needle. The bending moment may result in a deflection of the needle body, causing the needle tip to drift from the vessel center. A solution to the fencepost effect can include some adjustment of Y_f to account for the drift in needle tip position along the Y axis. There may also be some adjustment required in the X axis due to the fencepost effect defined as X_f.

$Y_f$ or $X_f$ would be applied manually by an operator or automatically through detection of the needle tip using ultrasound.

Stage 5: Advancing Needle into Lumen

Figure 19E:
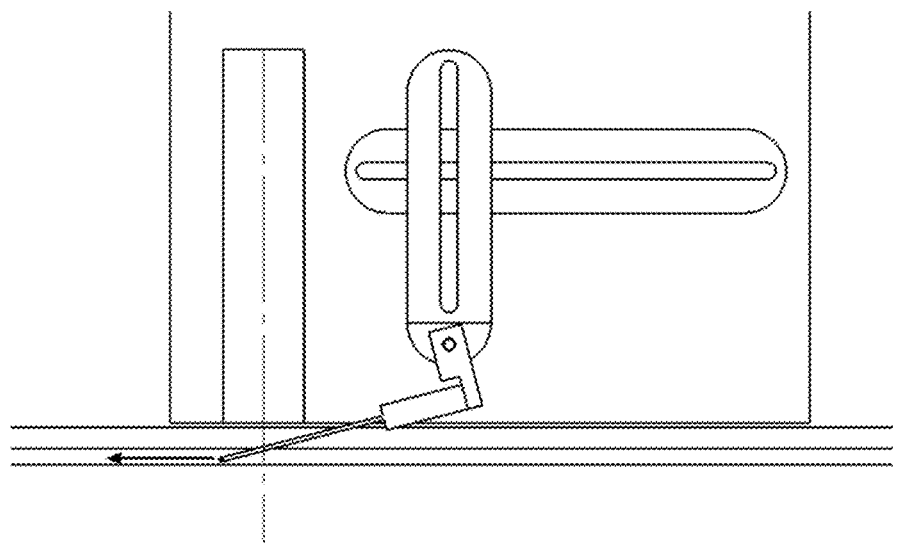

In stage five, the needle is advanced along the lumen of the vessel. The needle can be advanced along the centerline of the vessel defined as $V^{\rightarrow}$ (FIG. 19E). $V^{\rightarrow}$ can be calculated using a sweep of the ultrasound when the device is placed, or in real time by the user during advancement of the needle.

Needle Insertion Systems

Disclosed herein, in certain embodiments, are insertion systems for inserting a needle into a target tissue in an individual in need thereof. In some embodiments, the present disclosure provides a system for needle insertion and/or needle placement into a target tissue in an individual in need thereof. In some embodiments, the system comprises any of the devices for needle insertion and/or placement disclosed herein.

In some embodiments, the insertion system comprises an insertion device. In some embodiments, the insertion system comprises any of the embodiments of the insertion device and/or related parts disclosed herein. In some embodiments, the insertion device comprises a housing. In some embodiments, the housing comprises an ultrasound transducer configured to emit and receive an ultrasound wave. In some embodiments, the insertion device comprises a cartridge receiver comprising a plurality of first connectors. In some embodiments, the insertion device comprises a cartridge having a top surface, a bottom surface, a proximal end, and a distal end. In some embodiments, the cartridge is configured to be coupled to the cartridge receiver. In some embodiments, the cartridge comprises a plurality of second connectors located on the top surface of the cartridge. In some embodiments, the plurality of second connectors is configured to form an electrical connection with the plurality of first connectors of the cartridge receiver.

In some embodiments, the insertion device comprises a plate having a planar surface and a thickness configured to allow the ultrasound wave to pass therethrough. In some embodiments, the insertion device comprises a syringe holder. In some embodiments, the needle holder comprises an interior having a proximal end and distal end and a track therebetween. In some embodiments, the track has track walls configured to guide the needle. In some embodiments, the needle holder comprises a needle connector configured to couple the needle to a plurality of actuators. In some embodiments, the needle holder comprises a needle holder opening located at the distal end of the needle holder. In some embodiments, the needle holder comprises a port located at the proximal end of the needle holder. In some embodiments, the needle exits through the needle holder opening.

In some embodiments, the insertion device comprises an infrared sensor configured to emit and receive an infrared radiation. In some embodiments, the insertion device comprises a display screen operatively coupled to the ultrasound transducer and the infrared sensor.

Display Screen

In some embodiments, the insertion device comprises a display screen. Alternatively, in other embodiments, the insertion device does not comprise a display screen. In some embodiments, the display screen is configured to display an ultrasound image and an infrared image of the target tissue location, the needle, and a needle insertion point. In some embodiments, the imaging devices comprise a display screen operatively coupled to the ultrasound transducer and the infrared sensor. In some embodiments, the display screen is configured to display an ultrasound image and an infrared image of the target tissue. In some embodiments, the display screen is operatively coupled to an ultrasound transducer. In some embodiments, the display screen is configured to display an ultrasound image of the target tissue location in the individual in need thereof. In some embodiments, the display screen is configured to display a needle. In some embodiments, the display screen is configured to display a needle insertion point.

In some embodiments, the display screen displays an ultrasound image of the target tissue location in the individual in need thereof, in real time. In some embodiments, the display screen displays the needle in real time. In some embodiments, the display screen displays a needle insertion point in real time. In some embodiments, the system comprises a user interface operatively coupled to the computing device. In some embodiments, the display screen is a user interface. In some embodiments, the user interface comprises a touch screen and/or a plurality of buttons to control various functions of the vacuum-assisted insertion system.

In some embodiments, the display screen displays a virtual needle point during needle insertion. Once the tip of the needle enters the lumen of a vessel, the needle can be pivoted co-axially with the vessel. The catheter can be subsequently released from the needle. To minimize the risk of tearing the outer wall of the vessel during the pivoting process, the insertion system can provide a virtual pivot point at or around the intersection of the vessel wall and the needle. In another embodiment, the needle can be pivoted about the needle tip.

In some embodiments, the display screen is a computer screen, a mobile device screen, or a portable device screen. In some embodiments, the display screen is a cathode ray tube (CRT). In some embodiments, the display screen is a liquid crystal display (LCD). In further embodiments, the display screen is a thin film transistor liquid crystal display (TFT-LCD). In some embodiments, the display screen is an organic light emitting diode (OLED) display. In various further embodiments, an OLED display is a passive-matrix OLED (PMOLED) or active-matrix OLED (AMOLED) display. In some embodiments, the display screen is a plasma display. In other embodiments, the display screen is a video projector. In still further embodiments, the display screen is a combination of devices such as those disclosed herein.

Computing Device

In some embodiments, the insertion system comprises a computing device. In some embodiments, the computing device comprises a processor operatively coupled to the ultrasound transducer. In some embodiments, the computing device comprises a processor operatively coupled to the infrared sensor. In some embodiments, the computing device comprises a processor operatively coupled to the display screen. In some embodiments, the computing device comprises a processor operatively coupled to the plurality of actuators.

In some embodiments, the computing device comprises a non-transitory computer readable storage medium with a computer program including instructions executable by the processor. In some embodiments, the non-transitory computer readable storage medium is a memory. In some embodiments, the computer program causes the processor to: a) convert the ultrasound wave emitted from the ultrasound transducer into the ultrasound image and display the ultrasound image on the display screen, b) convert the infrared radiation emitted from the infrared sensor into the infrared image and display the infrared image on the display screen, c) localize the target tissue, d) calculate the needle insertion point into the target tissue, and e) track the position of the tip of the needle once the needle is inserted into the target tissue.

In some embodiments, the instructions that are executable by the processor cause the processor to localize the target tissue. In some embodiments, the instructions that are executable by the processor cause the processor to calculate the needle insertion point into the target tissue. In some embodiments, the instructions that are executable by the processor cause the processor to track the position of the tip of the needle once the needle is inserted into the target tissue. In some embodiments, the instructions that are executable by the processor cause the processor to automatically adjust the position of the needle such that the needle is centered within the target tissue. In some embodiments, the instructions that are executable by the processor cause the processor to detect when the power source has a low charge and/or no charge. In some embodiments, the instructions that are executable by the processor cause the processor to detect when the power source has been recharged and/or replaced.

Computer Control Systems

Figure 12:
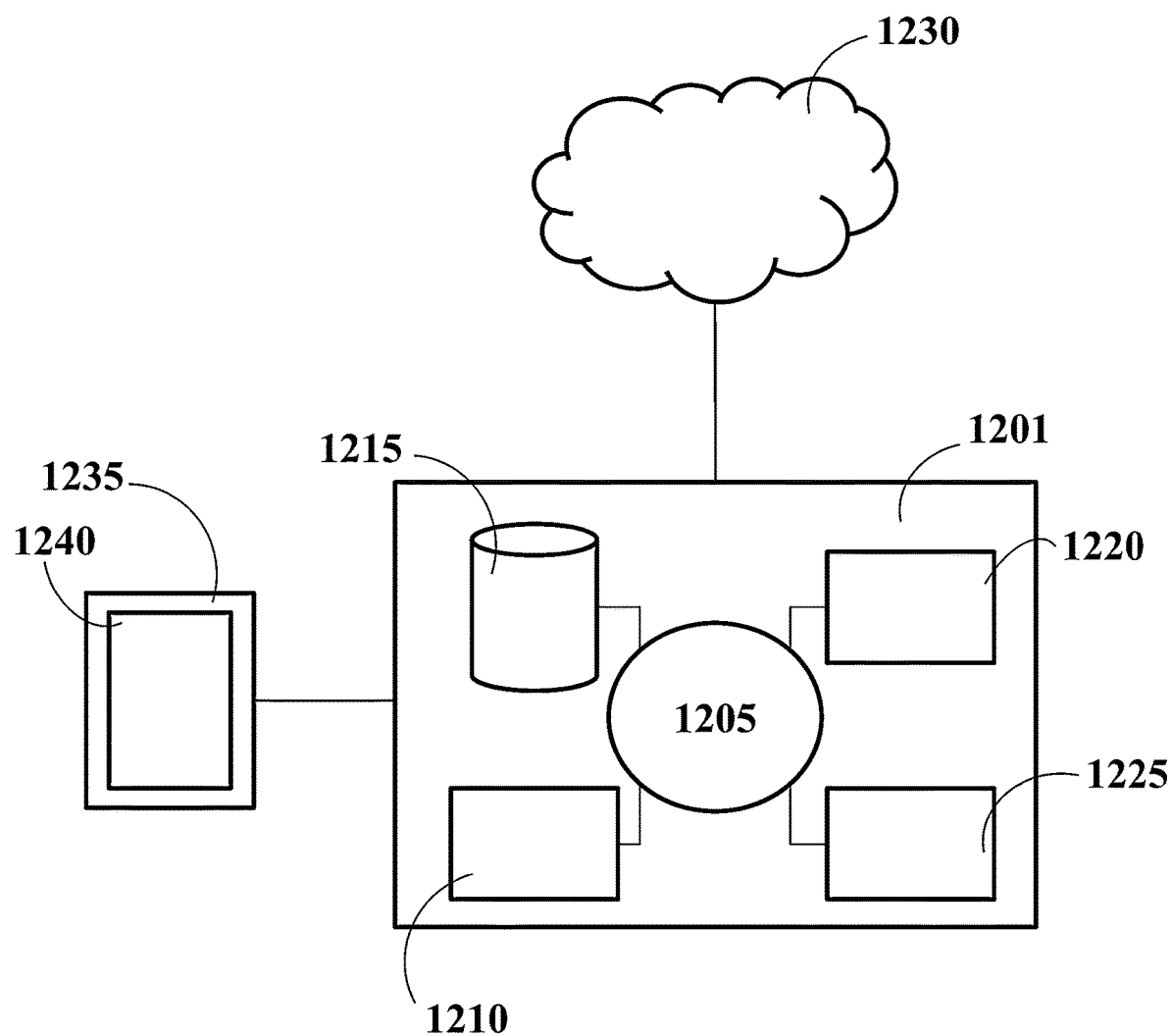
FIG. 12 illustrates a computer control system that is programmed or otherwise configured to implement methods provided herein.

The present disclosure provides computer control systems that are programmed to implement methods of the disclosure. FIG. 12 shows a computer system 1201 that is programmed or otherwise configured to, for example, convert an ultrasound wave emitted from the ultrasound transducer into an ultrasound image; display the ultrasound image on a display screen, localize a target tissue, calculate a needle insertion point into a target tissue, track the position of a tip of a needle once the needle is inserted into a target tissue; and/or automatically adjust the position of the needle such that the needle is centered within the target tissue. In some embodiments, the computer system 701 regulates various aspects of needle insertion methods, needle placement methods, and systems of the present disclosure, such as, for example, calculating a needle insertion point into a target tissue. In some embodiments, the computer system 1201 is an electronic device of a user or a computer system that is remotely located with respect to the electronic device. In some embodiments, the electronic device is a mobile electronic device. In some embodiments, the computer system 1201 is an electronic device or a computer system that is located within the insertion device.

In some embodiments, the computer system 1201 includes a central processing unit (CPU, also "processor" and "computer processor" herein) 1205, which is a single core or multi core processor, or a plurality of processors for parallel processing. In some embodiments, the computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. In some embodiments, the memory 1210, storage unit 1215, interface 1220 and peripheral devices 1225 are in communication with the CPU 1205 through a communication bus (solid lines), such as a motherboard. In some embodiments, the storage unit 1215 is a data storage unit (or data repository) for storing data. In some embodiments, the computer system 1201 is operatively coupled to a computer network ("network") 1230 with the aid of the communication interface 1220. In some embodiments, the network 1230 is the Internet, an internet and/or extranet, or an intranet and/or extranet that is in communication with the Internet. In some embodiments, the network 1230 is a telecommunication and/or data network. In some embodiments, the network 1230 includes one or more computer servers, which enable distributed computing, such as cloud computing. In some embodiments, the network 1230, with the aid of the computer system 1201, implements a peer-to-peer network, which enables devices coupled to the computer system 1201 to behave as a client or a server.

In some embodiments, the CPU 1205 executes a sequence of machine-readable instructions, which are embodied in a program or software. In some embodiments, the instructions are stored in a memory location, such as the memory 1210. In some embodiments, the instructions are directed to the CPU 1205, which subsequently program or otherwise configure the CPU 1205 to implement methods of the present disclosure. Non-limiting examples of operations performed by the CPU 1205 include fetch, decode, execute, and writeback.

In some embodiments, the CPU 1205 is part of a circuit, such as an integrated circuit. In some embodiments, one or more other components of the system 1201 are included in the circuit. In some cases, the circuit is an application specific integrated circuit (ASIC).

In some embodiments, the storage unit 1215 stores files, such as drivers, libraries, and saved programs. In some embodiments, the storage unit 715 stores user data, e.g., user preferences and user programs. In some embodiments, the computer system 1201 includes one or more additional data storage units that are external to the computer system 701, such as located on a remote server that is in communication with the computer system 1201 through an intranet or the Internet.

In some embodiments, the computer system 1201 communicates with one or more remote computer systems through the network 1230. For instance, in some embodiments, the computer system 1201 communicates with a remote computer system of a user (e.g., a personal computer). Non-limiting examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. In some embodiments, the user accesses the computer system 1201 via the network 1230.

In some embodiments, methods as described herein are implemented by way of machine (e.g., computer processor) executable code stored on an electronic storage location of the computer system 1201, such as, for example, on the memory 1210 or electronic storage unit 1215. In some embodiments, the machine executable or machine readable code is provided in the form of software. In some embodiments, during use, the code is executed by the processor 1205. In some embodiments, the code is retrieved from the storage unit 1215 and stored on the memory 1210 for ready access by the processor 1205. In some embodiments, the electronic storage unit 1215 is precluded, and machine-executable instructions are stored on memory 1210.

In some embodiments, the code is pre-compiled and configured for use with a machine having a processor adapted to execute the code, or is compiled during runtime. In some embodiments, the code is supplied in a programming language that is selected to enable the code to execute in a pre-compiled or as-compiled fashion.

In some embodiments, aspects of the systems and methods provided herein, such as the computer system 1201, are embodied in programming. In some embodiments, various aspects of the technology are thought of as "products" or "articles of manufacture" typically in the form of machine (or processor) executable code and/or associated data that is carried on or embodied in a type of machine readable medium. In some embodiments, machine-executable code is stored on an electronic storage unit, such as memory (e.g., read-only memory, random-access memory, flash memory) or a hard disk. In some embodiments, "storage" type media includes any or all of the tangible memory of the computers, processors or the like, or associated modules thereof, such as various semiconductor memories, tape drives, disk drives and the like, which provide non-transitory storage at any time for the software programming. In some embodiments, all or portions of the software are, at times, communicated through the Internet or various other telecommunication networks. In some embodiments, such communications, for example, enable loading of the software from one computer or processor into another, for example, from a management server or host computer into the computer platform of an application server. Thus, another type of media that bears the software elements, in some embodiments, includes optical, electrical and electromagnetic waves, such as used across physical interfaces between local devices, through wired and optical landline networks and over various air-links. In some embodiments, the physical elements that carry such waves, such as wired or wireless links, optical links or the like, are also considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, in some embodiments, takes many forms, including but not limited to, a tangible storage medium, a carrier wave medium, or a physical transmission medium. In some embodiments, non-volatile storage media include, for example, optical or magnetic disks, such as any of the storage devices in any computer(s) or the like, such as are used to implement the databases, etc. shown in the drawings.

In some embodiments, volatile storage media include dynamic memory, such as main memory of such a computer platform. In some embodiments, tangible transmission media include coaxial cables; copper wire and fiber optics, including the wires that comprise a bus within a computer system. In some embodiments, carrier-wave transmission media take the form of electric or electromagnetic signals, or acoustic or light waves such as those generated during radio frequency (RF) and infrared (IR) data communications. In some embodiments, common forms of computer-readable media therefore include, for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer reads programming code and/or data. In some embodiments, many of these forms of computer readable media are involved in carrying one or more sequences of one or more instructions to a processor for execution.

In some embodiments, the computer system 1201 includes or is in communication with an electronic display 1235 that comprises a user interface (UI) 1240 for providing, for example, the display screen 1202 of the insertion device. Examples of UI's include, without limitation, a graphical user interface (GUI) and web-based user interface.

In some embodiments, methods and systems of the present disclosure are implemented by way of one or more algorithms. In some embodiments, an algorithm is implemented by way of software upon execution by the central processing unit 1205. In some embodiments, the algorithm, for example, calculates a needle insertion point into a target tissue based on an ultrasound image.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1: Venous Blood Withdrawal Using an Insertion Device

A health care worker performs a venous blood withdrawal on a patient using the insertion device described herein. The health care worker inserts the peripheral intravenous site and phlebotomy cartridge 174 into the cartridge receiver of the insertion device. The health care worker inserts the collection tube into the port, which allows the collection tube to be in fluid communication with the needle. The health care worker then presses the bottom surface of the cartridge onto the left arm of the patient. With the sensor areas in place, the ultrasound probe and the infrared sensor generate an image of the blood vessels of the left arm of the patient. The ultrasound image and the infrared image are shown as an overlay image and displayed on the display screen. The health care worker adjusts the placement of the insertion device, guided by the image displayed on the display screen, until she identifies the median cubital vein in the antecubital fossa in the left arm of the patient. The image displayed on the display screen also shows an indicator line and insertion indicator marking to allow for identification of the needle insertion point. The health care worker activates the vacuum motor by pressing the vacuum seal button on the insertion device. Activation of the vacuum motor creates suction between the insertion device and the surface of the skin of the patient in the needle insertion region of the left arm of the patient. The health care worker adjusts the angle of the needle by using the gear wheel of the insertion device. The health care worker adjusts the longitudinal position of the needle by using the positioning dial of the insertion device. The health care worker inserts the needle at the proper point of insertion by depressing the needle insertion button of the insertion device. Once the needle is inserted into the patient, the insertion device displays the position of the needle in real time on the display screen. The health care worker ensures the needle enters the median cubital vein and begins collecting venous blood into the collection tube upon accessing the lumen of the vein. Once a sufficient venous blood volume is collected, the health care worker withdraws the needle by pressing the needle withdrawal button.

Example 2: Venous Injection Using an Insertion Device

A health care worker performs an injection on a patient using the insertion device described herein. The health care worker inserts the cartridge into the cartridge receiver of the insertion device. The health care worker then presses the cartridge onto the left arm of the patient. With the sensor areas in place, the ultrasound probe and the infrared sensor generate an image of the blood vessels of the left arm of the patient. The ultrasound image and the infrared image are shown as an overlay image and displayed on the display screen. The health care worker adjusts the placement of the insertion device, guided by the image displayed on the display screen, until she identifies the median cubital vein in the antecubital fossa in the left arm of the patient. The image displayed on the display screen also shows an indicator line and insertion indicator marking to allow for identification of the needle insertion point. The health care worker activates the vacuum motor by pressing the vacuum seal button on the insertion device. Activation of the vacuum motor creates suction between the insertion device and the surface of the skin of the patient in the needle insertion region of the left arm of the patient. The health care worker adjusts the angle and the position of the needle. The health care worker inserts the needle at the proper point of insertion by depressing the needle insertion button of the insertion device. Once the needle is inserted into the patient, the insertion device displays the position of the needle in real time on the display screen. The health care worker ensures the needle and catheter enters the median cubital vein. Once the needle and the catheter enter the vein, the health care worker triggers releasing mechanism to detach the catheter from the insertion device and withdraw needle away from the vein by pressing withdrawal button. A medication is infused through the catheter. Once a sufficient amount of medication is infused, the health care worker withdraws the catheter. Alternatively, the health care worker connects a syringe the needle and injects medication through the needle without using the catheter.

Example 3: Lumbar Puncture Using an Insertion Device

A health care worker performs a biopsy on a patient using the insertion device described herein. The health care worker inserts the cartridge into the cartridge receiver of the insertion device. The health care worker inserts the collection tube into the port, which allows the collection tube to be in fluid communication with the needle. The health care worker then presses the bottom surface of the cartridge into the spinal column of the patient. With the sensor areas in place, the ultrasound probe and the infrared sensor generate an image of the spinal column of the patient. The ultrasound image and the infrared image are shown as an overlay image and displayed on the display screen. The health care worker adjusts the placement of the insertion device, guided by the image displayed on the display screen, until she identifies a proper insertion site. The image displayed on the display screen also shows an indicator line and insertion indicator marking to allow for identification of the needle insertion point. The health care worker activates the vacuum motor by pressing the vacuum seal button on the insertion device. Activation of the vacuum motor creates suction between the insertion device and the surface of the skin of the patient in the needle insertion region. The health care worker adjusts the angle of the needle by using the gear wheel of the insertion device. The health care worker adjusts the longitudinal position of the needle by using the positioning dial of the insertion device. The health care worker inserts the needle at the proper point of insertion by depressing the needle insertion button of the insertion device. Once the needle is inserted into the patient, the insertion device displays the position of the needle in real time on the display screen. The health care worker ensures the needle enters the spinal cord and begins collecting cerebrospinal fluid into the collection tube upon accessing the cavity of the spinal cord. Once a sufficient cerebrospinal fluid is collected, the health care worker withdraws the needle by pressing the needle withdrawal button.

Example 4: Abdominal Paracentesis Using an Insertion Device

The patient is placed in a supine position with lower extremities covered by a sheet and the arms preferably held above their head. The user assumes a position lateral to the left side of the patient's abdomen. Then the area on the left lateral frontal aspect of the lower abdomen, slightly inferior to the umbilicus at the lateral position in alignment with the anterior axillary line is broadly sterilized using betadine, chlorohexidine, or another fluid for sterilization. The specific cartridge intended for paracentesis procedures is removed from its sterile packaging in sterile fashion and attached to the bottom surface of the housing. The sensors on the housing which recognize the type of cartridge attached send a signal to the onboard computer, and the computer processes this information then sends a signal to control the ultrasound probe and displays screen to their standard initial positions, and the ultrasound probe assumes a horizontal position within the device that is a set distance longitudinally from the proximal most possible ultrasound probe position within the housing and the displayed probe depth is automatically adjusted to the preferred depth for the paracentesis procedure. The sterile sleeve connected to the cartridge is then pulled over the entirety of the device by the user, such that the sleeve creates a sterile barrier between the user and all of the buttons, handles, controls, and displays of the device. The user then places the bottom of the device (which has the attached cartridge) on the patient's left lower abdomen. The curvature of the bottom of this cartridge is semi-circular such that the curve is oriented in the horizontal direction. The user then moves the device about this area of the abdomen searching for the largest area of free fluid within the abdomen. When the area of maximum ascites is identified, the device is oriented such that the largest area of fluid coincides with the center vertical line on the display screen. The device's targeted vacuum suction is then activated, such that there is a vacuum suction created on the bottom the cartridge, effectively attaching the cartridge and device to the abdominal wall and distorting the soft tissue under the vacuum regions. While remaining attached to the abdomen, the user controls the prob position while the probe remains in horizontal orientation within the housing, the user does a longitudinal sweep with the probe going both proximal to the initial position and then distal before returning the probe to the initial position. The user can activate the doppler affect of the device before the sweep such that vessels which may lie in the path of the needle can be identified and the device detached and adjusted if necessary. The user may choose to select the small needle, and target the tissue in the planned path for the large needle, and inject lidocaine into this area. If the anticipated path of the needle appears safe, the user then adjusts the target location of the needle presented on the display screen of the needle to an area within the free fluid just below the interior wall of the abdominal cavity. Once targeted, the needle advancement is triggered by the user which sends a signal to the onboard computer. The signal is computed, and then an outgoing signal from the computer is sent to the actuators and needle position portions of the device to change the angle, position, and advancement of the needle so that the needle tip advances in a chosen angle to the targeted location. If the user decides to advance the needle further, the probe position can then be changed by the user to a more distal location, and this process repeated one or more times, such that the needle tip is advanced farther into the ascites fluid. Once the needle tip is in a satisfactory location, the user can attach tubing to the side port of the cartridge which is attached inside of the device to fluid tubing and the needle, and fluid can be drawn out of the patient's abdomen using a syringe, vacuum bottle, wall suction or other device. Alternatively, the user may choose the initial target of the large needle to be just superior to the interior border of the abdominal wall, a small distance from that tissue layer, then activate a safety needle within the lumen of the large needle to extend to a further target location, thereby piercing the internal aspect of the abdominal wall without risking penetration into a loop of bowel or other intra-abdominal organ. Medication or fluids can be injected into the abdominal fluid within the cavity. Alternatively, tubing can be connected to the external port of the cartridge, and fluid can be drained. Another option for the user once the needle tip is advanced to a satisfactory location, is that a catheter can be advanced over the needle into the abdominal fluid and exterior portion of that catheter attached to the exterior abdominal wall, and the user can press the end procedure button and the device can be removed.

Example 5: Knee Joint Injection Using an Insertion Device

The patient is placed in a supine position with the knee in a slightly flexed position. The area on the front on the leg just proximal to the patella is broadly sterilized using betadine, chlorohexidine, or another fluid for sterilization. The specific cartridge intended for knee injections is removed from its sterile packaging in sterile fashion and attached to the bottom surface of the housing. The sensors on the housing which recognize the type of cartridge that has been attached sends a signal to the onboard computer, and the computer processes this information then sends a signal to control the ultrasound probe into its standard initial position, and the ultrasound probe assumes a horizontal position within the device a set distance longitudinally from the proximal most possible ultrasound probe position within the housing. The Sterile sleeve connected to the cartridge is then pulled over the entirety of the device by the user, such that the sleeve creates a sterile barrier between the user and all of the buttons, handles, controls, and displays of the device. The user then places the bottom of the device (which has the attached cartridge) on the patient's leg, just proximal to the patella. The curvature of the bottom of this cartridge is semi-circular such that the curve is oriented in the same direction of curvature of the leg, with the curvature varying in the longitudinal plane and the ultrasound probe is in a parallel orientation relative to the femur of the patient. The user then moves the device about the leg, such that the cartridge remains in contact with the leg, and the displayed image is viewed by the user, and the movement is stopped when the supra-patellar pouch is aligned with the center line of the image. While the device remains still on the patient, the ultrasound probe rotation knob is then turned, such that the ultrasound probe is turned 90 degrees relative to the housing, and then the probe and ultrasound plane sits in a perpendicular plane relative to the femur and longitudinal plane relative to the device. The position of the device can again be adjusted by the user at this time, so that the needle target line is aimed at the supra-patellar pouch. The device's targeted vacuum suction is then activated, such that there is a vacuum suction created on the bottom the cartridge, effectively attaching the cartridge and device to the leg and distorting the soft tissue under the vacuum regions. While remaining attached to the leg, the user puts gentle traction on the device slightly distally down the leg and slightly laterally relative to the leg, thereby effectively consolidating and pushing the suprapatellar fluid into a more concentrated position and making it easier to target with the needle. The needle path and distal end point is then selected using the controls targeting the central fluid area within the suprapatellar pouch, and the needle advance button is pressed, which causes the needle within the cartridge to advance into the patient's leg through the selected path and the needle advancement stops at the selected needle endpoint. The user can select a new target endpoint and plane of entry within the knee, and the needle can be advanced again by the user pressing the needle advancement button. With the needle tip well within the supra-patellar pouch, the port and flow tubing connected to the needle can be accessed, and fluid can be drawn out into a syringe, or a syringe containing liquid can be attached and used to inject that liquid into the knee. Fluid can be withdrawn from the pouch, liquid can be injected into the pouch, or both of these steps can be taken with one or more syringes or tubes. The End or abort button can be pressed by the user to withdrawal the needle, and the vacuum suction can then be stopped can device released from the leg of the patient.

Example 6: Thoracostomy Tube Placement Using an Insertion Device

The patient is placed in a supine position with lower extremities covered by a sheet and the arms preferably held above their head. The user assumes a position lateral to the left side of the patient's chest wall. At the left mid-axillary line and the 4th or 5th rib space, the skin is broadly sterilized using betadine, chlorohexidine, or another fluid for sterilization, and sterile drapes are placed on the patient. The specific cartridge intended for thoracostomy procedures is removed from its sterile packaging in sterile fashion and attached to the bottom surface of the housing of the device. The shape of the thoracostomy procedure cartridge has two portions to the bottom surface, with the more proximal portion angled distally and the more distal portion angled distally at a steeper angle than the proximal portion. The more distal end of the cartridge contains an array of vacuum suction areas. The sensors on the housing, which recognize the type of cartridge have been attached, send a signal to the onboard computer, and the computer processes this information then sends a signal to control the ultrasound probe and display screen to their standard initial positions, and the ultrasound probe assumes a longitudinal position within the device a set distance longitudinally from the proximal most possible ultrasound probe position within the housing and the displayed probe depth is automatically adjusted to the preferred depth for the thoracostomy procedure. The sterile sleeve connected to the cartridge is then pulled over the entirety of the device by the user, such that the sleeve creates a sterile barrier between the user and all of the buttons, handles, controls, and displays of the device. The user then places the distal portion of the bottom of the cartridge on the left lateral chest wall at the 5th intercostal space in the mid-axillary line and orients the device to be perpendicular to the ribs. The user then moves the device about this area of the chest wall to identify an ideal position of the device. Once identified, the user activates the vacuum suction, tightly adhering the cartridge and device in place on the chest wall. The device's targeted vacuum suction is then activated, such that there is a vacuum suction created on the bottom the cartridge, effectively attaching the cartridge and device to the abdominal wall and distorting the soft tissue under the vacuum regions thereby stabilizing the skin and tissue at the ultrasound probe location. While remaining attached to the chest, the user sweeps the probe in the horizontal and longitudinal directions. When the user has found a desirable target location, just superior to one of the ribs, the user selects and activates the small needle within the cartridge. The user then targets the area planned for tube insertion, and activates the insertion of the small needle to this area in a superficial position under the skin surface. The user then selects the amount of lidocaine to dispense from the prefilled sterile container within the cartridge and injects the medication. The user then advances the small needle repeating these steps and injects more doses of the anesthetizing medication before selecting to withdraw the small needle using the controls on the device. The user then activates the large needle, and determines the most desirable path and target, with the path coursing at an angle of approximately 80 degrees just superior to the rib and target just within the plural cavity, controlling these with the device controllers. The user then activates the insertion of the long needle to that position. These steps can be repeated and the needle further inserted. Once the needle is in satisfactory position, the user can choose on the device to then advance the thoracostomy guidewire that is preloaded in the cartridge, or advance a small thoracostomy tube over the needle for an emergent or temporizing thoracic decompression. after the guidewire is advanced, the user can choose to end the procedure by selecting and pressing the end button on the device, which withdraws the needle to a locked position within the cartridge, releases the vacuum, and can release the guidewire from the cartridge. After which time the user can continue the tube thoracostomy procedure using the Sledinger technique.

What is claimed is:

1. An insertion device for inserting a needle into a target tissue in an individual in need thereof, comprising:
 a housing comprising:
  a cartridge receiver comprising a plurality of first connectors;
   a cartridge having a top surface, a bottom surface, a proximal end, and a distal end, the cartridge configured to be coupled to the cartridge receiver, comprising:
  a plurality of second connectors located on the top surface of the cartridge, configured to form an electrical connection with the plurality of first connectors of the cartridge receiver, and
  a needle holder, comprising an interior having a proximal end and distal end a track therebetween, the track having track walls configured to guide the needle, a needle connector configured to couple the needle to a plurality of actuators, a needle holder opening located at the distal end of the needle holder, and a port located at the proximal end of the needle holder;
  wherein the needle exits through the needle holder opening; and
   an imaging apparatus configured to image the target tissue.

2. The insertion device of claim 1, wherein the target tissue is a blood vessel, joint, soft tissue, or calcified tissue.

3. The insertion device of claim 2, wherein the soft tissue comprises a tendon, a ligament, fascia, a fibrous tissue, an adipose tissue, a nerve, a muscle, skin, or a synovial membrane.

4. The insertion device of claim 2, wherein the calcified tissue is a bone.

5. The insertion device of claim 1, wherein the housing comprises at least one handle.

6. The insertion device of claim 1, wherein the cartridge is reversibly coupled to the cartridge receiver.

7. The insertion device of claim 1, wherein the plate is fixed relative to the cartridge receiver.

8. The insertion device of claim 1, wherein the needle holder is movable angular-wise and moves within the housing.

9. The insertion device of claim 1, wherein the needle holder is angled at a needle holder angle ranging between about 0° to about 80°.

10. The insertion device of claim 1, wherein the needle is an introducer needle, a biopsy needle, or a needle trocar.

11. The insertion device of claim 1, wherein the needle comprises a catheter and/or a guidewire.

12. The insertion device of claim 11, wherein the catheter is a peripherally inserted central catheter, a central venous catheter, a urinary catheter, an arterial catheter, a venous catheter, a tunneled catheter, a port catheter, or a non-tunneled central catheter.

13. The insertion device of claim 1, wherein the needle is in flow communication with a fluid injection line.

14. The insertion device of claim 1, wherein the cartridge receiver comprises a frame having a rail on either of its sides, the rail configured to secure the needle holder.

15. The insertion device of claim 1, wherein the plurality of actuators comprises a spring actuator and an angle actuator.

16. The insertion device of claim 15, wherein the spring actuator controls the longitudinal movement of the needle.

17. The insertion device of claim 15, wherein the angle actuator controls the needle holder angle.

18. The insertion device of claim 1, comprising a vacuum connection located within the housing, the vacuum connection comprising a vacuum connector operatively connected to the cartridge.

19. The insertion device of claim 18, wherein the vacuum connector is in vacuum communication with a vacuum source.

20. The insertion device of claim 19, wherein the vacuum source is configured to draw air through the needle holder opening.

21. The insertion device of claim 19, wherein the vacuum source is configured to draw air through the bottom surface of the cartridge.

22. The insertion device of claim 1, wherein the needle holder comprises a port lever or a collection tube configured to be received by the port.

23. The insertion device of claim 22, wherein the port lever moves within a cartridge arc path as the needle holder is moved from one selected position to another.

24. The insertion device of claim 1, wherein the insertion device comprises a power source.

25. The insertion device of claim 1, wherein the insertion device comprises a disposable sleeve configured for receiving the cartridge.

26. The insertion device of claim 1, wherein the imaging apparatus is an ultrasound transducer, an infrared sensor, or a combination thereof.

27. The insertion device of claim 26, wherein the infrared sensor comprises an infrared radiation source.

28. The insertion device of claim 27, wherein the infrared radiation source is a light emitting diode (LED) or an organic light emitting diode (OLED).

29. The insertion device of claim 26, wherein the infrared sensor comprises an infrared radiation detector.

30. The insertion device of claim 29, wherein the infrared radiation detector is an infrared photodetector or a temperature detector.

31. The insertion device of claim 26, wherein the ultrasound transducer is configured to emit and receive an ultrasound wave.

32. The insertion device of claim 31, wherein the cartridge comprises a plate having a planar surface and a thickness configured to allow the ultrasound wave to pass therethrough.

33. The insertion device of claim 31, wherein the cartridge serves as a barrier between the cartridge and the insertion device or between the insertion device and the individual.

34. The insertion device of claim 1, wherein the cartridge is pre-loaded with a therapeutic agent, wherein the therapeutic agent is delivered to the individual through the needle.

35. The insertion device of claim 1, wherein the cartridge further comprises an injection device.

36. The insertion device of claim 35, wherein an anesthetizing agent is delivered to the individual through the injection device.

37. The insertion device of claim 36, wherein the injection device is an additional needle.

\* \* \* \* \*